United States Patent
Zhang et al.

(10) Patent No.: US 9,512,416 B2
(45) Date of Patent: Dec. 6, 2016

(54) ENDOGLUCANASE VARIANTS

(71) Applicant: Codexis, Inc., Redwood City, CA (US)

(72) Inventors: Xiyun Zhang, Fremont, CA (US); Sachin Patil, Redwood City, CA (US); Jie Yang, Foster City, CA (US); Ish Kumar Dhawan, Foster City, CA (US)

(73) Assignee: CODEXIS, INC., Redwood City, CA (US)

( * ) Notice: Subject to any disclaimer, the term of this patent is extended or adjusted under 35 U.S.C. 154(b) by 99 days.

(21) Appl. No.: 14/542,467

(22) Filed: Nov. 14, 2014

(65) Prior Publication Data

US 2015/0140641 A1    May 21, 2015

Related U.S. Application Data

(62) Division of application No. 13/332,114, filed on Dec. 20, 2011, now Pat. No. 8,906,689.

(60) Provisional application No. 61/425,733, filed on Dec. 21, 2010.

(51) Int. Cl.
*C12N 1/20* (2006.01)
*C12N 9/48* (2006.01)
*C12N 9/42* (2006.01)

(52) U.S. Cl.
CPC ............... *C12N 9/48* (2013.01); *C12N 9/2437* (2013.01); *C12Y 302/01004* (2013.01); *C07K 2319/21* (2013.01); *C07K 2319/23* (2013.01); *C07K 2319/24* (2013.01); *C07K 2319/42* (2013.01); *C07K 2319/43* (2013.01); *C07K 2319/50* (2013.01); *Y02E 50/16* (2013.01)

(58) Field of Classification Search
None
See application file for complete search history.

(56) References Cited

U.S. PATENT DOCUMENTS

| | | |
|---|---|---|
| 6,117,679 A | 9/2000 | Stemmer |
| 6,376,246 B1 | 4/2002 | Crameri et al. |
| 6,586,182 B1 | 7/2003 | Patten et al. |
| 2008/0220990 A1 | 9/2008 | Fox |
| 2009/0312196 A1 | 12/2009 | Colbeck et al. |

FOREIGN PATENT DOCUMENTS

| | | |
|---|---|---|
| WO | 2005/059084 A1 | 6/2005 |
| WO | WO 2007/109441 A2 | 9/2007 |
| WO | 2010/076387 A1 | 7/2010 |

OTHER PUBLICATIONS

Extended European Search Report dated May 8, 2015 for EP Patent Application No. 11851705.1, 13 pages.
Wilson, "Cellulases and biofuels", *Current Opinion in Biotechnology*, vol. 20, pp. 295-299 (2009).
Yennamalli et al., "Thermostability in endoglucanases is fold-specific", BMC Structural Biology, vol. 11, No. 1, pp. 10 (2011).
Ngo et al., "The Protein Folding Problem and Tertiary Structure Prediction," 1994, Merz et al. (ed.), Birkhauser, Boston, MA, pp. 433 and 492-495.
The International Search Report from PCT/US2011/066254, dated Apr. 11, 2012.
UniProtKB/TrEMBL ID No. B8LUY9_TALSN, entry version 10 dated Mar. 23, 2010. (1 pg) Retrieved online Mar. 20, 2012 from <www.uniprot.org/uniprot/B8LUY9.txt?version=10>.
UniProtKB/TrEMBL ID No. Q2HF16_CHAGB, entry version 24 dated Nov. 2, 2010 (1 pg) Retrieved online Mar. 20, 2012 from <www.uniprot.org/uniprot/Q2HF16.txt?version=24>.

*Primary Examiner* — Richard Hutson
(74) *Attorney, Agent, or Firm* — Kilpatrick Townsend & Stockton LLP

(57) ABSTRACT

The present invention relates to variant endoglucanases having improved thermoactivity, improved thermostability, and improved viscosity reduction activity over wild-type *M. thermophila* endoglucanase.

17 Claims, 2 Drawing Sheets

SEQUENCE LISTING

```
<160> NUMBER OF SEQ ID NOS: 13

<210> SEQ ID NO 1
<211> LENGTH: 373
<212> TYPE: PRT
<213> ORGANISM: Myceliophthora thermophilia

<400> SEQUENCE: 1

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
            20                  25                  30

Ser Gln Cys Val Pro Gly Ala Ala Ser Thr Thr Leu Gln Thr Ser Thr
        35                  40                  45

Thr Ser Arg Pro Thr Ala Thr Ser Thr Ala Pro Pro Ser Ser Thr Thr
    50                  55                  60

Ser Pro Ser Lys Gly Lys Leu Lys Trp Leu Gly Ser Asn Glu Ser Gly
65                  70                  75                  80

Ala Glu Phe Gly Glu Gly Asn Tyr Pro Gly Leu Trp Gly Lys His Phe
                85                  90                  95

Ile Phe Pro Ser Thr Ser Ala Ile Gln Thr Leu Ile Asn Asp Gly Tyr
            100                 105                 110

Asn Ile Phe Arg Ile Asp Phe Ser Met Glu Arg Leu Val Pro Asn Gln
            115                 120                 125
```

Leu Thr Ser Ser Phe Asp Glu Gly Tyr Leu Arg Asn Leu Thr Glu Val
    130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr Asn Thr Met Asp Gln Thr Leu
        195                 200                 205

Val Leu Asn Leu Asn Gln Ala Ala Ile Asp Gly Ile Arg Ala Ala Gly
    210                 215                 220

Ala Thr Ser Gln Tyr Ile Phe Val Glu Gly Asn Ala Trp Ser Gly Ala
225                 230                 235                 240

Trp Ser Trp Asn Thr Thr Asn Thr Asn Met Ala Ala Leu Thr Asp Pro
                245                 250                 255

Gln Asn Lys Ile Val Tyr Glu Met His Gln Tyr Leu Asp Ser Asp Ser
            260                 265                 270

Ser Gly Thr His Ala Glu Cys Val Ser Ser Asn Ile Gly Ala Gln Arg
        275                 280                 285

Val Val Gly Ala Thr Gln Trp Leu Arg Ala Asn Gly Lys Leu Gly Val
    290                 295                 300

Leu Gly Glu Phe Ala Gly Gly Ala Asn Ala Val Cys Gln Gln Ala Val
305                 310                 315                 320

Thr Gly Leu Leu Asp His Leu Gln Asp Asn Ser Asp Val Trp Leu Gly
                325                 330                 335

Ala Leu Trp Trp Ala Ala Gly Pro Trp Trp Gly Asp Tyr Met Tyr Ser
            340                 345                 350

Phe Glu Pro Pro Ser Gly Thr Gly Tyr Val Asn Tyr Asn Ser Ile Leu
        355                 360                 365

Lys Lys Tyr Leu Pro
    370

<210> SEQ ID NO 2
<211> LENGTH: 1203
<212> TYPE: DNA
<213> ORGANISM: Artificial Sequence
<220> FEATURE:
<223> OTHER INFORMATION: Synthetic DNA which is codon-optimized cDNA
      sequence of wild-type C1 endoglucanase 2 with D332E point
      mutation used as Round 1 backbone

<400> SEQUENCE: 2
atgattgtcg gcattctcac cacgctggct acgctggcca cactcgcagc tagtgtgcct      60
ctggaggagc ggcacgtgat gcaaagcggc ccctggcagc agtgcggagg aatcggatgg     120
cagggctcta ctgattgtgt ctctggatat cattgtgtgt atcaaaatga ctggtattcc     180
caatgtgtcc caggcgctgc atctaccact ttgcagacgt ctactacttc ccgtcccacc     240
gctacctcca ctgcccctcc aagcagcact acctcccctt ctaagggaaa gttgaagtgg     300
ttgggtagca acgagagcgg agctgagttc ggcgaaggaa actaccctgg cttgtggggc     360
aagcacttta tcttcccttc cacatctgcc atccagaccc ttatcaatga tggctacaac     420
atctttcgta tcgacttctc tatggaacgt ctggtcccga atcaattgac ttcttccttc     480
gacgagggct accttcgtaa cttgactgag gtggtcaatt ttgtcacaaa cgcgggaaag     540

```
tatgcggttc tggacccaca caactatggt cgttactatg gcaatgtgat tactgatacg    600
aacgccttcc gtacgttctg gaccaacttg gcaaagcagt tcgcttctaa ctctttggtc    660
attttcgaca caaataacga gtacaacact atggatcaga cccttgtgct taaccttaat    720
caagccgcca ttgatggaat tcgtgctgcg ggagccacca gccagtacat ttttgttgag    780
ggcaatgcct ggtctggagc gtggtcctgg aacaccacca cactaatat ggccgcgctt    840 acggaccctc agaacaagat tgtttatgag atgcatcaat atcttgacag cgacagctcc    900
ggtacccatg ccgagtgtgt cagctccaat atcggagcac agcgtgtcgt gggtgcgacg    960
cagtggctgc gtgcaaacgg taagctggga gttctgggcg agtttgcggg aggtgccaac   1020
gcagtgtgcc agcaggcggt cacgggattg cttgaccacc tgcaagacaa ttctgaggtg   1080
tggcttggag cactttggtg ggccgctggt ccctggtggg gtgactacat gtactccttt   1140
gagccgcctt ctggcaccgg atacgtgaac tacaactcca tcctgaagaa gtacttgccc   1200
taa                                                                 1203
```

<210> SEQ ID NO 3
<211> LENGTH: 400
<212> TYPE: PRT
<213> ORGANISM: Artificial Sequence
<220> FEATURE:
<223> OTHER INFORMATION: Synthetic polypeptide encoded by SEQ ID NO:2

<400> SEQUENCE: 3

```
Met Ile Val Gly Ile Leu Thr Thr Leu Ala Thr Leu Ala Thr Leu Ala
1               5                   10                  15

Ala Ser Val Pro Leu Glu Glu Arg His Val Met Gln Ser Gly Pro Trp
            20                  25                  30

Gln Gln Cys Gly Gly Ile Gly Trp Gln Gly Ser Thr Asp Cys Val Ser
        35                  40                  45

Gly Tyr His Cys Val Tyr Gln Asn Asp Trp Tyr Ser Gln Cys Val Pro
    50                  55                  60

Gly Ala Ala Ser Thr Thr Leu Gln Thr Ser Thr Thr Ser Arg Pro Thr
65                  70                  75                  80

Ala Thr Ser Thr Ala Pro Pro Ser Ser Thr Thr Ser Pro Ser Lys Gly
                85                  90                  95

Lys Leu Lys Trp Leu Gly Ser Asn Glu Ser Gly Ala Glu Phe Gly Glu
            100                 105                 110

Gly Asn Tyr Pro Gly Leu Trp Gly Lys His Phe Ile Phe Pro Ser Thr
        115                 120                 125

Ser Ala Ile Gln Thr Leu Ile Asn Asp Gly Tyr Asn Ile Phe Arg Ile
    130                 135                 140

Asp Phe Ser Met Glu Arg Leu Val Pro Asn Gln Leu Thr Ser Ser Phe
145                 150                 155                 160

Asp Glu Gly Tyr Leu Arg Asn Leu Thr Glu Val Val Asn Phe Val Thr
                165                 170                 175

Asn Ala Gly Lys Tyr Ala Val Leu Asp Pro His Asn Tyr Gly Arg Tyr
            180                 185                 190

Tyr Gly Asn Val Ile Thr Asp Thr Asn Ala Phe Arg Thr Phe Trp Thr
        195                 200                 205

Asn Leu Ala Lys Gln Phe Ala Ser Asn Ser Leu Val Ile Phe Asp Thr
    210                 215                 220

Asn Asn Glu Tyr Asn Thr Met Asp Gln Thr Leu Val Leu Asn Leu Asn
225                 230                 235                 240
```

```
Gln Ala Ala Ile Asp Gly Ile Arg Ala Ala Gly Ala Thr Ser Gln Tyr
            245                 250                 255

Ile Phe Val Glu Gly Asn Ala Trp Ser Gly Ala Trp Ser Trp Asn Thr
        260                 265                 270

Thr Asn Thr Asn Met Ala Ala Leu Thr Asp Pro Gln Asn Lys Ile Val
    275                 280                 285

Tyr Glu Met His Gln Tyr Leu Asp Ser Asp Ser Gly Thr His Ala
290                 295                 300

Glu Cys Val Ser Ser Asn Ile Gly Ala Gln Arg Val Val Gly Ala Thr
305                 310                 315                 320

Gln Trp Leu Arg Ala Asn Gly Lys Leu Gly Val Leu Gly Glu Phe Ala
            325                 330                 335

Gly Gly Ala Asn Ala Val Cys Gln Gln Ala Val Thr Gly Leu Leu Asp
        340                 345                 350

His Leu Gln Asp Asn Ser Glu Val Trp Leu Gly Ala Leu Trp Trp Ala
    355                 360                 365

Ala Gly Pro Trp Trp Gly Asp Tyr Met Tyr Ser Phe Glu Pro Pro Ser
370                 375                 380

Gly Thr Gly Tyr Val Asn Tyr Asn Ser Ile Leu Lys Lys Tyr Leu Pro
385                 390                 395                 400

<210> SEQ ID NO 4
<211> LENGTH: 1170
<212> TYPE: DNA
<213> ORGANISM: Myceliophthora thermophilia

<400> SEQUENCE: 4
atgaagtcct ccatcctcgc cagcgtcttc gccacgggcg ccgtggctca aagtggtccg      60
tggcagcaat gtggtggcat cggatggcaa ggatcgaccg actgtgtgtc gggttaccac     120
tgcgtctacc agaacgattg gtacagccag tgcgtgcctg cgcggcgtc gacaacgctc      180
cagacatcta ccacgtccag gcccaccgcc accagcaccg cccctccgtc gtccaccacc     240
tcgcctagca agggcaagct caagtggctc ggcagcaacg agtcgggcgc cgagttcggg     300
gagggcaact accccggcct ctggggcaag cacttcatct cccgtcgac ttcggcgatt       360
cagacgctca tcaatgatgg atacaacatc ttccggatcg acttctcgat ggagcgtctg     420
gtgcccaacc agttgacgtc gtccttcgac gagggctacc tccgcaacct gaccgaggtg     480
gtcaacttcg tgacgaacgc gggcaagtac gccgtcctgg acccgcacaa ctacggccgg     540
tactacggca acgtcatcac ggacacgaac gcgttccgga ccttctggac caacctggcc     600
aagcagttcg cctccaactc gctcgtcatc ttcgacacca caacgagta caacacgatg      660
gaccagaccc tggtgctcaa cctcaaccag gccgccatcg acggcatccg gccgccggc      720
gcgacctcgc agtacatctt cgtcgagggc aacgcgtgga gcggggcctg gagctggaac     780
acgaccaaca ccaacatggc cgccctgacg gaccgcaga acaagatcgt gtacgagatg      840
caccagtacc tcgactcgga cagctcgggc acccacgccg agtgcgtcag cagcaacatc     900
ggcgcccagc gcgtcgtcgg agccacccag tggctccgcg ccaacggcaa gctcggcgtc     960
ctcggcgagt tcgccggcgg cgccaacgcc gtctgccagc aggccgtcac cggcctcctc    1020
gaccacctcc aggacaacag cgacgtctgg ctgggtgccc tctggtgggc cgccggtccc    1080
tggtggggcg actacatgta ctcgttcgag cctccttcgg gcaccggcta tgtcaactac    1140
aactcgatcc taaagaagta cttgccgtaa                                     1170
```

```
<210> SEQ ID NO 5
<211> LENGTH: 389
<212> TYPE: PRT
<213> ORGANISM: Myceliophthora thermophilia

<400> SEQUENCE: 5
```

| | | | | | | | | | | | | | | | |
|---|---|---|---|---|---|---|---|---|---|---|---|---|---|---|---|
|Met|Lys|Ser|Ser|Ile|Leu|Ala|Ser|Val|Phe|Ala|Thr|Gly|Ala|Val|Ala|
|1| | | |5| | | | |10| | | | |15| |
|Gln|Ser|Gly|Pro|Trp|Gln|Gln|Cys|Gly|Gly|Ile|Gly|Trp|Gln|Gly|Ser|
| | | |20| | | | |25| | | | |30| | |
|Thr|Asp|Cys|Val|Ser|Gly|Tyr|His|Cys|Val|Tyr|Gln|Asn|Asp|Trp|Tyr|
| | | |35| | | | |40| | | | |45| | |
|Ser|Gln|Cys|Val|Pro|Gly|Ala|Ala|Ser|Thr|Thr|Leu|Gln|Thr|Ser|Thr|
| |50| | | | |55| | | | |60| | | | |
|Thr|Ser|Arg|Pro|Thr|Ala|Thr|Ser|Thr|Ala|Pro|Pro|Ser|Ser|Thr|Thr|
|65| | | | |70| | | | |75| | | | |80|
|Ser|Pro|Ser|Lys|Gly|Lys|Leu|Lys|Trp|Leu|Gly|Ser|Asn|Glu|Ser|Gly|
| | | | |85| | | | |90| | | | |95| |
|Ala|Glu|Phe|Gly|Glu|Gly|Asn|Tyr|Pro|Gly|Leu|Trp|Gly|Lys|His|Phe|
| | | |100| | | | |105| | | | |110| | |
|Ile|Phe|Pro|Ser|Thr|Ser|Ala|Ile|Gln|Thr|Leu|Ile|Asn|Asp|Gly|Tyr|
| | | |115| | | | |120| | | | |125| | |
|Asn|Ile|Phe|Arg|Ile|Asp|Phe|Ser|Met|Glu|Arg|Leu|Val|Pro|Asn|Gln|
| |130| | | | |135| | | | |140| | | | |
|Leu|Thr|Ser|Ser|Phe|Asp|Glu|Gly|Tyr|Leu|Arg|Asn|Leu|Thr|Glu|Val|
|145| | | | |150| | | | |155| | | | |160|
|Val|Asn|Phe|Val|Thr|Asn|Ala|Gly|Lys|Tyr|Ala|Val|Leu|Asp|Pro|His|
| | | | |165| | | | |170| | | | |175| |
|Asn|Tyr|Gly|Arg|Tyr|Tyr|Gly|Asn|Val|Ile|Thr|Asp|Thr|Asn|Ala|Phe|
| | | |180| | | | |185| | | | |190| | |
|Arg|Thr|Phe|Trp|Thr|Asn|Leu|Ala|Lys|Gln|Phe|Ala|Ser|Asn|Ser|Leu|
| | | |195| | | | |200| | | | |205| | |
|Val|Ile|Phe|Asp|Thr|Asn|Asn|Glu|Tyr|Asn|Thr|Met|Asp|Gln|Thr|Leu|
| |210| | | | |215| | | | |220| | | | |
|Val|Leu|Asn|Leu|Asn|Gln|Ala|Ala|Ile|Asp|Gly|Ile|Arg|Ala|Ala|Gly|
|225| | | | |230| | | | |235| | | | |240|
|Ala|Thr|Ser|Gln|Tyr|Ile|Phe|Val|Glu|Gly|Asn|Ala|Trp|Ser|Gly|Ala|
| | | | |245| | | | |250| | | | |255| |
|Trp|Ser|Trp|Asn|Thr|Thr|Asn|Thr|Asn|Met|Ala|Ala|Leu|Thr|Asp|Pro|
| | | |260| | | | |265| | | | |270| | |
|Gln|Asn|Lys|Ile|Val|Tyr|Glu|Met|His|Gln|Tyr|Leu|Asp|Ser|Asp|Ser|
| | | |275| | | | |280| | | | |285| | |
|Ser|Gly|Thr|His|Ala|Glu|Cys|Val|Ser|Ser|Asn|Ile|Gly|Ala|Gln|Arg|
| |290| | | | |295| | | | |300| | | | |
|Val|Val|Gly|Ala|Thr|Gln|Trp|Leu|Arg|Ala|Asn|Gly|Lys|Leu|Gly|Val|
|305| | | | |310| | | | |315| | | | |320|
|Leu|Gly|Glu|Phe|Ala|Gly|Gly|Ala|Asn|Ala|Val|Cys|Gln|Gln|Ala|Val|
| | | | |325| | | | |330| | | | |335| |
|Thr|Gly|Leu|Leu|Asp|His|Leu|Gln|Asp|Asn|Ser|Asp|Val|Trp|Leu|Gly|
| | | |340| | | | |345| | | | |350| | |
|Ala|Leu|Trp|Trp|Ala|Ala|Gly|Pro|Trp|Trp|Gly|Asp|Tyr|Met|Tyr|Ser|
| | | |355| | | | |360| | | | |365| | |
|Phe|Glu|Pro|Pro|Ser|Gly|Thr|Gly|Tyr|Val|Asn|Tyr|Asn|Ser|Ile|Leu|
| |370| | | | |375| | | | |380| | | | |

Lys Lys Tyr Leu Pro
385

<210> SEQ ID NO 6
<211> LENGTH: 1170
<212> TYPE: DNA
<213> ORGANISM: Artificial Sequence
<220> FEATURE:
<223> OTHER INFORMATION: Synthetic DNA which is cDNA of C1
      endoglucanase 2 variant 213

<400> SEQUENCE: 6

```
atgaagtcct ccatcctcgc cagcgtcttc gccacgggcg ccgtggctca aagtggtccg    60
tggcagcaat gtggtggcat cggatggcaa ggatcgaccg actgtgtgtc gggttaccac   120
tgcgtctacc agaacgattg gtacagccag tgcgtgcctg gcgcggcgtc gacaacgctc   180
cagacatcta ccacgtccag gcccaccgcc accagcaccc ccctccgtc gtccaccacc    240
tcgcctagca agggcaagtt caagtggctc ggcagcaacg agtcgggcgc cgagttcggg   300
gagggcaact accccggcct ctggggcaag cacttcatct cccgtcgac ttcggcgatt    360
cagacgctca tcaatgatgg atacaacatc ttccggatcc cgttctcgat ggagcgtctg   420
gtgcccaacc agttgacgtc gtccttcgac gagggctacc tccgcaacct gaccgaggtg   480
gtcaacttcg tgacgaacgc gggcaagtac gccgtcctgg acccgcacaa ctacggccgg   540
tactacggca acgtcatcac ggacacgaac gcgttccgga ccttctggac caacctggcc   600
aagcagttcg cctccaactc gctcgtcatc ttcgacacca caacgagta ccacacgatg    660
gaccagaccc tggtgctcaa cctcaaccag gccgccatcg acggcatccg ggccgccggc   720
gcgacctcgc agtacatctt cgtcgagggc aacgcgtgga gcggggcctg gacctggaac   780
acgaccaaca ccaacctcgc cgccctgacg gacccgcaga acaagatcgt gtacgagatg   840
caccagtacc tcgactcgga cagctcgggc acccacgccg agtgcgtcag cagcaacatc   900
ggcgcccagc gcgtcgtcgg agccacccag tggctccgcg ccaacggcaa gctcggcgtc   960
ctcggcgagt cgccggcgg cgccaacgcc gtctgccagc aggccgtcac cggcctcctc   1020
gaccacctcc aggacaacag cgacgtctgg ctgggtgccc tctggtgggc cgccggtccc   1080
tggtggggcg actacatgta ctcgttcgag cctccttcgg gcaccggcta tgtcaactac   1140
aactcgatcc taaagaagta cttgccgtaa                                    1170
```

<210> SEQ ID NO 7
<211> LENGTH: 389
<212> TYPE: PRT
<213> ORGANISM: Artificial Sequence
<220> FEATURE:
<223> OTHER INFORMATION: Synthetic polypeptide of C1 endoglucanase 2
      variant 213 with signal peptide

<400> SEQUENCE: 7

Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

```
Ser Pro Ser Lys Gly Lys Phe Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
            115                 120                 125

Asn Ile Phe Arg Ile Pro Phe Ser Met Glu Arg Leu Val Pro Asn Gln
        130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Val Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr His Thr Met Asp Gln Thr Leu
210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Thr Trp Asn Thr Thr Asn Thr Asn Leu Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Asn Ile Gly Ala Gln Arg
290                 295                 300

Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

Thr Gly Leu Leu Asp His Leu Gln Asp Asn Ser Asp Val Trp Leu Gly
            340                 345                 350

Ala Leu Trp Trp Ala Ala Gly Pro Trp Trp Gly Asp Tyr Met Tyr Ser
        355                 360                 365

Phe Glu Pro Pro Ser Gly Thr Gly Tyr Val Asn Tyr Asn Ser Ile Leu
370                 375                 380

Lys Lys Tyr Leu Pro
385

<210> SEQ ID NO 8
<211> LENGTH: 373
<212> TYPE: PRT
<213> ORGANISM: Artificial Sequence
<220> FEATURE:
<223> OTHER INFORMATION: Synthetic polypeptide of C1 endoglucanase 2
      variant 213 mature sequence lacking signal peptide

<400> SEQUENCE: 8

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
            20                  25                  30

Ser Gln Cys Val Pro Gly Ala Ala Ser Thr Thr Leu Gln Thr Ser Thr
```

```
           35                  40                  45
Thr Ser Arg Pro Thr Ala Thr Ser Thr Ala Pro Pro Ser Thr Thr
    50                  55                  60

Ser Pro Ser Lys Gly Lys Phe Lys Trp Leu Gly Ser Asn Glu Ser Gly
65                  70                  75                  80

Ala Glu Phe Gly Glu Gly Asn Tyr Pro Gly Leu Trp Gly Lys His Phe
                    85                  90                  95

Ile Phe Pro Ser Thr Ser Ala Ile Gln Thr Leu Ile Asn Asp Gly Tyr
                100                 105                 110

Asn Ile Phe Arg Ile Pro Phe Ser Met Glu Arg Leu Val Pro Asn Gln
            115                 120                 125

Leu Thr Ser Ser Phe Asp Glu Gly Tyr Leu Arg Asn Leu Thr Glu Val
    130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr His Thr Met Asp Gln Thr Leu
        195                 200                 205

Val Leu Asn Leu Asn Gln Ala Ala Ile Asp Gly Ile Arg Ala Ala Gly
    210                 215                 220

Ala Thr Ser Gln Tyr Ile Phe Val Glu Gly Asn Ala Trp Ser Gly Ala
225                 230                 235                 240

Trp Thr Trp Asn Thr Thr Asn Thr Asn Leu Ala Ala Leu Thr Asp Pro
                245                 250                 255

Gln Asn Lys Ile Val Tyr Glu Met His Gln Tyr Leu Asp Ser Asp Ser
                260                 265                 270

Ser Gly Thr His Ala Glu Cys Val Ser Ser Asn Ile Gly Ala Gln Arg
            275                 280                 285

Val Val Gly Ala Thr Gln Trp Leu Arg Ala Asn Gly Lys Leu Gly Val
    290                 295                 300

Leu Gly Glu Phe Ala Gly Gly Ala Asn Ala Val Cys Gln Gln Ala Val
305                 310                 315                 320

Thr Gly Leu Leu Asp His Leu Gln Asp Asn Ser Asp Val Trp Leu Gly
                325                 330                 335

Ala Leu Trp Trp Ala Ala Gly Pro Trp Trp Gly Asp Tyr Met Tyr Ser
                340                 345                 350

Phe Glu Pro Pro Ser Gly Thr Gly Tyr Val Asn Tyr Asn Ser Ile Leu
            355                 360                 365

Lys Lys Tyr Leu Pro
        370

<210> SEQ ID NO 9
<211> LENGTH: 1170
<212> TYPE: DNA
<213> ORGANISM: Artificial Sequence
<220> FEATURE:
<223> OTHER INFORMATION: Synthetic DNA which is cDNA encoding C1
      endoglucanase 2 variant 309

<400> SEQUENCE: 9
atgaagtcct ccatcctcgc cagcgtcttc gccacgggcg ccgtggctca aagtggtccg      60
tggcagcaat gtggtggcat cggatggcaa ggatcgaccg actgtgtgtc gggttaccac     120
```

```
tgcgtctacc agaacgattg gtacagccag tgcgtgcctg gcgcggcgtc gacaacgctc      180
cagacatcta ccacgtccag gcccaccgcc accagcaccg cccctccgtc gtccaccacc      240
tcgcctagca agggcaagtt caagtggctc ggcgtcaacg agtcgggcgc cgagttcggg      300
gagggcaact accccggcct ctggggcaag cacttcatct cccgtcgac ttcggcgatt        360 cagacgctca tcaatgatgg atacaacatc ttccggatcc cgttctcgat ggagcgtctg      420
gtgcccaacc agttgacgtc gtccttcgac gagggctacc tccgcaacct gaccgaggtg      480
gtcaacttcg tgacgaacgc gggcaagtac gccgtcctgg acccgcacaa ctacggccgg      540
tactacggca acgtcatcac ggacacgaac gcgttccgga ccttctggac caacctggcc      600
aagcagttcg cctccaactc gctcgtcatc ttcgacacca caacgagta ccacaacatg        660 gaccagaccc tggtgctcaa cctcaaccag gccgccatcg acggcatccg ggccgccggc      720
gcgacctcgc agtacatctt cgtcgagggc aacgcgtgga gcggggcctg gacctggaac      780
acgaccaaca ccaacctcgc cgccctgacg gacccgcaga acaagatcgt gtacgagatg      840
caccagtacc tcgactcgga cagctcgggc acccacgccg agtgcgtcag cagcaacatc      900
ggcgcccagc gcgtcgtcgg agccacccag tggctccgcg ccaacggcaa gctcggcgtc      960
ctcggcgagt tcgccggcgg cccgaacgcc gtctgccagc aggccgtcac cggcctcctc     1020
gaccacctcc aggacaacag cgacgtctgg ctgggtgccc tctggtgggc cgccggtccc     1080
tggtggggcg actacatgta ctcgttcgag cctccttcgg gcaccggcta tgtcaactac     1140
aactcgatcc taaagaagta cttgccgtaa                                      1170
```

<210> SEQ ID NO 10
<211> LENGTH: 389
<212> TYPE: PRT
<213> ORGANISM: Artificial Sequence
<220> FEATURE:
<223> OTHER INFORMATION: Synthetic polypeptide of C1 endoglucanase 2
      variant 309 sequence with signal peptide

<400> SEQUENCE: 10

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Phe Lys Trp Leu Gly Val Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Pro Phe Ser Met Glu Arg Leu Val Pro Asn Gln
    130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
```

165                 170                 175
Asn Tyr Gly Arg Tyr Tyr Gly Asn Val Ile Thr Asp Thr Asn Ala Phe
                180                 185                 190

Arg Thr Phe Trp Thr Asn Leu Ala Lys Gln Phe Ala Ser Asn Ser Leu
            195                 200                 205

Val Ile Phe Asp Thr Asn Asn Glu Tyr His Asn Met Asp Gln Thr Leu
        210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Thr Trp Asn Thr Thr Asn Thr Asn Leu Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Asn Ile Gly Ala Gln Arg
290                 295                 300

Val Val Gly Ala Thr Gln Trp Leu Arg Ala Asn Gly Lys Leu Gly Val
305                 310                 315                 320

Leu Gly Glu Phe Ala Gly Gly Pro Asn Ala Val Cys Gln Gln Ala Val
                325                 330                 335

Thr Gly Leu Leu Asp His Leu Gln Asp Asn Ser Asp Val Trp Leu Gly
            340                 345                 350

Ala Leu Trp Trp Ala Ala Gly Pro Trp Trp Gly Asp Tyr Met Tyr Ser
        355                 360                 365

Phe Glu Pro Pro Ser Gly Thr Gly Tyr Val Asn Tyr Asn Ser Ile Leu
    370                 375                 380

Lys Lys Tyr Leu Pro
385

<210> SEQ ID NO 11
<211> LENGTH: 373
<212> TYPE: PRT
<213> ORGANISM: Artificial Sequence
<220> FEATURE:
<223> OTHER INFORMATION: Synthetic polypeptide of C1 endoglucanase 2
      variant 309 mature sequence lacking signal peptide

<400> SEQUENCE: 11

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
                20                  25                  30

Ser Gln Cys Val Pro Gly Ala Ala Ser Thr Thr Leu Gln Thr Ser Thr
            35                  40                  45

Thr Ser Arg Pro Thr Ala Thr Ser Thr Ala Pro Pro Ser Ser Thr Thr
        50                  55                  60

Ser Pro Ser Lys Gly Lys Phe Lys Trp Leu Gly Val Asn Glu Ser Gly
65                  70                  75                  80

Ala Glu Phe Gly Glu Gly Asn Tyr Pro Gly Leu Trp Gly Lys His Phe
                85                  90                  95

Ile Phe Pro Ser Thr Ser Ala Ile Gln Thr Leu Ile Asn Asp Gly Tyr
            100                 105                 110

Asn Ile Phe Arg Ile Pro Phe Ser Met Glu Arg Leu Val Pro Asn Gln
        115                 120                 125

Leu Thr Ser Ser Phe Asp Glu Gly Tyr Leu Arg Asn Leu Thr Glu Val
130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
            165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr His Asn Met Asp Gln Thr Leu
            195                 200                 205

Val Leu Asn Leu Asn Gln Ala Ala Ile Asp Gly Ile Arg Ala Ala Gly
210                 215                 220

Ala Thr Ser Gln Tyr Ile Phe Val Glu Gly Asn Ala Trp Ser Gly Ala
225                 230                 235                 240

Trp Thr Trp Asn Thr Thr Asn Thr Asn Leu Ala Ala Leu Thr Asp Pro
            245                 250                 255

Gln Asn Lys Ile Val Tyr Glu Met His Gln Tyr Leu Asp Ser Asp Ser
            260                 265                 270

Ser Gly Thr His Ala Glu Cys Val Ser Ser Asn Ile Gly Ala Gln Arg
            275                 280                 285

Val Val Gly Ala Thr Gln Trp Leu Arg Ala Asn Gly Lys Leu Gly Val
290                 295                 300

Leu Gly Glu Phe Ala Gly Gly Pro Asn Ala Val Cys Gln Gln Ala Val
305                 310                 315                 320

Thr Gly Leu Leu Asp His Leu Gln Asp Asn Ser Asp Val Trp Leu Gly
            325                 330                 335

Ala Leu Trp Trp Ala Ala Gly Pro Trp Trp Gly Asp Tyr Met Tyr Ser
            340                 345                 350

Phe Glu Pro Pro Ser Gly Thr Gly Tyr Val Asn Tyr Asn Ser Ile Leu
            355                 360                 365

Lys Lys Tyr Leu Pro
            370

<210> SEQ ID NO 12
<211> LENGTH: 373
<212> TYPE: PRT
<213> ORGANISM: Artificial Sequence
<220> FEATURE:
<223> OTHER INFORMATION: Synthetic polypeptide of C1 endoglucanase 2
      variant 372 mature polypeptide lacking signal peptide

<400> SEQUENCE: 12

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
            20                  25                  30

Ser Gln Cys Val Pro Gly Ala Ala Ser Thr Thr Leu Gln Thr Ser Thr
            35                  40                  45

Thr Ser Arg Pro Thr Ala Thr Ser Thr Ala Pro Pro Ser Ser Thr Thr
50                  55                  60

Ser Pro Ser Lys Gly Lys Phe Lys Trp Leu Gly Val Asn Glu Ser Gly
65                  70                  75                  80

Ala Glu Phe Gly Glu Gly Asn Tyr Pro Gly Leu Trp Gly Lys Asp Phe
                85                  90                  95

Ile Phe Pro Ser Thr Ser Ala Ile Gln Thr Leu Ile Asn Asp Gly Tyr
            100                 105                 110

```
Asn Ile Phe Arg Ile Pro Phe Ser Met Glu Arg Leu Val Pro Asn Gln
        115                 120                 125

Leu Thr Ser Ser Phe Trp Glu Gly Tyr Leu Arg Asn Leu Thr Glu Val
    130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr His Asn Met Asp Gln Thr Leu
        195                 200                 205

Val Leu Asn Leu Asn Gln Ala Ala Ile Asp Gly Ile Arg Ala Ala Gly
    210                 215                 220

Ala Thr Ser Gln Tyr Ile Phe Val Glu Gly Asn Ala Trp Ser Gly Ala
225                 230                 235                 240

Trp Thr Trp Asn Thr Thr Asn Thr Asn Leu Ala Ala Leu Thr Asp Pro
                245                 250                 255

Gln Asn Lys Ile Val Tyr Glu Met His Gln Tyr Leu Asp Ser Asp Ser
            260                 265                 270

Ser Gly Thr His Ala Glu Cys Val Ser Ser Asn Ile Gly Ala Gln Arg
        275                 280                 285

Val Val Gly Ala Thr Gln Trp Leu Arg Ala Asn Gly Lys Leu Gly Val
    290                 295                 300

Leu Gly Glu Phe Ala Gly Gly Pro Asn Ala Val Cys Gln Gln Ala Val
305                 310                 315                 320

Thr Gly Leu Leu Asp His Leu Gln Asp Asn Ser Asp Val Trp Leu Gly
                325                 330                 335

Ala Leu Trp Trp Ala Ala Gly Pro Trp Trp Gly Asp Tyr Met Phe Ser
            340                 345                 350

Phe Glu Pro Pro Ser Gly Thr Ala Tyr Val Asn Tyr Asn Pro Ile Leu
        355                 360                 365

Lys Lys Tyr Leu Pro
        370

<210> SEQ ID NO 13
<211> LENGTH: 373
<212> TYPE: PRT
<213> ORGANISM: Artificial Sequence
<220> FEATURE:
<223> OTHER INFORMATION: Synthetic polypeptide of C1 endoglucanase 2
      variant 443 mature polypeptide lacking signal peptide

<400> SEQUENCE: 13

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
                20                  25                  30

Ser Gln Cys Val Pro Gly Ala Ala Ser Thr Thr Leu Gln Thr Ser Thr
            35                  40                  45

Thr Ser Arg Pro Thr Ala Thr Ser Thr Ala Pro Pro Ser Ser Thr Thr
        50                  55                  60

Ser Pro Ser Lys Gly Lys Phe Lys Trp Leu Gly Val Asn Glu Ser Gly
65                  70                  75                  80

Ala Glu Phe Gly Glu Gly Asn Tyr Pro Gly Leu Trp Gly Lys Asp Phe
```

-continued

```
                         85                    90                    95
Ile Phe Pro Ser Thr Ser Ala Ile Gln Thr Leu Ile Asn Asp Gly Tyr
            100                   105                   110

Asn Ile Phe Arg Ile Pro Phe Ser Met Glu Arg Leu Val Pro Asn Gln
            115                   120                   125

Leu Thr Ser Ser Phe Trp Glu Gly Tyr Leu Arg Asn Leu Thr Glu Val
            130                   135                   140

Val Asn Phe Val Thr Asn Ala Gly Lys Tyr Ala Val Leu Asp Pro His
145                   150                   155                   160

Asn Tyr Gly Arg Tyr Tyr Gly Asn Val Ile Thr Asp Thr Asn Ala Phe
                165                   170                   175

Arg Thr Phe Trp Thr Asn Leu Ala Lys Gln Phe Ala Ser Asn Ser Leu
            180                   185                   190

Val Ile Phe Asp Thr Asn Asn Glu Tyr His Asn Met Asp Gln Thr Leu
            195                   200                   205

Val Leu Asn Leu Asn Gln Ala Ala Ile Asp Gly Ile Arg Ala Ala Gly
210                   215                   220

Ala Thr Ser Gln Tyr Ile Phe Val Glu Gly Asn Ala Trp Ser Gly Ala
225                   230                   235                   240

Trp Thr Trp Asn Thr Thr Asn Thr Asn Leu Ala Ala Leu Thr Asp Pro
                245                   250                   255

Gln Asn Lys Ile Val Tyr Glu Met His Gln Tyr Leu Asp Ser Asp Ser
                260                   265                   270

Ser Gly Thr His Ala Glu Cys Val Ser Ser Asn Ile Gly Ala Gln Arg
            275                   280                   285

Val Val Gly Ala Thr Gln Trp Leu Arg Ala Asn Gly Lys Leu Gly Val
290                   295                   300

Leu Gly Glu Phe Ala Gly Gly Pro Asn Ala Val Cys Gln Gln Ala Val
305                   310                   315                   320

Thr Gly Leu Leu Asp His Leu Gln Asp Asn Ser Asp Val Trp Leu Gly
                325                   330                   335

Ala Leu Trp Trp Ala Ala Gly Pro Trp Trp Gly Asp Tyr Met Phe Ser
            340                   345                   350

Phe Glu Pro Pro Ser Gly Thr Gly Tyr Val Asn Tyr Asn Pro Ile Leu
            355                   360                   365

Lys Lys Tyr Leu Pro
370
```

US 9,512,416 B2

ENDOGLUCANASE VARIANTS

CROSS-REFERENCE TO RELATED APPLICATIONS

This application is a divisional of application Ser. No. 13/332,114 filed Dec. 20, 2011, which claims priority to U.S. provisional application No. 61/425,733 filed Dec. 21, 2010, each of which applications is incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

This application includes a Sequence Listing as a text file named "90834-004120US-924289_SEQ" created Nov. 14, 2014 and containing 38,024 bytes. The material contained in this text file is incorporated by reference in its entirety for all purposes.

FIELD OF THE INVENTION

This invention relates to variant endoglucanase polypeptides and their use in production of soluble sugars from cellulosic biomass.

BACKGROUND OF THE INVENTION

Cellulosic biomass is a significant renewable resource for the generation of soluble sugars. These sugars can be used as reactants in various metabolic processes, including fermentation, to produce biofuels, chemical compounds, and other commercially valuable products. While the fermentation of simple sugars such as glucose to ethanol is relatively straightforward, the efficient conversion of cellulosic biomass to soluble sugars is challenging (see, e.g., Ladisch et al., 1983, *Enzyme Microb. Technol.* 5:82). Cellulose may be pretreated chemically, mechanically, enzymatically or in other ways to increase the susceptibility of cellulose to hydrolysis. Such pretreatment may be followed by the enzymatic conversion of cellulose to cellobiose, cello-oligosaccharides, glucose, and other sugars and sugar polymers, using enzymes that break down the β-1-4 glycosidic bonds of cellulose. These enzymes are collectively referred to as "cellulases."

Cellulases are divided into three sub-categories of enzymes: 1,4-β-D-glucan glucanohydrolase ("endoglucanase" or "EG"); 1,4-β-D-glucan cellobiohydrolase ("exoglucanase," "cellobiohydrolase," or "CBH"); and β-D-glucoside-glucohydrolase ("β-glucosidase," "cellobiase," or "BG"). See Methods in Enzymology, 1988, Vol. 160, p. 200-391 (Eds. Wood, W. A. and Kellogg, S. T.). These enzymes act in concert to catalyze the hydrolysis of cellulose containing substrates. Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers.

Cellulases with improved properties for use in processing cellulosic biomass would reduce costs and increase the efficiency of production of biofuels and other commercially valuable compounds.

BRIEF SUMMARY OF THE INVENTION

In one aspect, the present invention provides isolated endoglucanase variants that exhibit improved properties. In some embodiments, the endoglucanase variants are superior to naturally occurring endoglucanases under conditions required for saccharification of cellulosic biomass.

In some embodiments, an isolated endoglucanase variant comprises an amino acid sequence having substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to a wild-type endoglucanase 2 (e.g., SEQ ID NO:1), and comprises at least one amino acid substitution at one or more of the amino acid residues selected from residues at amino acid position 1, 5, 12, 18, 27, 45, 48, 49, 51, 50, 54, 56, 61, 70, 71, 72, 76, 82, 85, 86, 87, 91, 94, 95, 96, 101, 106, 112, 117, 118, 127, 128, 131, 133, 134, 135, 143, 145, 146, 147, 150, 151, 153, 155, 167, 169, 173, 174, 177, 186, 190, 191, 202, 203, 205, 207, 210, 211, 224, 226, 232, 236, 240, 242, 245, 248, 250, 254, 256, 257, 264, 270, 272, 276, 277, 282, 283, 286, 287, 289, 290, 298, 299, 300, 302, 304, 312, 314, 321, 323, 325, 326, 328, 330, 338, 351, 357, 358, 359, 360, 363, 366, and 367, wherein the residues are numbered with reference to SEQ ID NO:1.

In some embodiments, an isolated endoglucanase variant comprises an amino acid sequence having substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to a wild-type endoglucanase 2 (e.g., SEQ ID NO:1), and comprises at least one amino acid substitution at one or more of the amino acid residues selected from Q1, W5, G12, D18, Y27, Q45, T48, T49, R51, S50, A54, S56, S61, K70, L71, K72, S76, E82, E85, G86, N87, L91, K94, H95, F96, T101, T106, Y112, I117, D118, N127, Q128, S131, F133, D134, E135, E143, V145, N146, F147, N150, A151, K153, A155, G167, V169, T173, N174, R177, Q186, N190, S191, N202, T203, D205, T207, L210, N211, G224, T226, V232, A236, A240, S242, T245, T248, M250, T254, P256, Q257, M264, S270, S272, H276, A277, S282, N283, A286, Q287, V289, V290, A298, N299, G300, L302, V304, A312, A314, T321, L323, D325, H326, Q328, N330, L338, Y351, S357, G358, T359, G360, N363, S366, and I367, wherein the residues are numbered with reference to SEQ ID NO:1.

In some embodiments, the isolated endoglucanase variant comprises one or more amino acid substitutions selected from Q1S, W5M, G12E, D18Q, Y27R, Q45R, T48V, T49R, R51L, S50P, A54C, S56L, S61E, K70C/R, L71F, K72E/H, S76A/M/V, E82K, E85A/D, G86P, N87C, L91M, K94E/I, H95D, F96Y, T101C/P, T106A, Y112M, I117V, D118A/C/G/P/S/T/Y, N127H, Q128T, S131A/C/G, F133P, D134E/G/H/Q/R/S/T/W/Y, E135P/Q, E143H/T, V145C, N146D/E/Q/R, F147C/Y, N150D/R, A151Q/R/Y, K153Q, A155C, G167D, V169I, T173P, N174D/L/S, R177M, Q186E, N190Q/S/V, S191P, N202H, T203D/H/K/N/R/S, D205P, T207D, L210P, N211A, G224D, T226G, V232I, A236C/G, A240C, S242C/T, T245Q/V, T248N/Q, M250L, T254M/V, P256R, Q257E/M/S, M264C, S270E, S272G, H276S, A277P, S282A/E/G, N283T, A286E/K/L/V/Q, Q287E, V289L, V290E/R/S/W/Y, A298D/E, N299K, G300H, L302K/M, V304F, A312P, A314T, T321Q, L323M, D325N, H326Y, Q328C, N330H, L338F, Y351F, S357C, G358S, T359K, G360A, N363H, S366A/C/N/P, and I367L/M, wherein the residues are numbered with reference to SEQ ID NO:1.

In another aspect, the present invention provides polynucleotides encoding endoglucanase variants that exhibit improved properties. In some embodiments, the polypeptide encodes an amino acid sequence with improved properties and substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to a wild-type endoglucanase 2 (e.g., SEQ ID NO:1), and comprising at least one amino acid substitution at one or more amino acid residue selected from 1, 5, 12, 18, 27, 45, 48, 49, 51, 50, 54, 56, 61, 70, 71, 72, 76, 82, 85, 86, 87, 91, 94, 95, 96, 101, 106, 112, 117, 118, 127, 128, 131, 133, 134, 135, 143, 145, 146, 147, 150, 151, 153, 155, 167, 169, 173, 174, 177, 186, 190, 191, 202, 203, 205, 207, 210, 211, 224, 226, 232, 236, 240, 242, 245, 248, 250, 254, 256, 257, 264, 270, 272, 276, 277, 282, 283, 286, 287, 289, 290, 298, 299, 300, 302, 304, 312, 314, 321, 323, 325, 326, 328, 330, 338, 351, 357, 358, 359, 360, 363, 366, and 367, wherein the residues are numbered with reference to SEQ ID NO:1.

In a related aspect, the present invention provides a recombinant polynucleotide substantially identical to SEQ ID NO:4 that comprises at least one mutation at at least one position selected from 84, 111, 123, 135, 153, 159, 204, 225, 315, 318, 360, 393, 423, 447, 471, 522, 534, 642, 661, 684, 735, 762, 738, 768, 802, 837, 933, and/or 960, wherein said polynucleotide is numbered in accordance with SEQ ID NO:4. In some embodiments the recombinant polynucleotide comprises at least one substitution selected from t84, t111, g123, g135, g153, c159, g204, c225, g315, g318, g360, g393, g423, a447, g471, c522, g534, g642, c661, g684, g735, g762, c738, g768, c802, c837, c933, and/or c960, wherein said polynucleotide is numbered in accordance with SEQ ID NO:4. In some embodiments the recombinant polynucleotide comprises at least one substitution selected from t84a, t111c, g123a, g135a, g153a, c159t, g204a, c225t, g315a, g318a, g360a, g393a, g423t, a447g, g471a, c522t, g534a, g642a, c661a, g684a, g735c, g762c, c738t, g768t, c802t, c837t, c933t, and/or c960t, wherein said polynucleotide is numbered in accordance with SEQ ID NO:4. Also provided are an expression vector comprising at least one aforementioned polynucleotide, or a host cell comprising the at least one aforementioned polynucleotide. Also provided are polynucleotides encoding each of the individual variant polypeptide set forth in Tables 2, 3, 4 or 5.

In another aspect, the present invention provides polynucleotides encoding endoglucanase variants that exhibit improved properties. In some embodiments, the polypeptide encodes an amino acid sequence with improved properties and substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to a wild-type endoglucanase 2 (e.g., SEQ ID NO:1), and comprising at least one amino acid substitution at one or more amino acid residues selected from Q1, W5, G12, D18, Y27, Q45, T48, T49, R51, S50, A54, S56, S61, K70, L71, K72, S76, E82, E85, G86, N87, L91, K94, H95, F96, T101, T106, Y112, I117, D118, N127, Q128, S131, F133, D134, E135, E143, V145, N146, F147, N150, A151, K153, A155, G167, V169, T173, N174, R177, Q186, N190, S191, N202, T203, D205, T207, L210, N211, G224, T226, V232, A236, A240, S242, T245, T248, M250, T254, P256, Q257, M264, S270, S272, H276, A277, S282, N283, A286, Q287, V289, V290, A298, N299, G300, L302, V304, A312, A314, T321, L323, D325, H326, Q328, N330, L338, Y351, S357, G358, T359, G360, N363, S366, and I367, wherein the residues are numbered with reference to SEQ ID NO:1.

In some embodiments, the polynucleotide encodes an endoglucanase variant comprises one or more amino acid substitutions selected from Q1S, W5M, G12E, D18Q, Y27R, Q45R, T48V, T49R, R51L, S50P, A54C, S56L, S61E, K70C/R, L71F, K72E/H, S76A/M/V, E82K, E85A/D, G86P, N87C, L91M, K94E/I, H95D, F96Y, T101C/P, T106A, Y112M, I117V, D118A/C/G/P/S/T/N, N127H, Q128T, S131A/C/G, F133P, D134E/G/H/Q/R/S/T/W/Y, E135P/Q, E143H/T, V145C, N146D/E/Q/R, F147C/Y, N150D/R, A151Q/R/Y, K153Q, A155C, G167D, V169I, T173P, N174D/L/S, R177M, Q186E, N190Q/S/V, S191P, N202H, T203D/H/K/N/R/S, D205P, T207D, L210P, N211A, G224D, T226G, V232I, A236C/G, A240C, S242C/T, T245Q/V, T248N/Q, M250L, T254M/V, P256R, Q257E/M/S, M264C, S270E, S272G, H276S, A277P, S282A/E/G, N283T, A286E/K/L/V/Q, Q287E, V289L, V290E/R/S/W/Y, A298D/E, N299K, G300H, L302K/M, V304F, A312P, A314T, T321Q, L323M, D325N, H326Y, Q328C, N330H, L338F, Y351F, S357C, G358S, T359K, G360A, N363H, S366A/C/N/P, and I367L/M, wherein the residues are numbered with reference to SEQ ID NO:1.

In some embodiments, the endoglucanase variant (having a sequence comprising one or more substitutions as disclosed herein) exhibits increased thermoactivity and/or thermostability at low pH (e.g., pH 3.5-5) and high temperature (e.g., 65-80° C.) in comparison to a wild-type *Myceliophthora thermophila* endoglucanase of SEQ ID NO:1. In some embodiments, the endoglucanase variant exhibits increased thermoactivity and/or thermostability at pH about 4-5 and about 65-75° C. in comparison to a wild-type *Myceliophthora thermophila* endoglucanase of SEQ ID NO:1. In some embodiments, the endoglucanase variant exhibits increased viscosity reduction activity at low pH (e.g., in the range of pH 3-5, such as pH 3.5) and high temperature (e.g., in the range of 65-80° C., such as about 80° C.) in comparison to a wild-type *Myceliophthora thermophila* endoglucanase of SEQ ID NO:1.

In some embodiments, the endoglucanase is *Myceliophthora thermophila* endoglucanase 2. In some further embodiments, the endoglucanase is a C1 endoglucanase 2.

In some embodiments, the endoglucanase variant is derived from, and has improved thermoactivity, thermostability, and/or viscosity reduction activity relative to an endoglucanase homolog of SEQ ID NO:1.

In still another aspect, the present invention provides vectors comprising at least one polynucleotide as described herein. In some embodiments, the vectors comprise at least one polynucleotide encoding at least one endoglucanase variant as provided herein. In some additional embodiments, the vectors further comprise at least one polynucleotide encoding at least one additional enzyme (e.g., cellulase).

In yet another aspect, the present invention provides host cells transformed with at least one polynucleotide or vector encoding at least one endoglucanase variant as described herein. In some further embodiments, the host cells are transformed with at least one polynucleotide or vector encoding at least one additional enzyme (e.g., cellulase).

In still another aspect, the present invention provides methods of producing an endoglucanase variant comprising culturing a host cell transformed with a polynucleotide or vector encoding an endoglucanase variant as described herein under conditions suitable for the production of the endoglucanase variant by the cell. In some embodiments, the endoglucanase variant polypeptide is secreted by the cell and obtained from the cell culture medium.

In still another aspect, the present invention provides enzyme compositions comprising at least one recombinant or isolated endoglucanase variant polypeptide as described herein. In some embodiments, the enzyme composition is used in a composition for a saccharification reaction. In some embodiments, the enzyme compositions comprising at least one variant endoglucanase of the invention comprise at least one other enzyme (e.g. one or more other cellulases).

In yet another aspect, the present invention provides methods of producing at least one soluble sugar, comprising contacting a cellulosic substrate with a cellobiohydrolase, a β-glucosidase, and an endoglucanase variant as described herein under conditions in which at least one soluble sugar is produced.

In still another aspect, the present invention provides a method of producing cellodextrin molecules from a cellulosic substrate, comprising contacting the cellulosic substrate with an endoglucanase variant as described herein under conditions in which the cellodextrin molecules are produced.

In yet another aspect, the present invention provides a method of producing an end-product from a cellulosic substrate, comprising (a) contacting the cellulosic substrate with at least one cellobiohydrolase, at least one β-glucosidase, and at least one endoglucanase variant as described herein under conditions in which soluble sugars are produced; and (b) contacting the soluble sugars with a microorganism in a fermentation to produce the end-product. In some embodiments, the end-product comprises at lease one alcohol, fatty acid, lactic acid, acetic acid, 3-hydroxypropionic acid, acrylic acid, succinic acid, citric acid, malic acid, fumaric acid, succinic acid, amino acid, 1,3-propanediol, ethylene, glycerol, or β-lactam or combinations thereof. In some embodiments, the end-product is an alcohol (e.g., ethanol or butanol). In some embodiments, the microorganism is a yeast. In some embodiments, the fermentation is a simultaneous saccharification and fermentation process. In some embodiments, the saccharification and fermentation steps are consecutive.

DEFINITIONS

Figure 1:
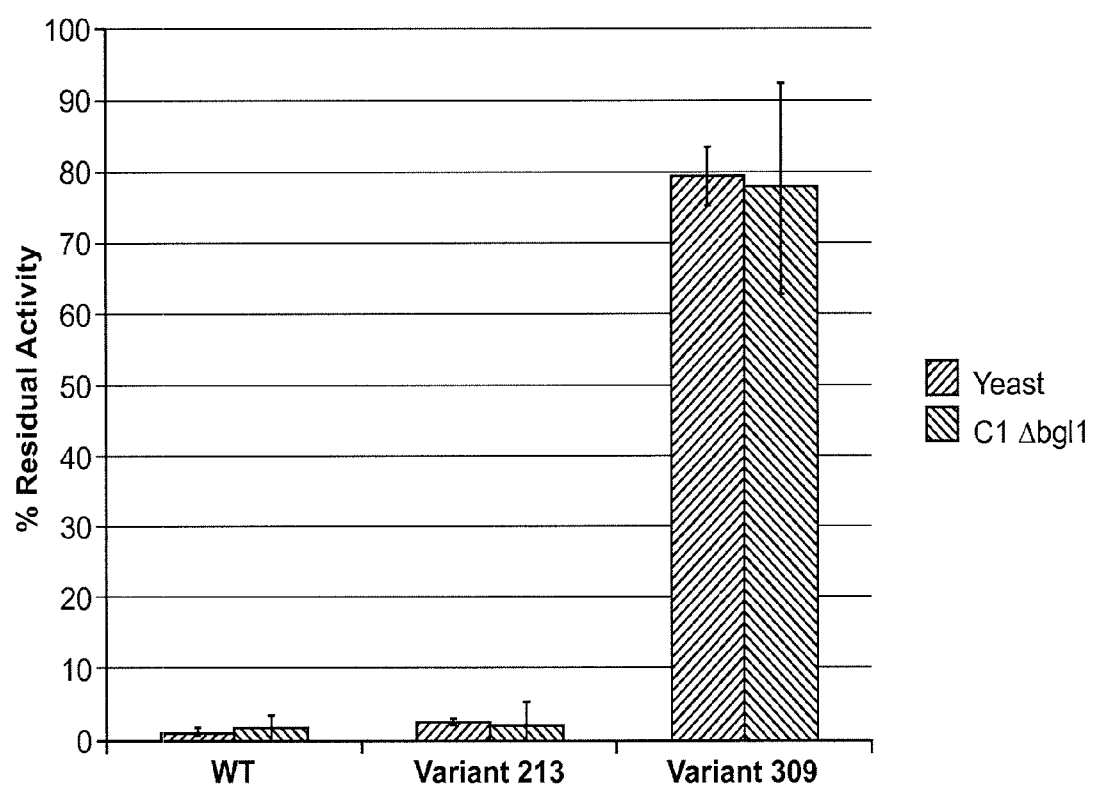
FIG. 1 shows the residual activity of endoglucanase variant 213 and variant 309 expressed in yeast and in a C1-derived lab strain, C1 Δbgl1, after 1 hr of pre-incubation at pH 4.0, 75° C. as determined by an AVICEL® cellulose assay. N=10-48, error bars represent ±1 SD.

Unless defined otherwise, all technical and scientific terms used herein generally have the same meaning as commonly understood by one of ordinary skill in the art to which this invention belongs. Generally, the nomenclature used herein and the laboratory procedures in analytical chemistry, cell culture, molecular genetics, organic chemistry and nucleic acid chemistry and hybridization described below are those well known and commonly employed in the art. As used herein, "a," "an," and "the" include plural references unless the context clearly dictates otherwise.

The terms "biomass," "biomass substrate," "cellulosic biomass," or "cellulosic substrate" refer to materials that contain cellulose. Examples of biomass substrates include, but are not limited to, wood, wood pulp, paper pulp, corn fiber, corn grain, corn cobs, sugar cane, sugar beet, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, *miscanthus*, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments, the biomass comprises a mixture of fibers that originate from different biomasses. In some embodiments, the biomass may also comprise transgenic plants that express ligninase and/or cellulase enzymes (See e.g., US 2008/0104724 A1). In some embodiments, the biomass substrate is "pretreated," or treated using methods known in the art.

In some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of ligninsolubilizing microorganisms) and combinations thereof, to increase the susceptibility of cellulose to hydrolysis. In some embodiments, biomass includes cellulosic substrates that contain cellulose, hemicellulose, and/or lignocellulose.

In some embodiments, pretreatment is carried out to hydrolyze hemicellulose, and/or a portion thereof present in the cellulosic substrate to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the cellulosic substrate. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of biomass substrates (See e.g., U.S. Pat. No. 4,461,648). Another method of pretreating the slurry involves continuous pretreatment (e.g., the cellulosic biomass is pumped though a reactor continuously). Pretreatment methods are well-known to those skilled in the art (See e.g., U.S. Pat. Nos. 4,461,648; 7,754,457; 5,171,592; 5,037,663; 4,600,590; 6,106,888; 4,356,196; 5,939,544; 6,176,176; 5,037,663; 5,171,592; 4,556,430; and 7,465,791; and WO2009/045651 and US 2007/0031953; and Weil et al. (1997) Appl. Biochem. Biotechnol., 68:21-40, each of which is incorporated herein by reference).

"Saccharification" refers to the process in which substrates (e.g., cellulosic biomass) are broken down via the action of cellulases to produce fermentable sugars (e.g. monosaccharides such as but not limited to glucose). "Saccharification" also refers to the process in which cellulosic substrates are hydrolyzed to produce soluble sugars (e.g., glucose and cellobiose).

"Fermentable sugars" means simple sugars (monosaccharides, disaccharides and short oligosaccharides) such as but not limited to glucose, xylose, galactose, arabinose, mannose and sucrose.

As used herein the term "soluble sugars" refers to water-soluble hexose monomers and oligomers of up to about six monomer units. In some embodiments, the term refers to cellobiose and glucose.

The term "cellodextrin" refers to a glucose polymer of varying length (e.g., comprising at least two glucose monomers). Each glucose monomer is linked via a beta-1,4 glycosidic bond. A cellodextrin is classified by its degree of polymerization (DP), which indicates the number of glucose monomers the cellodextrin contains. The most common cellodextrins are: cellobiose (DP=2); cellotriose (DP=3); cellotetrose (DP=4); cellopentose (DP=5); and cellohexose (DP=6). In some embodiments, cellodextrins have a DP of 2-6 (e.g., cellobiose, cellotriose, cellotetrose, cellopentose, and/or cellohexose). In some embodiments, cellodextrins have a DP greater than 6. The degree of polymerization of cellodextin molecules can be measured, e.g., by mass spectrometry, including but not limited to matrix-assisted laser desorption/ionization (MALDI) mass spectrometry and electrospray ionization ion trap (ESI-IT) mass spectrometry. Methods of measuring the degree of polymerization of cellodextrin molecules are known in the art; see, e.g., Melander et al., *Biomacromolecules* 7:1410-1421 (2006).

As used herein, the term "fermentation" is used broadly to refer to the cultivation of a microorganism(s) that use simple sugars, such as fermentable or soluble sugars, as an energy source to produce a desired end-product.

As used herein, the term "cellulase" refers to a category of enzymes capable of hydrolyzing cellulose (β-1,4-glucan or β-D-glucosidic linkages) to shorter cellulose chains, oligosaccharides, cellobiose and/or glucose.

As used herein, the term "endoglucanase" or "EG" refers to a class of cellulases (E.C.3.2.1.4) that hydrolyze internal β-1,4 glucosidic linkages in cellulose.

As used herein, the term "cellobiohydrolase" or "CBH" refers to a category of cellulases (EC 3.2.1.91) that hydrolyze glycosidic bonds in cellulose.

As used herein, the term "β-glucosidase," "cellobiase," or "BGL" refers to a category of cellulases (EC 3.2.1.21) that catalyze the hydrolysis of cellobiose to glucose.

As used herein, the term "C1" refers to a fungal strain described by Garg, A., 1966, "An addition to the genus *Chrysosporium corda*" *Mycopathologia* 30: 3-4. "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/ 0099079; International Pat. Pub. Nos., WO 2008/073914 and WO 98/15633, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophilia*. Other C1 strains and/or C1-derived strains include cells deposited under accession numbers ATCC 44006 and PTA-12255, CBS (Centraalbureau voor Schimmelcultures) 122188, CBS 251.72, CBS 143.77, CBS 272.77, and VKM F-3500D. Exemplary C1 derivatives include modified organisms in which one or more endogenous genes or sequences have been deleted or modified and/or one or more heterologous genes or sequences have been introduced. Derivatives include UV18#100f Δalpl, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO2008073914 and WO2010107303, each of which is incorporated herein by reference.

As used herein, the term "wild-type M. thermophila endoglucanase" refers to SEQ ID NO:1, the mature peptide sequence (i.e., lacking a signal peptide) of endoglucanase 2 that is expressed by the naturally occurring *M. thermophila* (e.g., strain C1).

As used herein, the term "variant" refers to an endoglucanase polypeptide or polynucleotide encoding an endoglucanase polypeptide comprising one or more modifications relative to wild-type *M. thermophila* endoglucanase (or other specified reference protein) or the wild-type polynucleotide (or other specified reference sequence) such as substitutions, insertions, deletions, and/or truncations of one or more specific amino acid residues or of one or more specific nucleotides or codons in the polypeptide or polynucleotide.

The term "biologically active" or "functional" as used herein in the context of endoglucanase, refers to homolog, variant, or fragment of wild-type EG protein (or other reference protein) that has endoglucanase activity. In some embodiments the biologically active variant has improved properties compared to the wild-type or reference EG protein.

As used herein, the term "endoglucanase polypeptide" refers to a polypeptide having endoglucanase activity.

As used herein, the term "endoglucanase polynucleotide" refers to a polynucleotide encoding a polypeptide having endoglucanase activity.

The terms "improved" and "improved properties," as used in the context of describing the properties of an endoglucanase variant, refer to an endoglucanase variant polypeptide that exhibits an improvement in any property as compared to the wild-type *M. thermophila* endoglucanase 2 (SEQ ID NO:1). Improved properties may include, but are not limited to increased protein expression, improved thermoactivity, improved thermostability, improved pH activity, improved pH stability, improved viscosity reduction, improved product specificity, increased specific activity, improved substrate specificity, increased resistance to substrate or end-product inhibition, altered pH/temperature profile, and/or improved chemical stability.

As used herein, the phrases "improved thermoactivity" and "increased thermoactivity" refer to a variant enzyme displaying an increase, relative to a reference sequence (e.g., a wild-type endoglucanase), in the amount of endoglucanase enzymatic activity (e.g., substrate hydrolysis) in a specified time under specified reaction conditions. Exemplary methods for measuring endoglucanase activity are provided in the Examples and include, but are not limited to, measuring cellobiose production from crystalline cellulose as measured by HTP screening or HPLC.

As used herein, the phrases "improved thermostability" and "increased thermostability" refer to a variant enzyme displaying an increase in "residual activity" relative to the wild-type enzyme. Residual activity is determined by exposing the variant enzyme and the reference (e.g., wild-type) enzyme to stress conditions of elevated temperature for a period of time and then determining endoglucanase activity under conditions in which wild-type enzyme normally has activity. For example, the endoglucanase activity of the enzyme exposed to stress conditions ("a") is compared to that of a control in which the enzyme is not exposed to the stress conditions ("b"), and residual activity is equal to the ratio a/b. A variant with increased thermostability will have greater residual activity than the wild-type enzyme. In one embodiment the enzymes are exposed to stress conditions of 65° C. at pH 5 for 6 hrs, but any cultivation conditions described herein can be used.

As used herein, the phrases "improved viscosity reduction activity" and "increased viscosity reduction activity" refer to a variant enzyme displaying an increase, relative to a reference sequence (e.g., a wild-type endoglucanase), in reducing the viscosity of biomass in a specified time under specified reaction conditions. Viscosity reduction is an activity of endoglucanases, including the claimed endoglucanase variants as described herein. Methods for measuring the viscosity of a reaction mixture include, but are not limited to, measuring viscosity using a viscometer.

As used herein, "polynucleotide" refers to a polymer of deoxyribonucleotides or ribonucleotides in either single- or double-stranded form, and complements thereof.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The terms "peptide," "polypeptide," and "protein" are used interchangeably herein to refer to a polymer of amino acid residues.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution," as used with respect to amino acids, refers to the substitution of an amino acid with a chemically similar amino acid. Amino acid substitutions that do not generally alter the specific activity are known in the art and are described, for example, by H. Neurath and R. L. Hill, 1979, in "The Proteins," Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse. As used herein, a conservative substitute for a residue is another residue in the same group identified in Table 1 below.

TABLE 1

Conservative amino acid substitutions

| | |
|---|---|
| basic amino acids | arginine (R), lysine (K), histidine (H) |
| acidic amino acids | glutamic acid (E), aspartic acid (D) |
| polar amino acids | glutamine (Q), asparagine (N) |
| hydrophobic amino acids | leucine (L), isoleucine (I), valine (V) |
| aromatic amino acids | phenylalanine (F), tryptophan (W), tyrosine (Y) |
| small amino acids | glycine (G), alanine (A), serine (S), threonine (T), proline (P), cysteine (C), methionine (M) |

The following nomenclature may by used to describe substitutions in a reference sequence relative to a reference sequence or a variant polypeptide or nucleic acid sequence: "R-#-V," where # refers to the position in the reference sequence, R refers to the amino acid (or base) at that position in the reference sequence, and V refers to the amino acid (or base) at that position in the variant sequence. For example, for a variant polypeptide described with reference to SEQ ID NO:1, "L71F" indicates that in the variant polypeptide, the leucine at position 71 of the reference sequence is replaced by phenylalanine, with amino acid position being determined by optimal alignment of the variant sequence with SEQ ID NO:1. Similarly, "A151Q/R/Y" describes three variants: a variant in which the alanine at position 151 is replaced by glutamine, a variant in which the alanine at position 151 is replaced by arginine, and a variant in which the alanine at position 151 is replaced by tyrosine.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant EGs provided herein (e.g., in Table 2, Table 3, Table 4, or Table 5, infra).

The term "isolated" refers to a nucleic acid, polynucleotide, polypeptide, protein, or other component that is partially or completely separated from components with which it is normally associated (other proteins, nucleic acids, cells, etc.).

"Identity" or "percent identity" in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, for example, or at least about 89%, about 90%, about 91%, about 92%, about 93%, about 94%, about 95%, about 96%, about 97%, about 98%, or about 99% identity over a specified region to a reference sequence), when compared and aligned for maximum correspondence over a comparison window, or designated region as measured using sequence comparison algorithms or by manual alignment and visual inspection.

Optimal alignment of sequences for comparison and determination of sequence identity can be determined by a sequence comparison algorithm or by visual inspection as known in the art (see, generally, Ausubel et al., infra). When using a sequence comparison algorithm, test and reference sequences are entered into a computer, subsequence coordinates and sequence algorithm program parameters are designated. The sequence comparison algorithm then calculates the percent sequence identities for the test sequence relative to the reference sequence, based on the program parameters.

In some embodiments, the algorithm used to determine whether a variant endoglucanase has sequence identity to SEQ ID NO:1 is the BLAST algorithm, which is described in Altschul et al., 1990, *J. Mol. Biol.* 215:403-410. Software for performing BLAST analyses is publicly available through the National Center for Biotechnology Information (on the World-Wide Web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915).

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art. See e.g., Dayhoff et al. (1978), "A model of evolutionary change in proteins"; "Atlas of Protein Sequence and Structure," Vol. 5, Suppl. 3 (Ed. M. O. Dayhoff), pp. 345-352, *Natl. Biomed. Res. Round.*, Washington, D.C.; and Henikoff et al. (1992) *Proc. Natl. Acad. Sci. USA,* 89:10915-10919, both of which are incorporated herein by reference. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score.

The phrases "substantial sequence identity" and "substantial identity," in the context of two nucleic acid or polypeptide sequences, refer to a sequence that has at least about 70% identity to a reference sequence. In some embodiments, two sequences are said to have "substantial sequence identity" when they are at least about 70% identical, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical or have greater identity as determined using the methods described herein, such as BLAST using standard parameters as described above. In some embodiments, for an alignment that extends along the entire length of SEQ ID NO:1, there may be at least about 272, at least about 280, at least about 299, at least about 318, at least about 336, at least about 340, at least about 344, at least about 347, at least about 351, at least about 355, at least about 358, at least about 362, at least about 366, or at least about 370 amino acids that are identical between a variant sequence and SEQ ID NO:1. Thus, each recitation of "substantially identical" should be understood to encompass each of the alternatives above.

The term "pre-protein" refers to a protein including an amino-terminal signal peptide (or leader sequence) region attached. The signal peptide is cleaved from the pre-protein by a signal peptidase prior to secretion to result in the "mature" or "secreted" protein.

A "vector" is a DNA construct for introducing a DNA sequence into a cell. A vector may be an expression vector that is operably linked to a suitable control sequence capable of effecting the expression in a suitable host of the polypeptide encoded in the DNA sequence. An "expression vector" has a promoter sequence operably linked to the DNA sequence (e.g., transgene) to drives expression in a host cell.

As used herein, the term "operably linked" refers to a configuration in which a control sequence is appropriately placed at a position relative to the coding sequence of the DNA sequence such that the control sequence influences the expression of a polypeptide.

A promoter sequence, signal peptide, or other sequence is "heterologous", when it is operably linked to a nucleic acid or protein sequence with which the promoter, signal peptide or other sequence is not associated in nature.

The terms "transform" and "transformation," as used in reference to a cell, mean that a cell has a non-native nucleic acid sequence integrated into its genome and/or has an episomal plasmid that is maintained through multiple generations.

The term "introduced," in the context of inserting a nucleic acid sequence into a cell, means transfected, transduced or transformed (collectively "transformed") or otherwise incorporated into the genome of, or maintained as an episome in, the cell.

As used herein, the term "wild-type M. thermophila endoglucanase" or "wild-type M. thermophila EG2" refers to SEQ ID NO:1, the mature peptide sequence (i.e., lacking a signal peptide) of endoglucanase type 2 that is expressed by naturally occurring M. thermophila. In some embodiments, the M. thermophila is C1.

As used herein, the term "variant" refers to a endoglucanase polypeptide or polynucleotide encoding a endoglucanase polypeptide comprising one or more modifications relative to wild-type M. thermophila EG2 or the wild-type polynucleotide encoding M. thermophila EG2 such as substitutions, insertions, deletions, and/or truncations of one or more amino acid residues or of one or more specific nucleotides or codons in the polypeptide or polynucleotide, respectively.

As used herein, the term "reference enzyme" refers to an enzyme to which a variant enzyme of the present invention is compared in order to determine the presence of an improved property in the variant enzyme being evaluated, including but not limited to improved thermoactivity, improved thermostability, and/or improved stability. In some embodiments, a reference enzyme is a wild-type enzyme (e.g., wild-type M. thermophila EG2). In some embodiments, a reference enzyme is another variant enzyme (e.g., another variant enzyme of the present invention), such as those enzymes selected as "backbones" for protein development and design, such as those improved variants identified in successive rounds of evolution.

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

A "cellulase-engineered" cell is a cell comprising at least one, at least two, at least three, or at least four recombinant sequences encoding a cellulase or cellulase variant, and in which expression of the cellulase(s) or cellulase variant(s) has been modified relative to the wild-type form. Expression of a cellulase is "modified" when a non-naturally occurring cellulase variant is expressed or when a naturally occurring cellulase is over-expressed. One way to over-express a cellulase is to operably link a strong (optionally constitutive) promoter to the cellulase encoding sequence. Another way to over-express a cellulase is to increase the copy number of a heterologous, variant, or endogenous cellulase gene. The cellulase-engineered cell may be any suitable fungal cell, including, but not limited to Myceliophthora, Trichoderma, Aspergillus, cells, etc.

The terms "production," "expression". "produce" and "express," in reference to a protein, means expression of a gene to produce mRNA, and transcription of the mRNA to produce an encoded protein, such as a catalytically active (functional) protein (for example, a protein with endoglucanse activity). Production or expression may include any step involved in the production of the polypeptide including, but not limited to, transcription, post-transcriptional modification, translation, post-translational modification, and secretion.

An amino acid or nucleotide sequence (e.g., a promoter sequence, signal peptide, terminator sequence, etc.) is "heterologous" to another sequence with which it is operably linked if the two sequences are not associated in nature.

The term "culturing" refers to growing a population of microbial cells under suitable conditions using a liquid, solid, or semi-solid medium (e.g., a growth medium).

In general, "saccharification" refers to the process in which substrates (e.g., cellulosic biomass) are broken down via the action of cellulases to produce fermentable sugars (e.g. monosaccharides such as but not limited to glucose). "Saccharification" is an enzyme-catalyzed reaction that results in hydrolysis of a complex carbohydrate to produce shorter-chain carbohydrate polymers and/or fermentable sugar(s) that are more suitable for fermentation or further hydrolysis. The enzymes may be cellulase enzyme(s) such as endoglucanase, β glucosidase, a Type 1 and/or Type 2 cellobiohydrolases, a synthetic mixture of any of such enzymes, or cellulase enzymes that are contained in culture broth from an organism that produces cellulase enzymes, such as *M. thermophila* or recombinant yeast cells. Products of saccharification include, but are not limited to disaccharides, and/or monosaccharides such as glucose or xylose.

The SHF method of saccharification comprises the steps of contacting at least one cellulase with a cellulose-containing substrate to enzymatically break down cellulose into fermentable sugars (e.g., monosaccharides such as glucose), contacting the fermentable sugars with a producing microorganism to produce an end product (e.g., an alcohol such as ethanol or butanol) and recovering the alcohol. In some embodiments, the method of consolidated bioprocessing (CBP) can be used, in which the cellulase production from the host is simultaneous with saccharification and fermentation either from one host or from a mixed cultivation (i.e., multiple organisms are cultured together). In addition to SHF methods, a SSF method may be used. In some cases, SSF methods result in a higher efficiency of alcohol production than is afforded by the SHF method (Drissen et al., Biocatalysis and Biotransformation 27:27-35 (2009). One disadvantage of SSF over SHF is that higher temperatures are required for SSF than for SHF.

DETAILED DESCRIPTION OF THE INVENTION

I. Introduction

*Mycelophthora thermophila* produces a variety of cellulases and other enzymes that act in concert to catalyze decrystallization and hydrolysis of cellulose to yield soluble sugars. One *M. thermophila* strain, referred to as "C1" was described by Garg, 1966, "An addition to the genus *Chrysosporium* corda" Mycopathologia 30: 3-4. Also see U.S. Pat. Nos. 6,015,707 and 6,573,086, which are incorporated herein by reference for all purposes.

The *Mycelophthora thermophila* endoglucanase variants described herein are particularly useful for production of soluble sugars from cellulosic biomass. In one aspect, the present invention relates to endoglucanase variants that have improved properties, relative to wild-type *Mycelophthora thermophila* endoglucanases under process conditions that may be beneficial for the improved saccharification of biomass, such as increased thermoactivity, increased thermostability, and/or increased reduction in viscosity. In another aspect, the present invention relates to methods of converting cellulosic biomass to a soluble sugar, comprising contacting the biomass with a composition comprising at least one endoglucanase variant as described herein under conditions suitable for the production of soluble sugar.

Various aspects of the invention are described in the following sections.

II. Variant Endoglucanase Polypeptides

Properties of Endoglucanase Variants

In one aspect, the present invention provides endoglucanase variants that exhibit improved properties over a wild-type endoglucanase. In some embodiments, the endoglucanase variants of the present invention exhibit increased thermoactivity, increased thermostability, and/or increased viscosity reduction activity in comparison to a wild-type *Mycelophthora thermophila* endoglucanase (e.g., a *Mycelophthora thermophila* endoglucanase having the amino acid sequence of SEQ ID NO:1) under conditions relevant to commercial saccharification processes.

The endoglucanase variants of the invention are derived from a *Mycelophthora thermophila* endoglucanase and exhibit one or more amino acid substitutions relative to the wild-type (i.e., naturally occurring) *M. thermophila* endoglucanase sequence of SEQ ID NO:1. In some embodiments, an endoglucanase variant of the present invention comprises an amino acid sequence that is substantially identical to (e.g., has at least about 70%, at least about 75%, about 80%, about 85%, about 90%, about 91%, about 92%, about 93%, about 94%, about 95%, about 96%, about 97%, about 98%, about 99% or more sequence identity to) the wild-type *M. thermophila* endoglucanase sequence of SEQ ID NO:1, and comprises one or more amino acid substitutions relative to SEQ ID NO:1.

In some embodiments, the present invention provides an isolated and/or recombinant endoglucanase variant having greater thermoactivity and/or thermostability and/or viscosity reduction activity than a wild-type *M. thermophila* endoglucanase, and which comprises an amino acid sequence that is substantially identical to (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to) the wild-type *M. thermophila* endoglucanase sequence of SEQ ID NO:1, and comprises at least one amino acid substitution at one or more amino acid residues selected from 1, 5, 12, 18, 27, 45, 48, 49, 51, 50, 54, 56, 61, 70, 71, 72, 76, 82, 85, 86, 87, 91, 94, 95, 96, 101, 106, 112, 117, 118, 127, 128, 131, 133, 134, 135, 143, 145, 146, 147, 150, 151, 153, 155, 167, 169, 173, 174, 177, 186, 190, 191, 202, 203, 205, 207, 210, 211, 224, 226, 232, 236, 240, 242, 245, 248, 250, 254, 256, 257, 264, 270, 272, 276, 277, 282, 283, 286, 287, 289, 290, 298, 299, 300, 302, 304, 312, 314, 321, 323, 325, 326, 328, 330, 338, 351, 357, 358, 359, 360, 363, 366, and 367 as numbered with reference to SEQ ID NO:1.

In some embodiments, the present invention provides an isolated and/or recombinant endoglucanase variant having greater thermoactivity and/or thermostability and/or viscosity reduction activity than a wild-type *M. thermophila* endoglucanase, and which comprises an amino acid sequence that is substantially identical to (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to) the wild-type *M. thermophila* endoglucanase sequence of SEQ ID NO:1, and which comprises at least one amino acid substitution selected from Q1, W5, G12, D18, Y27, Q45, T48, T49, R51, S50, A54, S56, S61, K70, L71, K72, S76, E82, E85, G86, N87, L91, K94, H95, F96, T101, T106, Y112, I117, D118, N127, Q128, S131, F133, D134, E135, E143, V145, N146, F147, N150, A151, K153, A155, G167, V169, T173, N174, R177, Q186, N190, S191, N202, T203, D205, T207, L210, N211, G224, T226, V232, A236, A240, S242, T245, T248, M250, T254, P256, Q257, M264, S270, S272, H276, A277, S282, N283, A286, Q287, V289, V290, A298, N299, G300, L302, V304, A312, A314, T321, L323, D325, H326, Q328, N330, L338, Y351, S357, G358, T359, G360, N363, S366, and I367 as numbered with reference to SEQ ID NO:1.

"Substitution," in this context, means that the residue in the variant protein is other then the residue shown. For example, "H95" denotes a variant comprising an amino acid other than a histidine (i.e., one of the other 19 naturally occurring amino acids) at position 95 relative to SEQ ID:1. In some embodiments, the amino acid in the variant protein is neither the wild-type residue nor a residue that is a conservative substitute for the wild-type residue. As discussed below, in this context, a "conservative substitute" for a residue is another residue in the same group identified in Table 1 above.

In some embodiments, the endoglucanase variant having greater thermoactivity and/or thermostability and/or viscosity reduction activity than a wild-type *M. thermophila* endoglucanase comprises an amino acid sequence that is substantially identical to (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to) the wild-type endoglucanase sequence of SEQ ID NO:1, and comprises one or more amino acid substitutions selected from Q1S, W5M, G12E, D18Q, Y27R, Q45R, T48V, T49R, R51L, 550P, A54C, 556L, S61E, K70C/R, L71F, K72E/H, S76A/M/V, E82K, E85A/D, G86P, N87C, L91M, K94E/I, H95D, F96Y, T101C/P, T106A, Y112M, I117V, D118A/C/G/P/S/TN, N127H, Q128T, S131A/C/G, F133P, D134E/G/H/Q/R/S/T/W/Y, E135P/Q, E143H/T, V145C, N146D/E/Q/R, F147C/Y, N150D/R, A151Q/R/Y, K153Q, A155C, G167D, V169I, T173P, N174D/L/S, R177M, Q186E, N190Q/S/V, 5191P, N202H, T203D/H/K/N/R/S, D205P, T207D, L210P, N211A, G224D, T226G, V232I, A236C/G, A240C, S242C/T, T245Q/V, T248N/Q, M250L, T254M/V, P256R, Q257E/M/S, M264C, S270E, S272G, H276S, A277P, S282A/E/G, N283T, A286E/K/L/V/Q, Q287E, V289L, V290E/R/S/W/Y, A298D/E, N299K, G300H, L302K/M, V304F, A312P, A314T, T321Q, L323M, D325N, H326Y, Q328C, N330H, L338F, Y351F, S357C, G358S, T359K, G360A, N363H, S366A/C/N/P, and I367L/M, wherein the residues are numbered with respect to SEQ ID NO:1.

The present invention additionally provides an isolated and/or recombinant endoglucanase variant having greater thermoactivity and/or thermostability and/or viscosity reduction activity than a wild-type *M. thermophila* endoglucanase, wherein the variant comprises an amino acid sequence that is substantially identical to (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to) the wild-type *M. thermophila* endoglucanase sequence of SEQ ID NO:1; and comprises amino acid substitutions at each of the amino acid residues L71, D118, N202, S242, and M250; and has amino acid substitutions at one or more of the amino acid residues selected from K70, K72, S76, E82, E85, N87, L91, K94, H95, Q128, S131, D134, E135, G167, N174, R177, Q186, N190, T203, D205, N211, G224, T226, V232, A236, T245, T248, T254, Q257, S270, A277, S282, A286, Q287, V289, V290, A298, N299, L302, A312, L338, Y351, G360, N363, and S366, wherein the residues are numbered with respect to SEQ ID NO:1.

The present invention additionally provides an isolated and/or recombinant endoglucanase variant having greater thermoactivity and/or thermostability and/or viscosity reduction activity than a wild-type *M. thermophila* endoglucanase, wherein the variant comprises an amino acid sequence that is substantially identical to (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to) the wild-type *M. thermophila* endoglucanase sequence of SEQ ID NO:1; and comprises amino acid substitutions at each of the amino acid residues L71, S76, D118, N202, T203, S242, M250, and A312; and comprises amino acid substitutions at one or more of the amino acid residues selected from Q1, W5, D18, Y27, Q45, T48, T49, R51, S50, A54, S56, S61, K70, L71, S76, N87, K94, H95, T101, T106, D118, D134, E135, V145, F147, A155, N174, R177, N202, T203, D205, A240, T245, M250, P256, Q257, M264, S272, S282, A286, Q287, V290, A298, A312, Q328, N330, Y351, G360, N363, and S366, wherein the residues are numbered with respect to SEQ ID NO:1.

In one aspect, the invention provides an endoglucanase variant (which may have improved thermoactivity and/or thermostability and/or viscosity reduction activity relative to a wild-type *M. thermophila* endoglucanase) that comprises any individual amino acid substitution set shown in Tables 2, 3, 4 or 5, and optionally additional substitutions.

In some embodiments, the variant endoglucanase comprises at least 2, at least 3, at least 4, at least 5, at least 6, at least 7, at least 8, at least 9, at least 10 or more amino acid residues which have been substituted as compared to the amino acid sequence of SEQ ID NO:1.

As summarized in Table 2, in some embodiments, the present invention provides an isolated and/or recombinant endoglucanase variant having greater thermoactivity and/or thermostability than a wild-type *M. thermophila* endoglucanase, wherein the variant comprises an amino acid sequence having substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity)) to wild-type *M. thermophila* endoglucanase (SEQ ID NO:1), and comprises one or more amino acid substitutions selected from K70R, L71F, K72H, S76A/M/V, E85A, G86P, N87C, L91M, K94E/I, H95D, F96Y, T101P, Y112M, I117V, D118A/C/G/P/S/TN, N127H, Q128T, S131A/C/G, F133P, E135P/Q, E143H/T, N146Q/R, F147Y, N150D/R, A151Q/R/Y, K153Q, V169I, T173P, N174L/S, R177M, Q186E, S191P, N202H, T203D/H/K/N/R/S, D205P, T207D, L210P, N211A, A236G, S242C/T, T245Q/V, T248N/Q, M250L, T254V, Q257M/S, S270E, H276S, A277P, S282A/E, N283T, A286E/K/V/Q, Q287E, V289L, V290E/R/S/W/Y, A298D/E, G300H, L302K, V304F, A312P, A314T, T321Q, L323M, D325N, H326Y, Y351F, S357C, T359K, G360A, N363H, S366A/C/N/P, and I367L, wherein the residues are numbered with respect to SEQ ID NO:1.

As summarized in Table 3, in some embodiments, the present invention provides an isolated and/or recombinant endoglucanase variant having greater thermoactivity and/or thermostability than a wild-type *M. thermophila* endoglucanase, wherein the variant comprises an amino acid sequence having substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to wild-type *M. thermophila* endoglucanase (SEQ ID NO:1), and comprises one or more amino acid substitutions selected from G12E, L71F, H95D, D118P, E135P/Q, N146D, A151Q, S191P, N202H, S242T, M250L, T254M, A312P, G358S, G360A, S366P, and I367M, wherein the residues are numbered with respect to SEQ ID NO:1.

As summarized in Table 4, in some embodiments, the present invention provides an isolated and/or recombinant endoglucanase variant having greater thermoactivity and/or thermostability than a wild-type *M. thermophila* endoglucanase, wherein the variant comprises an amino acid sequence having substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to wild-type *M. thermophila* endoglucanase (SEQ ID NO:1); comprises the amino acid substitutions L71F, D118P, N202H, S242T, and M250L; and comprises one or more amino acid substitutions selected from K70R, K72E/H, S76A/M/V, E82K, E85A/D, N87C, L91M, K94I, H95D, Q128T, S131C, D134E/G/R/S/W/Y, E135P, G167D, N174S, R177M, Q186E, N190Q/S/V, T203D/H/K/N/R, D205P, N211A, G224D, T226G, V232I, A236G, T245V, T248N/Q, T254V, Q257E/M/S, S270E, A277P, S282A/E/G, A286E/K/L/V/Q, Q287E, V289L, V290E/R/S/W/Y, A298D/E, N299K, L302K/M, A312P, L338F, Y351F, G360A, N363H, and S366P, wherein the residues are numbered with respect to SEQ ID NO:1.

As summarized in Table 5, in some embodiments, the present invention provides an isolated and/or recombinant endoglucanase variant having greater thermoactivity and/or thermostability than a wild-type *M. thermophila* endoglucanase, wherein the variant comprises an amino acid sequence having substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to wild-type *M. thermophila* endoglucanase (SEQ ID NO:1); comprises the amino acid substitutions L71F, S76V, D118P, N202H, T203N, S242T, M250L, and A312P; and comprises one or more amino acid substitutions selected from Q1S, W5M, D18Q, Y27R, Q45R, T48V, T49R, R51L, 550P, A54C, S56L, S61E, K70O, N87C, K94I, H95D, T101C, T106A, D134G/H/Q/T/W/Y, E135P, V145C, F147C, A155C, N174D/S, R177M, D205P, A236C, A240C, T245V, P256R, Q257S, M264C, S272G, S282A, A286E/L, Q287E, V290S/W, A298D/E, Q328C, N330H, Y351F, G360A, N363H, and S366P, wherein the residues are numbered with respect to SEQ ID NO:1.

In some embodiments, the endoglucanase variant having greater thermoactivity and/or thermostability and/or viscosity reduction activity than a wild-type *M. thermophila* endoglucanase comprises amino acid substitutions at the amino acid positions corresponding to L71, D118, N202, S242, and M250 as numbered with respect to SEQ ID NO:1. In some embodiments, the endoglucanase variant having greater thermoactivity and/or thermostability and/or viscosity reduction activity than a wild-type *M. thermophila* endoglucanase comprises the amino acid substitutions L71F, D118P, N202H, S242T, and M250L (e.g., SEQ ID NO:8).

In some embodiments, the endoglucanase variant having greater thermoactivity and/or thermostability and/or viscosity reduction activity than a wild-type *M. thermophila* endoglucanase comprises amino acid substitutions at the amino acid positions corresponding to L71, S76, D118, N202, T203, S242, M250, and A312, as numbered with respect to SEQ ID NO:1. In some embodiments, the endoglucanase variant having greater thermoactivity and/or thermostability and/or viscosity reduction activity than a wild-type *M. thermophila* endoglucanase comprises the amino acid substitutions L71F, S76V, D118P, N202H, T203N, S242T, M250L, and A312P (e.g., SEQ ID NO:11).

In some embodiments, the endoglucanase variant having greater thermoactivity and/or thermostability and/or viscosity reduction activity than a wild-type *M. thermophila* endoglucanase comprises amino acid substitutions at the amino acid positions corresponding to L71, S76, H95, D118, D134, N202, T203, S242, M250, A312, Y351, G360, and S366 as numbered with respect to SEQ ID NO:1. In some embodiments, the endoglucanase variant having greater thermoactivity and/or thermostability and/or viscosity reduction activity than a wild-type *M. thermophila* endoglucanase comprises the amino acid substitutions L71F, S76V, H95D, D118P, D134W, N202H, T203N, S242T, M250L, A312P, Y351F, G360A, and S366P (e.g., SEQ ID NO:12).

In some embodiments, the endoglucanase variant having greater thermoactivity and/or thermostability and/or viscosity reduction activity than a wild-type *M. thermophila* endoglucanase comprises amino acid substitutions at the amino acid positions corresponding to L71, S76, H95, D118, D134, N202, T203, S242, M250, A312, Y351, and S366 as numbered with respect to SEQ ID NO:1. In some embodiments, the endoglucanase variant having greater thermoactivity and/or thermostability and/or viscosity reduction activity than a wild-type *M. thermophila* endoglucanase comprises the amino acid substitutions L71F, S76V, H95D, D118P, D134W, N202H, T203N, S242T, M250L, A312P, Y351F, and S366P (e.g., SEQ ID NO:13).

In some embodiments, the endoglucanase variants of the present invention may further comprise a signal peptide linked to the amino-terminus of the polypeptide. In some embodiments, the signal peptide is an endogenous *M. thermophila* endoglucanase signal peptide. In some embodiments, the signal peptide is a signal peptide from another *M. thermophila* secreted protein. In some embodiments, the signal peptide is a signal peptide from an endoglucanase or another secreted protein secreted from an organism other than *M. thermophila* (e.g., from a filamentous fungus, yeast, or bacteria).

It will be appreciated that secreted endoglucanase variants of the present invention may encompass additional amino acid substitutions beyond those listed above (such as additional conservative substitutions) and may be less-than-full length compared to a wild-type secreted *M. thermophila* endoglucanase protein. Thus, endoglucanase variants of the present invention may comprise insertions or deletions (e.g., truncation at the amino- and/or carboxy-termini) relative to SEQ ID NO:1. For illustration and not limitation, in some embodiments the variant may be longer or shorter by up to about 10% of the wild-type length, sometimes up to about 5%, sometimes up to about 4%, sometimes up to about 3%, sometimes up to about 2%, or sometimes up to about 1%.

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 1.9 fold, at least 2.0 to 2.9 fold or higher improvement in thermoactivity over the *M. thermophila* endoglucanase of SEQ ID NO:3, as identified in Table 2, wherein fold improvement in thermoactivity is measured as described in the Examples (e.g., expressed in *S. cerevisiae* and using the same signal peptide as was used for SEQ ID NO:3).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 1.9 fold improvement in thermoactivity over the *M. thermophila* endoglucanase of SEQ ID NO:5, as identified in Table 3, wherein fold improvement in thermoactivity is measured as described in the Examples (e.g., expressed in *S. cerevisiae* and using the 16 amino acid signal peptide of SEQ ID NO:5).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 1.9 fold, at least 2.0 to 2.9 fold, at least 3.0 fold or higher improvement in thermoactivity over the *M. thermophila* endoglucanase variant 213, as identified in Table 4, wherein fold improvement in thermoactivity is measured as described in the Examples (e.g., expressed in *S. cerevisiae* and using the same signal peptide as was used for Variant 213).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 1.4 fold improvement in thermoactivity over the *M. thermophila* endoglucanase variant 309, as identified in Table 5, wherein fold improvement in thermoactivity is measured as described in the Examples (e.g., expressed in *S. cerevisiae* and using the same signal peptide as was used for Variant 309).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 5.0 fold, at least 5 to 10 fold, at least 10 to 20 fold or higher improvement in thermostability over the *M. thermophila* endoglucanase of SEQ ID NO:3, as identified in Table 2, wherein fold improvement in themostability is measured as described in the Examples (e.g., expressed in *S. cerevisiae* and using the same signal peptide as was used for SEQ ID NO:3).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 5.0 fold improvement in thermostability over the *M. thermophila* endoglucanase of SEQ ID NO:5, as identified in Table 3, wherein fold improvement in themostability is measured as described in the Examples (e.g., expressed in *S. cerevisiae* and using the same signal peptide as was used for SEQ ID NO:5).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 5.0 fold, at least 5 to 10 fold or higher improvement in thermostability over the *M. thermophila* endoglucanase variant 213, as identified in Table 4, wherein fold improvement in themostability is measured as described in the Examples (e.g., expressed in *S. cerevisiae* and using the same signal peptide as was used for Variant 213).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1, and comprises an amino acid substitution set selected from substitution sets showing at least 1.1 to 5.0 fold or higher improvement in thermostability over the C1 endoglucanase variant 309, as identified in Table 5, wherein fold improvement in themostability is measured as described in the Examples (e.g., expressed in *S. cerevisiae* and using the same signal peptide as was used for Variant 309).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1; and comprises an amino acid substitution set selected from substitution sets showing at least 1.1, at least 2.0, at least 3.0, or greater fold improvement in thermoactivity and at least 1.1, at least 5, at least 10, or greater fold improvement in thermostability over the *M. thermophila* endoglucanase of SEQ ID NO:3, as shown in Table 2, wherein fold improvement in thermoactivity and themostability is measured as described in the Examples (e.g., expressed in *S. cerevisiae* and using the same signal peptide as was used for SEQ ID NO:3).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1; and comprises an amino acid substitution set selected from substitution sets showing at least 1.1, at least 2.0, at least 3.0, or greater fold improvement in thermoactivity and at least 1.1, at least 5, at least 10, or greater fold improvement in thermostability over the endoglucanase of SEQ ID NO:5, as shown in Table 3, wherein fold improvement in thermoactivity and themostability is measured as described in the Examples (e.g., expressed in *S. cerevisiae* and using the same signal peptide as was used for SEQ ID NO:5).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1; and comprises an amino acid substitution set selected from substitution sets showing at least 1.1, at least 2.0, at least 3.0, or greater fold improvement in thermoactivity and at least 1.1, at least 5, at least 10, or greater fold improvement in thermostability, over the endoglucanase variant 213, as shown in Table 4, wherein fold improvement in thermoactivity and themostability is measured as described in the Examples (e.g., expressed in *S. cerevisiae* and using the same signal peptide as was used for Variant 213).

In some embodiments, the endoglucanase variant of the present invention has substantial identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% or greater sequence identity) to the wild-type *M. thermophila* endoglucanase of SEQ ID NO:1; and comprises an amino acid substitution set selected from substitution sets showing at least 1.1, at least 2.0, at least 3.0, or greater fold improvement in thermoactivity and at least 1.1, at least 5, at least 10, or greater fold improvement in thermostability, over endoglucanase Variant 309, as shown in Table 5, wherein fold improvement in thermoactivity and themostability is measured as described in the Examples (e.g., expressed in *S. cerevisiae* and using the same signal peptide as was used for Variant 309).

In some embodiments, the invention encompasses the mature endoglucanase proteins in Tables 2-5, as well as variants that comprise an amino acid substitution set provided in Table 2, Table 3, Table 4, or Table 5 and have substantial sequence identity (e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity) to SEQ ID NO:1.

In some embodiments, the present invention relates to a method of making endoglucanase variants having improved thermoactivity and/or improved thermostability and/or improved viscosity reduction. In some embodiments, the method comprises:

(a) identifying a sequence that is substantially identical to (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to) the wild-type endoglucanase of SEQ ID NO:1;

(b) aligning the identified sequence with the sequence of SEQ ID NO:1; and (c) substituting one or more amino acid residues from the identified sequence, wherein the one or more amino acid residues to be substituted are selected from 1, 5, 12, 18, 27, 45, 48, 49, 51, 50, 54, 56, 61, 70, 71, 72, 76, 82, 85, 86, 87, 91, 94, 95, 96, 101, 106, 112, 117, 118, 127, 128, 131, 133, 134, 135, 143, 145, 146, 147, 150, 151, 153, 155, 167, 169, 173, 174, 177, 186, 190, 191, 202, 203, 205, 207, 210, 211, 224, 226, 232, 236, 240, 242, 245, 248, 250, 254, 256, 257, 264, 270, 272, 276, 277, 282, 283, 286, 287, 289, 290, 298, 299, 300, 302, 304, 312, 314, 321, 323, 325, 326, 328, 330, 338, 351, 357, 358, 359, 360, 363, 366, and 367, numbered with reference to SEQ ID NO:1.

In some embodiments, the present invention relates to a method of making endoglucanase variants having improved thermoactivity and/or improved thermostability and/or improved viscosity reduction. In some embodiments, the method comprises:

(a) identifying a sequence that is substantially identical to (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to) the wild-type endoglucanase of SEQ ID NO:1;

(b) aligning the identified sequence with the sequence of SEQ ID NO:1; and (c) substituting one or more amino acid residues from the identified sequence, wherein the one or more amino acid residues to be substituted are selected from Q1, W5, G12, D18, Y27, Q45, T48, T49, R51, S50, A54, S56, S61, K70, L71, K72, S76, E82, E85, G86, N87, L91, K94, H95, F96, T101, T106, Y112, I117, D118, N127, Q128, S131, F133, D134, E135, E143, V145, N146, F147, N150, A151, K153, A155, G167, V169, T173, N174, R177, Q186, N190, S191, N202, T203, D205, T207, L210, N211, G224, T226, V232, A236, A240, S242, T245, T248, M250, T254, P256, Q257, M264, S270, S272, H276, A277, S282, N283, A286, Q287, V289, V290, A298, N299, G300, L302, V304, A312, A314, T321, L323, D325, H326, Q328, N330, L338, Y351, S357, G358, T359, G360, N363, S366, and I367, numbered with reference to SEQ ID NO:1.

In some embodiments, step (c) of the method comprises substituting one or more amino acid residues from the identified sequence, wherein the one or more amino acid substitutions are selected from Q1S, W5M, G12E, D18Q, Y27R, Q45R, T48V, T49R, R51L, S50P, A54C, S56L, S61E, K70C/R, L71F, K72E/H, S76A/M/V, E82K, E85A/D, G86P, N87C, L91M, K94E/I, H95D, F96Y, T101C/P, T106A, Y112M, I117V, D118A/C/G/P/S/T/Y, N127H, Q128T, S131A/C/G, F133P, D134E/G/H/Q/R/S/T/W/Y, E135P/Q, E143H/T, V145C, N146D/E/Q/R, F147C/Y, N150D/R, A151Q/R/Y, K153Q, A155C, G167D, V169I, T173P, N174D/L/S, R177M, Q186E, N190Q/S/V, S191P, N202L, T203D/H/K/N/R/S, D205P, T207D, L210P, N211A, G224D, T226G, V232I, A236C/G, A240C, S242C/T, T245Q/V, T248N/Q, M250L, T254M/V, P256R, Q257E/M/S, M264C, S270E, S272G, H276S, A277P, S282A/E/G, N283T, A286E/K/L/V/Q, Q287E, V289L, V290E/R/S/W/Y, A298D/E, N299K, G300H, L302K/M, V304F, A312P, A314T, T321Q, L323M, D325N, H326Y, Q328C, N330H, L338F, Y351F, S357C, G358S, T359Y, G360A, N363H, S366A/C/N/P, and I367L/M, numbered with reference to SEQ ID NO:1.

ProSAR Analysis of Endoglucanase Variants

Sequence-activity analysis of variants was performed in accordance with the methods described in WO 03/075129, U.S. Ser. No. 10/379,378, published as US 2004-0072245 on Apr. 15, 2004; R. Fox et al., 2003, "Optimizing the search algorithm for protein engineering by directed evolution," *Protein Eng.* 16(8):589-597, and R. Fox et al., 2005, "Directed molecular evolution by machine learning and the influence of nonlinear interactions," *J. Theor. Biol.* 234(2): 187-199, all of which are incorporated herein by reference, to identify substitutions with likely the most significant effects on activity.

Certain endoglucanase variants of the present invention have an amino acid sequence that comprises at least one amino acid substitution selected from L71F, S76V, H95D, D118P, D134W, N202H, T203N, S242T, M250L, A312P, Y351F, G360A, and S366P, which are highly beneficial substitutions for increasing endoglucanase activity and/or thermostability. In some embodiments, an endoglucanase variant of the present invention has an amino acid sequence comprising the amino acid substitution L71F. In some embodiments, an endoglucanase variant of the present invention has an amino acid sequence comprising the amino acid substitution S76V. In some embodiments, an endoglucanase variant of the present invention has an amino acid sequence comprising the amino acid substitution H95D. In some embodiments, an endoglucanase variant of the present invention has an amino acid sequence comprising the amino acid substitution D118P. In some embodiments, an endoglucanase variant of the present invention has an amino acid sequence comprising the amino acid substitution D134W. In some embodiments, an endoglucanase variant of the present invention has an amino acid sequence comprising the amino acid substitution N202H. In some embodiments, an endoglucanase variant of the present invention has an amino acid sequence comprising the amino acid substitution T203N. In some embodiments, an endoglucanase variant of the present invention has an amino acid sequence comprising the amino acid substitution S242T. In some embodiments, an endoglucanase variant of the present invention has an amino acid sequence comprising the amino acid substitution M250L. In some embodiments, an endoglucanase variant of the present invention has an amino acid sequence comprising the amino acid substitution A312P. In some embodiments, an endoglucanase variant of the present invention has an amino acid sequence comprising the amino acid substitution Y351F. In some embodiments, an endoglucanase variant of the present invention has an amino acid sequence comprising the amino acid substitution G360A. In some embodiments, an endoglucanase variant of the present invention has an amino acid sequence comprising the amino acid substitution S366P.

In some embodiments, an endoglucanase variant of the present invention has an amino acid sequence that comprises at least two, at least three, at least four or more substitutions selected from L71F, S76V, H95D, D118P, D134W, N202H, T203N, S242T, M250L, A312P, Y351F, G360A, and S366P. Certain endoglucanase variants of the present invention have an amino acid sequence that comprises 2, 3, 4, 5, 6, 7, 8, 9, 10, 11, 12, or 13 amino acid substitutions selected from L71F, S76V, H95D, D118P, D134W, N202H, T203N, S242T, M250L, A312P, Y351F, G360A, and S366P. These substitutions represent highly beneficial substitutions for increasing endoglucanase activity and/or thermostability.

Certain endoglucanase variants of the present invention have amino acid sequences that comprise the substitutions L71F+D118P+N202H+S242T+M250L (e.g., as found in Variant 213). Certain other endoglucanase variants of the present invention have amino acid sequences that comprise the substitutions L71F+S76V+D118P+N202H+T203N+S242T+M250L+A312P (e.g., as found in Variant 309). Certain other endoglucanase variants of the present invention have amino acid sequences that comprise the substitutions L71F+S76V+H95D+D118P+D134W+N202H+T203N+S242T+M250L+A312P+Y351F+G260A+S366P (e.g., as found in Variant 372). Certain other endoglucanase variants of the present invention have amino acid sequences that comprise the substitutions L71F+S76V+H95D+D118P+D134W+N202H+T203N+S242T+M250L+A312P+Y351F+S366P (e.g., as found in Variant 443). These substitutions represent highly beneficial substitutions for increasing endoglucanase activity and/or thermostability.

Certain endoglucanase variants of the present invention have amino acid sequences comprising at least one amino acid substitution selected from S76A/M, E85A, N87C, L91M, K94I, Q128T, N174S, R177M, Q186E, T203H/K/R/S, D205P, N211A, T248Q, S270E, A277P, A286E, V289L, V290R/S/W/Y, A298D/E, L302K, and N363H, which represent highly beneficial substitutions for increasing endoglucanase activity and/or thermostability. In some embodiments, an endoglucanase variant of the present invention has an amino acid sequence comprising the amino acid substitution S76A. In some embodiments, an endoglucanase variant of the present invention has an amino acid sequence comprising the amino acid substitution S76M. In some embodiments, an endoglucanase variant of the present invention has an amino acid sequence comprising the amino acid substitution E85A. In some embodiments, an endoglucanase variant of the present invention has an amino acid sequence comprising the amino acid substitution N87C. In some embodiments, an endoglucanase variant of the present invention has an amino acid sequence comprising the amino acid substitution L91M. In some embodiments, an endoglucanase variant of the present invention has an amino acid sequence comprising the amino acid substitution K94I. In some embodiments, an endoglucanase variant of the present invention has an amino acid sequence comprising the amino acid substitution Q128T. In some embodiments, an endoglucanase variant of the present invention has an amino acid sequence comprising the amino acid substitution N174S. In some embodiments, an endoglucanase variant of the present invention has an amino acid sequence comprising the amino acid substitution R177M. In some embodiments, an endoglucanase variant of the present invention has an amino acid sequence comprising the amino acid substitution Q186E. In some embodiments, an endoglucanase variant of the present invention has an amino acid sequence comprising the amino acid substitution T203H. In some embodiments, an endoglucanase variant of the present invention has an amino acid sequence comprising the amino acid substitution T203K. In some embodiments, an endoglucanase variant of the present invention has an amino acid sequence comprising the amino acid substitution T203R. In some embodiments, an endoglucanase variant of the present invention has an amino acid sequence comprising the amino acid substitution T203S. In some embodiments, an endoglucanase variant of the present invention has an amino acid sequence comprising the amino acid substitution D205P. In some embodiments, an endoglucanase variant of the present invention has an amino acid sequence comprising the amino acid substitution N211A. In some embodiments, an endoglucanase variant of the present invention has an amino acid sequence comprising the amino acid substitution T248Q. In some embodiments, an endoglucanase variant of the present invention has an amino acid sequence comprising the amino acid substitution S270E. In some embodiments, an endoglucanase variant of the present invention has an amino acid sequence comprising the amino acid substitution A277P. In some embodiments, an endoglucanase variant of the present invention has an amino acid sequence comprising the amino acid substitution A286E. In some embodiments, an endoglucanase variant of the present invention has an amino acid sequence comprising the amino acid substitution V289L. In some embodiments, an endoglucanase variant of the present invention has an amino acid sequence comprising the amino acid substitution V290R. In some embodiments, an endoglucanase variant of the present invention has an amino acid sequence comprising the amino acid substitution V290S. In some embodiments, an endoglucanase variant of the present invention has an amino acid sequence comprising the amino acid substitution V290W. In some embodiments, an endoglucanase variant of the present invention has an amino acid sequence comprising the amino acid substitution V290Y. In some embodiments, an endoglucanase variant of the present invention has an amino acid sequence comprising the amino acid substitution A298D. In some embodiments, an endoglucanase variant of the present invention has an amino acid sequence comprising the amino acid substitution A298E. In some embodiments, an endoglucanase variant of the present invention has an amino acid sequence comprising the amino acid substitution L302K. In some embodiments, an endoglucanase variant of the present invention has an amino acid sequence comprising the amino acid substitution N363H. In some embodiments, an endoglucanase variant of the present invention has an amino acid sequence comprising at least two, at least three, at least four or more substitutions selected from S76A/M, E85A, N87C, L91M, K94I, Q128T, N174S, R177M, Q186E, T203H/K/R/S, D205P, N211A, T248Q, S270E, A277P, A286E, V289L, V290R/S/W/Y, A298D/E, L302K, and N363H. In some embodiments, an endoglucanase variant of the present invention having an amino acid sequence comprising one or more substitutions selected from S76A/M, E85A, N87C, L91M, K94I, Q128T, N174S, R177M, Q186E, T203H/K/R/S, D205P, N211A, T248Q, S270E, A277P, A286E, V289L, V290R/S/W/Y, A298D/E, L302K, and N363H further comprises one or more amino acid substitutions selected from L71F, S76V, H95D, D118P, D134W, N202H, T203N, S242T, M250L, A312P, Y351F, G360A, and S366P. These substitutions represent highly beneficial substitutions for increasing endoglucanase activity and/or thermostability.

Certain endoglucanase variants of the present invention have an amino acid sequence comprising at least one amino acid substitution selected from Q1S, W5M, D18Q, Y27R, T48V, T49R, R51L, A54C, S56L, S61E, K70R, K72H, D118A, D118C, D118G, D118S, D118T, D118Y, S131C, D134G, E143H, N146R, F147Y, N150D, A151Q, T207D, A236G, S242C, T245V, T254V, Q257M, S272G, S282A, and A286V, which represent highly beneficial substitutions for increasing endoglucanase activity and/or thermostability. In some embodiments, an endoglucanase variant of the present invention has an amino acid sequence comprising the amino acid substitution Q1S. In some embodiments, an endoglucanase variant of the present invention has an amino acid sequence comprising the amino acid substitution W5M. In some embodiments, an endoglucanase variant of the present invention has an amino acid sequence comprising the amino acid substitution D18Q. In some embodiments, an endoglucanase variant of the present invention has an amino acid sequence comprising the amino acid substitution Y27R. In some embodiments, an endoglucanase variant of the present invention has an amino acid sequence comprising the amino acid substitution T48V. In some embodiments, an endoglucanase variant of the present invention has an amino acid sequence comprising the amino acid substitution T49R. In some embodiments, an endoglucanase variant of the present invention has an amino acid sequence comprising the amino acid substitution R51 L. In some embodiments, an endoglucanase variant of the present invention has an amino acid sequence comprising the amino acid substitution A54C. In some embodiments, an endoglucanase variant of the present invention has an amino acid sequence comprising the amino acid substitution S56L. In some embodiments, an endoglucanase variant of the present invention has an amino acid sequence comprising the amino acid substitution S61E. In some embodiments, an endoglucanase variant of the present invention has an amino acid sequence comprising the amino acid substitution K70R. In some embodiments, an endoglucanase variant of the present invention has an amino acid sequence comprising the amino acid substitution K72H. In some embodiments, an endoglucanase variant of the present invention has an amino acid sequence comprising the amino acid substitution D118A. In some embodiments, an endoglucanase variant of the present invention has an amino acid sequence comprising the amino acid substitution D118C. In some embodiments, an endoglucanase variant of the present invention has an amino acid sequence comprising the amino acid substitution D118G. In some embodiments, an endoglucanase variant of the present invention has an amino acid sequence comprising the amino acid substitution D118S. In some embodiments, an endoglucanase variant of the present invention has an amino acid sequence comprising the amino acid substitution D118T. In some embodiments, an endoglucanase variant of the present invention has an amino acid sequence comprising the amino acid substitution D118Y. In some embodiments, an endoglucanase variant of the present invention has an amino acid sequence comprising the amino acid substitution S131C. In some embodiments, an endoglucanase variant of the present invention has an amino acid sequence comprising the amino acid substitution D134G. In some embodiments, an endoglucanase variant of the present invention has an amino acid sequence comprising the amino acid substitution E143H. In some embodiments, an endoglucanase variant of the present invention has an amino acid sequence comprising the amino acid substitution N146R. In some embodiments, an endoglucanase variant of the present invention has an amino acid sequence comprising the amino acid substitution F147Y. In some embodiments, an endoglucanase variant of the present invention has an amino acid sequence comprising the amino acid substitution N150D. In some embodiments, an endoglucanase variant of the present invention has an amino acid sequence comprising the amino acid substitution A151Q. In some embodiments, an endoglucanase variant of the present invention has an amino acid sequence comprising the amino acid substitution T207D. In some embodiments, an endoglucanase variant of the present invention has an amino acid sequence comprising the amino acid substitution A236G. In some embodiments, an endoglucanase variant of the present invention has an amino acid sequence comprising the amino acid substitution S242C. In some embodiments, an endoglucanase variant of the present invention has an amino acid sequence comprising the amino acid substitution T245V. In some embodiments, an endoglucanase variant of the present invention has an amino acid sequence comprising the amino acid substitution T254V. In some embodiments, an endoglucanase variant of the present invention has an amino acid sequence comprising the amino acid substitution Q257M. In some embodiments, an endoglucanase variant of the present invention has an amino acid sequence comprising the amino acid substitution S272G. In some embodiments, an endoglucanase variant of the present invention has an amino acid sequence comprising the amino acid substitution S282A. In some embodiments, an endoglucanase variant of the present invention has an amino acid sequence comprising the amino acid substitution A286V. In some embodiments, an endoglucanase variant of the present invention comprising an amino acid sequence comprising at least one amino acid substitution selected from Q1S, W5M, D18Q, Y27R, T48V, T49R, R51L, A54C, S56L, S61E, K70R, K72H, D118A, D118C, D118G, D118S, D118T, D118Y, S131C, D134G, E143H, N146R, F147Y, N150D, A151Q, T207D, A236G, S242C, T245V, T254V, Q257M, S272G, S282A, and A286V; and further comprises one or more amino acid substitutions selected from L71F, S76V, H95D, D118P, D134W, N202H, T203N, S242T, M250L, A312P, Y351F, G360A, and S366P. These substitutions represent highly beneficial substitutions for increasing endoglucanase activity and/or thermostability.

Certain endoglucanase variants of the present invention have an amino acid sequence that includes at least one substitution of an amino acid residue selected from G12E, S50P, V76S, T101P, S131A, F133P, E135P/Q, L141L, S191P, T203D, L210P, T254M, Q287E, V290E, V304F, and L323M, represent highly beneficial substitutions for increasing endoglucanase activity and/or thermostability. In some embodiments, an endoglucanase variant of the present invention has an amino acid sequence comprising at least two, at least three, at least four or more substitutions selected from G12E, S50P, V76S, T101P, S131A, F133P, E135P/Q, L141L, S191P, T203D, L210P, T254M, Q287E, V290E, V304F, and L323M. In some embodiments, an endoglucanase variant of the present invention has an amino acid sequence comprising one or more substitutions selected from G12E, S50P, V76S, T101P, S131A, F133P, E135P/Q, L141L, S191P, T203D, L210P, T254M, Q287E, V290E, V304F, and L323M; and further comprises one or more amino acid substitutions selected from L71F, S76V, H95D, D118P, D134W, N202H, T203N, S242T, M250L, A312P, Y351F, G360A, and S366P. These substitutions represent highly beneficial substitutions for increasing endoglucanase activity and/or thermostability.

In particular, a number of variants with improved activity and/or thermostability comprise substitutions at position 118, with at least 7 different alternative (e.g., non-aspartic acid) residues (e.g., as provided herein in experimentally identified mutants). Substitutions at position 118 increase activity and/or thermostability. Thus, in one aspect the present invention provides a variant endoglucanase polypeptide comprising an amino acid sequence that is substantially identical (e.g., at least 70% identical) to wild-type M. thermophila endoglucanase (SEQ ID NO:1) wherein the amino acid at position 118 is not aspartic acid. In some embodiments, the amino acid at position 118 is selected from A, C, G, S, P, T, and Y and conservative substitutions thereof (see Table 1). In some embodiments, the amino acid at position 118 is P (proline), which appears particularly beneficial for enhancing endoglucanase activity and thermostability. In some embodiments, an endoglucanase variant of the present invention has an amino acid sequence having an amino acid residue at position 118 selected from A, C, G, S, P, T, and Y and conservative substitutions thereof, further comprises one or more amino acid substitutions selected from L71F, S76V, H95D, D134W, N202H, T203N, S242T, M250L, A312P, Y351F, G360A, and S366P.

Additionally, a number of variants with improved activity and/or thermostability comprise substitutions at position 203, with at least 6 different alternative (e.g., non-threonine) residues (e.g., as provided herein in experimentally identified mutants). Substitutions at position 203 increase activity and/or thermostability. Thus, in one aspect the present invention provides a variant endoglucanase polypeptide comprising an amino acid sequence that is substantially identical (e.g., at least 70% identical) to wild-type M. thermophila endoglucanase (SEQ ID NO:1) wherein the amino acid at position 203 is not threonine. In some embodiments, the amino acid at position 203 is selected from D, K, N, R, H, and S and conservative substitutions thereof (see Table 1). In some embodiments, the amino acid at position 203 is N (asparagine), which appears particularly beneficial for endoglucanase activity and thermostability. In some embodiments, an endoglucanase variant of the present invention has an amino acid sequence having an amino acid residue at position 203 selected from D, K, N, R, H, and S and conservative substitutions thereof, further comprises one or more amino acid substitutions selected from L71F, S76V, H95D, D118P, D134W, N202H, S242T, M250L, A312P, Y351F, G360A, and S366P.

Endoglucanase Homologs

The present invention contemplates that substitutions may be introduced into endoglucanases of other fungal species, at positions corresponding to the substituted positions of the M. thermophila endoglucanase, to produce variants with similarly desirable properties.

For example, a number of fungal strains (including, but not limited to, *Talaromyces, Aspergillus, Trichoderma, Neurospora, Penicillium, Fusarium, Humicola, Myceliophthora, Corynascus, Chaetomium, Tolypocladium, Thielavia, Acremonium, Sporotrichum, Thermoascus,* and *Chrysosporium*) express endoglucanases with sequence identity to the *M. thermophila* endoglucanase. The present invention contemplates that variants of these fungal endoglucanases in which substitutions are made at residues corresponding to the *M. thermophila* endoglucanase positions and substitutions disclosed herein. Examples of fungal endoglucanases with sequence identity include, for example: *Chaetomium globosum* CBS 148.51 (Accession No. XP_001220409.1); *Neurospora crassa*OR74A (Accession No. XP_964159.1); *Humicola grisea* var. *thermoidea* (Accession No. BAA12676.1); *Humicola insolens* (Accession No. Q12624.1); *Podospora anserina* S mat+ (Accession No. XP_00192812.1); *Nectria haematococca* mpVI 77-13-4 (Accession No. XP_003040869); *Glomerella graminicola* M1.001 (Accession No. EFQ33605.1); *Gibberella zeae* PH-1 (Accession No. XP_383971.1); *Pestalotiopsis* sp. AN 7 (Accession No. BAI66446.1); *Penicillium marneffei* ATCC 18224 (Accession No. XP_00214979.1); *Penicillium chrysogenum* Wisconsin 54-1255 (Accession No. XP_002562753.1); *Penicillium brasilianum* (Accession No. ACB06750.1); *Aspergillus nidulans* FGSC A4 (Accession No. XP_658889.1); *Talaromyces stipitatus* ATCC 10500 (Accession No. XP_002339997.1); *Aspergillus clavatus* NRRL 1 (Accession No. XP_001268256.1); *Aspergillus oryzae* (Accession No. BAD72778.1); *Emericella nidulans* (Accession No. BAA82592.1); *Neosartorya fischeri* NRRL 181 (Accession No. XP_001257866.1); *Aspergillus oryzae* RIB40 (Accession No. XP_001818463.1); *Aspergillus acu-*

*leatus* (Accession No. AAN16396.1); *Thermoascus aurantiacus* (Accession No. AAL88714.2); *Talaromyces emersonii* (Accession No. AAL33630.2); and *Aspergillus niger* (Accession No. AAG50051.1). In some embodiments, a variant endoglucanase polypeptide is derived from, and has improved activity and/or stability relative to, an endoglucanase homolog of SEQ ID NO:1, wherein the homolog is from a *Chrysosporium* species, a *Myceliophthora* species, an *Aspergillus* species, a *Trichoderma* species, and/or a *Fusarium* species.

Generation of Endoglucanase Variants

Libraries of endoglucanase variant polypeptides (and polynucleotides encoding the variants) may be generated from a parental sequence (e.g., wild-type *M. thermophila* endoglucanase, or one of the endoglucanase variants exemplified herein) and screened using a high throughput screen to determine improved properties such as increased activity or stability at desired conditions, as described herein. Mutagenesis and directed evolution methods known in the art can be readily applied to polynucleotides encoding endoglucanase variants exemplified herein to generate variant libraries that can be expressed, screened, and assayed using the methods described herein. Mutagenesis and directed evolution methods are well known in the art. See, e.g., Ling, et al., 1999, "Approaches to DNA mutagenesis: an overview," *Anal. Biochem.*, 254(2):157-78; Dale, et al., 1996, "Oligonucleotide-directed random mutagenesis using the phosphorothioate method," *Methods Mol. Biol.*, 57:369-74; Smith, 1985, "In vitro mutagenesis," *Ann. Rev. Genet.*, 19:423-462; Botstein, et al., 1985, "Strategies and applications of in vitro mutagenesis," *Science*, 229:1193-1201; Carter, 1986, "Site-directed mutagenesis," *Biochem. J.*, 237:1-7; Kramer, et al., 1984, "Point Mismatch Repair," *Cell*, 38:879-887; Wells, et al., 1985, "Cassette mutagenesis: an efficient method for generation of multiple mutations at defined sites," *Gene*, 34:315-323; Minshull, et al., 1999, "Protein evolution by molecular breeding," *Current Opinion in Chemical Biology*, 3:284-290; Christians, et al., 1999, "Directed evolution of thymidine kinase for AZT phosphorylation using DNA family shuffling," *Nature Biotechnology*, 17:259-264; Crameri, et al., 1998, "DNA shuffling of a family of genes from diverse species accelerates directed evolution," *Nature*, 391: 288-291; Crameri, et al., 1997, "Molecular evolution of an arsenate detoxification pathway by DNA shuffling," *Nature Biotechnology*, 15:436-438; Zhang, et al., 1997 "Directed evolution of an effective fucosidase from a galactosidase by DNA shuffling and screening," *Proceedings of the National Academy of Sciences, U.S.A.*, 94:45-4-4509; Crameri, et al., 1996, "Improved green fluorescent protein by molecular evolution using DNA shuffling," *Nature Biotechnology*, 14:315-319; Stemmer, 1994, "Rapid evolution of a protein in vitro by DNA shuffling," *Nature*, 370:389-391; Stemmer, 1994, "DNA shuffling by random fragmentation and reassembly: In vitro recombination for molecular evolution," *Proceedings of the National Academy of Sciences, U.S.A.*, 91:10747-10751; WO 95/22625; WO 97/0078; WO 97/35966; WO 98/27230; WO 00/42651; and WO 01/75767, all of which are incorporated herein by reference.

An endoglucanase variant polypeptide of the invention can be subject to further modification to generate new polypeptides that retain the specific substitution(s) that characterizes the variant and which may have desirable properties. For example, a polynucleotide encoding an endoglucanase variant with an improved property can be subjected to additional rounds of mutagenesis treatments to generate polypeptides with further improvements in the desired enzyme property.

The number of modifications to the reference polypeptide, e.g., SEQ ID NO:1, that produces an improved endoglucanase property may comprise modifications at one or more amino acid positions. Protein evolution of combinatorial mutations can be accomplished by any method known in the art including, but not limited to, classical and/or synthetic DNA shuffling techniques.

Classical DNA shuffling generates variant DNA molecules by in vitro homologous recombination from random fragmentation of a parental DNA followed by reassembly using ligation and/or PCR, which results in randomly introduced point mutations. It consists of a three-step process that begins with the enzymatic digestion of genes, yielding smaller fragments of DNA. The small fragments are then allowed to randomly hybridize and are filled in to create longer fragments. Ultimately, any full-length, recombined genes that are re-created are amplified via PCR. If a series of alleles or mutated genes is used as a starting point for DNA shuffling, the result is a library of recombined genes that can be translated into novel proteins. The library can in turn be screened for increased activity at the desired conditions as described above. Endoglucanases that were generated with single amino acid mutations via either random or site-directed mutagenesis as described herein provide a parental or reference nucleotide sequence. Genes with beneficial mutations can be shuffled further, both to bring together these independent, beneficial mutations in a single nucleotide sequence and to eliminate any mutations that would prevent the desired endoglucanase for exhibiting activity that the pH and temperatures desired for the present invention.

Synthetic DNA shuffling may also be used to increase endoglucanase activity. In synthetic recombination methods, a plurality of oligonucleotides are synthesized which collectively encode a plurality of the mutations to be recombined. The oligonucleotides are designed based on the determination of favorable amino acid substitutions as described above. Following manufacture of the oligonucleotides, the methods of shuffling as described above can be used to create a library of variant endoglucanases.

Recombination-based directed evolution may further be complemented by protein sequence activity relationships (ProSAR), which incorporates statistical analyses in targeting amino acid residues for mutational analysis. See, e.g., Fox et al., *Nature Biotechnology* 25: 338-344 (2007). Using directed evolution in combination with statistical analysis facilitates mutation-oriented enzyme optimization by identifying beneficial mutations even in endoglucanase variants with reduced function. See, e.g., U.S. Pat. Nos. 7,790,381; 6,537,746; 6,489,146; and 6,177,263, the disclosure of each of which is incorporated by reference herein in its entirety.

Methods of protein evolution are well known in the art. See, e.g., Wells et al., *Gene* 34:315-323 (1985); Minshull et al., *Curr Opin Chem Biol* 3:284-290 (1999); Christians et al, *Nature Biotech* 17:259-264 (1999); Crameri et al., *Nature* 391:288-291 (1998); Crameri et al., *Nature Biotech* 15:436-438 (1997); Zhang et al., *Proc Natl Acad Sci USA* 94:45-4-4509 (1997); Crameri et al., *Nature Biotech* 14:315-319 (1996); Stemmer, *Nature* 370:389-391 (1994); Stemmer, *Proc Natl Acad Sci USA* 91:10747-10751 (1994); WO 95/22625; WO 97/0078; WO 97/35966; WO 98/27230; WO 00/42651; WO 01/75767 and U.S. Pat. Nos. 5,605,793, 5,811,238, 5,830,721, 5,834,252, 5,837,458 and 6,537,746.

Variants that are truncated or comprise deletions relative to full-length EG proteins of this invention (e.g., SEQ ID NO:1) can be identified by standard methods for mapping function within a polypeptide, as known in the art. For example, recombinant protein is expressed that has effectively been truncated at the N- or C-terminus, and then tested in an EG activity assay. Further truncation can continue until activity is lost, at which point the minimum functional unit of the protein would be identified. A biologically active EG with an amino-terminal and/or carboxy-terminal deletion and/or internal deletion relative to SEQ ID NO:1 may comprise about 60%, about 65%, about 70%, about 75%, about 80%, about 85%, at about 90%, about 91%, about 92%, about 93%, about 94%, about 95%, about 96%, about 97%, about 98%, or about 99% the length of a full-length EG polypeptide.

Endoglucanase variants having the amino acid substitutions described herein can also be synthetically generated. Chemically synthesized polypeptides may be generated using any suitable method, including but not limited to the well-known techniques of solid phase, liquid phase, or peptide condensation techniques, and can include any combination of amino acids as desired to produce the variants described herein. Synthetic amino acids are commercially available from various companies, including but not limited to Sigma-Aldrich, Cambridge Research Biochemical, or any other chemical company familiar to those skilled in the art.

In generating variants that comprise substitutions, insertions and/or deletions at positions in addition to those described supra, the ordinarily skilled practitioner will be aware that certain regions of the endoglucanase protein are less tolerant than others to modifications (especially non-conservative substitutions). Thus, in some embodiments, endoglucanase variant polypeptides retain conserved residues and functional domains from the parent.

Endoglucanase Activity, Thermostability, and Viscosity Reduction Assays

Endoglucanase activity, thermostability, and viscosity reduction activity can be determined by methods described in the Examples section (e.g., Examples 3 and 5), and/or using any other methods known in the art. Endoglucanase activity may be determined, for example, using a para-nitrophenyl-β-D-cellobioside (pNPC)-based assay, using a cellulose assay, or using a dye-based cellulose assay.

For example, endoglucanase activity can be determined using a para-nitrophenyl-β-D-cellobioside (pNPC)-based assay. In an exemplary assay, in a total volume of 150 μL, 50 μL clear media supernatant containing endoglucanase enzyme is added to 5 mM pNPC (from Sigma) solution in 25 mM sodium acetate buffer, pH 4-5. The reactions are incubated at pH 5, 50° C. or pH 4, 70° C. for 24 hrs. In a total volume of 150 μL, 20 μL (pH 5, 50° C.) or 75 μL (pH 4, 70° C.) of the reaction mixture is quenched with 1M sodium carbonate pH 11 solution. The absorbance of the solution is measured at 405 nm to determine the conversion of pNPC to p-nitrophenyl. The release of p-nitrophenol ($\epsilon$=17,700 M-1 cm-1) is measured at 405 nm to calculate EG activity. Detectable EG activity is observed under high throughput screening conditions (pH 4, 70° C.).

Endoglucanase activity may also be determined using a cellulose assay, in which the ability of the endoglucanase variants to hydrolyze a cellulose substrate, e.g., AVICEL® cellulose (available from Sigma-Aldrich, St. Louis, Mo.,) under specific temperature and/or pH conditions is measured. In one exemplary assay, biotransformation reactions are performed by mixing 60 μl clear supernatant with 40 μl of AVICEL® cellulose slurry in 340 mM sodium acetate buffer pH4.2-5.0 (final concentration: 200 g/L AVICEL® cellulose; a glass bead/well). Additionally, 50 μl of beta-glucosidase supernatant is added to the reaction mixture for the conversion of cellobiose to glucose. Biotransformation is performed at pH 4.5, 65-70° C. for an appropriate amount of time. Conversion of AVICEL® cellulose to soluble sugar oligomers can be determined by art-known means. In one approach, conversion of AVICEL® cellulose to soluble sugar oligomers is determined using a glucose oxidase and peroxidase (GOPOD) assay. GOPOD assay kits are known in the art and are readily commercially available, e.g., from Megazyme (Wicklow, Ireland). Methods for performing GOPOD assays are also known in the art; see, e.g., McCleary et al., *J. AOAC Int.* 85(5):1103-11 (2002), the contents of which are incorporated by reference herein. For the GOPOD assay, soluble sugar oligomer production is measured by mixing 10 μl of the above reaction with 190 μl of GOPOD assay mix. The reactions are allowed to shake for 30 min at room temperature. Absorbance of the solution is measured at 510 nm to determine the amount of glucose produced in the original AVICEL® cellulose biotransformation reaction. The amount of glucose produced is measured at 510 nm to calculate endoglucanase activity.

Endoglucanase activity may also be determined using a dyed cellulose assay, in which the ability of the endoglucanase variants to hydrolyze a dyed cellulose substrate e.g., AZCL-HE-Cellulose (Azurine crosslinked hydroxy ethyl cellulose) under specific temperature and/or pH conditions is measured. In one exemplary assay, in a total volume of 220 μL, 40 μL of diluted clear media supernatant containing endoglucanase enzyme is added to 180 μl slurry containing 2 g/L AZCL-HE-Cellulose in 300 mM sodium acetate buffer (pH 4-5). The reaction is incubated at 50-70° C. for an appropriate time (up to 24 hours, depending on the enzyme concentration). After the required time period, reactions are filtered to remove insoluble oligomers. The absorbance of the clarified solution is measured at 490 nm. Degradation of AZCL-HE-Cellulose and the extent of soluble dye release is used as a measure of AZCL-HE-Cellulose-degrading activity of endoglucanase. The dyed cellulose AZCL-HE-Cellulose is readily available commercially from Megazyme (Wicklow, Ireland).

Thermostability can be determined, for example, by exposing the endoglucanase variants and the reference (e.g., wild-type) endoglucanase to stress conditions of elevated temperature and/or low pH for an appropriate period of time and then determining residual endoglucanase activity using a method described herein or using any method known in the art. In an exemplary assay, thermoactivity is screened using a cellulose-based High Throughput Assay. In deep, 96-well microtiter plates 75 μL of media supernatant containing C1 endoglucanase variant is added to 75 μL of 200 g/L microcrystalline cellulose (e.g., AVICEL® cellulose, from Sigma-Aldrich) in 300 mM sodium acetate buffer pH 4.0-5.0. After sealing with aluminum/polypropylene laminate heat seal tape (Velocity 11 (Menlo Park, Calif.), Cat#06643-001)), the plates are incubated and shaken at 60-70° C. for up to 24 hrs. The reactions are diluted by adding 150 μL of water into the deep well plates. The plates are centrifuged at 4000 rpm for 5 minutes. 150 μL of supernatant from the reaction mixture is filtered with a 0.45 μm low-binding hydrophilic PTFE filter plate (Millipore, Billerica, Mass.). The sample plates are sealed with heat seal tape to prevent evaporation. Beta-glucosidase, which converts cellobiose to glucose, is subsequently added and conversion of microcrystalline cellulose (e.g., AVICEL®) to soluble sugar oligomers is measured by GOPOD assay. GOPOD assay kits are known in the art and are readily commercially available, e.g., from Megazyme (Wicklow, Ireland). Soluble sugar oligomer production is measured by mixing 10 μl of the above reaction with 190 μl of GOPOD assay mix. The reactions are allowed to shake for 30 min at room temperature. Absorbance of the solution is measured at 510 nm to determine the amount of glucose produced in the original micro cellulose (e.g., AVICEL® cellulose) biotransformation reaction. The amount of glucose produced is measured at 510 nm to calculate endoglucanase activity.

Viscosity reduction activity can be determined, for example, by providing a substrate (e.g., cellulosic biomass) to a reference endoglucanase and endoglucanase variants under specific temperature and/or pH conditions and then measuring the viscosity of the reaction mixture (e.g., by using a viscometer) at defined time periods. In one approach, viscosity reduction activity is measured using a RVA-super4 viscometer (Pertren Instruments, Sweden). A reaction mixture comprising the substrate and the endoglucanase variant enzyme is loaded onto the RVA-Super 4 viscometer. The reaction mixture is carried out by stirring the mixture with a stirring paddle at 500 rpm for 30 seconds, then at 80 rpm for a total test time of 30 minutes. The viscosity of the reaction mixture is calculated in comparison to base viscosity, which is measured from samples lacking any enzyme.

Some endoglucanase variants of the present invention will have at least one improved property (e.g., activity) as compared to a reference sequence. In some embodiments, an endoglucanase variant has improved thermostability, improved thermoactivity, or improved viscosity reduction at a pH range of about 3.0 to about 7.5, at a pH range of about 3.5 to about 6.5, at a pH range of about 3.5 to about 6.0, at a pH range of about 3.5 to about 5.5, at a pH range of about 3.5 to about 5.0, or at a pH range of about 4.0 to about 5.0. In some embodiments, an endoglucanase variant has improved thermostability, improved thermoactivity, and/or improved viscosity reduction at a temperature of about 55° C. to about 80° C., at a temperature of about 60° C. to about 80° C., at a temperature of about 65° C. to about 80° C., or at a temperature of about 65 to about 75° C. In some embodiments, an endoglucanase variant will have improved thermostability, improved thermoactivity, or improved viscosity reduction at a pH of about 3.5 to about 5.0 and a temperature of about 65 to about 80° C.

In some embodiments, the endoglucanase variants of the invention exhibit endoglucanase activity that is at least about 1.5 fold, at least about 2.0 fold, at least about 3.0 fold, at least about 4.0 fold, at least about 5.0 fold, at least about 6.0 fold, at least about 7.0 fold, at least about 8.0 fold and at least about 10 fold greater than the endoglucanase activity of a control endoglucanase (e.g., the wild-type endoglucanase of SEQ ID NO: 1) when tested under the same conditions. In some embodiments, the stability (half-life) of the endoglucanase variants at pH about 4.5 and about 70° C. will be at least about 1.5 fold, at least about 2.0 fold, at least about 3.0 fold, at least about 4.0 fold, at least about 5.0 fold, at least about 10 fold, at least about 20 fold, at least about 50 fold, about 100 fold, or greater than the stability of a control endoglucanase (e.g., the wild-type endoglucanase of SEQ ID NO: 1) under the same conditions. In some embodiments, the viscosity reduction of the endoglucanase variants at pH about 4.5 and about 75° C. will be at least about 1.5 fold, at least about 2.0 fold, at least about 3.0 fold, at least about 4.0 fold, at least about 5.0 fold, at least about 6.0 fold, or greater than the viscosity reduction of a control endoglucanase (e.g., the wild-type endoglucanase of SEQ ID NO: 1) under the same conditions.

Signal Peptides

In general, the endoglucanase variant polypeptides of the present invention are secreted from the host cell in which they are expressed (e.g., a yeast or fungal cell) and are expressed as a pre-protein including a signal peptide, e.g., an amino acid sequence linked to the amino terminus of a polypeptide and which directs the encoded polypeptide into the cell secretory pathway. In some embodiments, the signal peptide is an endogenous *M. thermophila* (e.g., C1) endoglucanase signal peptide. In some other embodiments, signal peptides from other *M. thermophila* (e.g., C1) secreted proteins are used.

Still other signal peptides may be used, depending on the host cell and other factors. Effective signal peptide coding regions for filamentous fungal host cells include, but are not limited to, the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase, *Humicola lanuginosa* lipase, and *T. reesei* cellobiohydrolase II (TrCBH2).

Effective signal peptide coding regions for bacterial host cells include, but are not limited to the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are known in the art, such as those described by Simonen and Palva, 1993, *Microbiol Rev* 57: 109-137 (incorporated herein by reference).

Useful signal peptides for yeast host cells also include, but are not limited to those from the genes for *Saccharomyces cerevisiae* alpha-factor, *Saccharomyces cerevisiae* SUC2 invertase (see Taussig and Carlson, 1983, *Nucleic Acids Res* 11:1943-54; SwissProt Accession No. P00724), and others. See, e.g., Romanos et al., 1992, *Yeast* 8:423-488. Variants of these signal peptides and other signal peptides are suitable for use in the present invention.

Cellulose Binding Domains

Endoglucanases and other cellulases generally have a multidomain structure comprising a catalytic domain (CD) and a cellulose binding domain (CBD) joined by a linker peptide. For example, the endoglucanase of SEQ ID NO:1 comprises a CBD at amino acids 4-32 and a CD at amino acids 80-350. In some embodiments the endoglucanase of the present invention lacks a CBD. For example, in some embodiments the CBD of the endoglucanase is cleaved from the catalytic domain following secretion of the enzyme. Alternatively, engineered endoglucanases lacking a CBD may be used.

CBDs may be homologous or heterologous to the catalytic domain. A homologous CBD is associated in the wild-type endoglucanase with the parental catalytic domain. For example, the C1 endoglucanase 2 CDB is homologous to the C1 endoglucanase 2 catalytic domain. In some embodiments, the CBD is chimeric, while in some other embodiments, multiple CBDs are provided in tandem.

Fusion Peptides and Additional Sequence Elements

In some embodiments, an endoglucanase variant of the present invention further comprises additional sequences which do not alter the encoded activity of the endoglucanase. For example, the endoglucanase may be linked to an epitope tag or to another sequence useful in endoglucanase purification.

The present invention also provides endoglucanase variant fusion polypeptides, wherein the fusion polypeptide comprises an amino acid sequence encoding an endoglucanase variant polypeptide of the present invention or fragment thereof, linked either directly or indirectly through the N- or C-terminus of the endoglucanase variant polypeptide to an amino acid sequence encoding at least a second (additional) polypeptide. The endoglucanase variant fusion polypeptide may further include amino acid sequence encoding a third, fourth, fifth, or additional polypeptides. Typically, each additional polypeptide has a biological activity, or alternatively, is a portion of a polypeptide that has a biological activity, where the portion has the effect of improving expression and/or secretion of the fusion polypeptide from the desired expression host. These sequences may be fused, either directly or indirectly, to the N- or C-terminus of the endoglucanase variant polypeptide or fragment thereof, or alternatively, to the N- or C-terminus of the additional polypeptides having biological activity.

In some embodiments, the additional polypeptide(s) encode an enzyme or active fragment thereof, and/or a polypeptide that improves expression and/or secretion of the fusion polypeptide from the desired expression host cell. For example, the additional polypeptide may encode a cellulase (for example, an endoglucanase having a different amino acid sequence from the endoglucanase variant polypeptide in the fusion polypeptide, or a polypeptide exhibiting exoglucanase activity or β-glucosidase activity) and/or a polypeptide that improves expression and secretion from the desired host cell, such as, for example, a polypeptide that is normally expressed and secreted from the desired expression host, such as a secreted polypeptide normally expressed from filamentous fungi. These include, but are not limited to glucoamylase, α-amylase and aspartyl proteases from *Aspergillus niger, Aspergillus niger* var. *awamori*, and *Aspergillus oryzae*, cellobiohydrolase I, cellobiohydrolase II, endoglucanase I and endoglucanse III from *Trichoderma* and glucoamylase from *Neurospora* and *Humicola* species. See WO 98/31821, which is incorporated herein by reference.

The polypeptide components of the fusion polypeptide may be linked to each other indirectly via a linker. Linkers suitable for use in the practice of the present invention are described in WO 2007/075899, which is incorporated herein by reference. Exemplary linkers include peptide linkers of from about 1 to about 40 amino acid residues in length, including those from about 1 to about 20 amino acid residues in length, and those from about 1 to about 10 amino acid residues in length. In some embodiments, the linkers may be made up of a single amino acid residue, such as, for example, a Gly, Ser, Ala, or Thr residue or combinations thereof, particularly Gly and Ser. Linkers employed in the practice of the present invention may be cleavable. Suitable cleavable linkers may contain a cleavage site, such as a protease recognition site. Exemplary protease recognition sites are well known in the art and include (but are not limited to), for example, Lys-Arg (the KEX2 protease recognition site, which can be cleaved by a native *Aspergillus* KEX2-like protease), Lys and Arg (the trypsin protease recognition sites). See, for example, WO 2007/075899, which is incorporated herein by reference.

III. Endoglucanase Variant Polynucleotides and Expression Systems

In another aspect, the present invention provides polynucleotides encoding the variant endoglucanase polypeptides as described herein. The polynucleotide may be operatively linked to one or more heterologous regulatory or control sequences that control gene expression to create a recombinant polynucleotide capable of expressing the polypeptide. Expression constructs containing a heterologous polynucleotide encoding the engineered endoglucanase can be introduced into appropriate host cells to express the corresponding endoglucanase.

In some embodiments, the endoglucanase variant is generated from a wild-type *M. thermophila* endoglucanase cDNA sequence, or the portion thereof comprising the open reading frame, with changes made as required at the codons corresponding to substitutions (residues mutated relative to the wild-type sequence as described herein, for example at Tables 2-5). In addition, one or more of the "silent" nucleotide changes shown in any of Tables 2-5 can be incorporated.

In other embodiments, non-naturally occurring sequences are preferred. Those having ordinary skill in the art will understand that due to the degeneracy of the genetic code, a multitude of nucleotide sequences encoding endoglucanase polypeptides of the present invention exist. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

A DNA sequence may also be designed for high codon usage bias codons (e.g., codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available See e.g., Henaut and Danchin in "*Escherichia Salmonella*," Neidhardt, et al. Eds., ASM Pres, Washington D.C. (1996), pp. 2047-2066, which is incorporated herein by reference. For illustration, and not for limitation, SEQ ID NO:2 shows a *M. thermophila* endoglucanase-encoding polynucleotide sequence designed with codon biasing for expression in *Saccharomyces cerevisiae*.

Polynucleotides encoding endoglucanase can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al., 1981, *Tetrahedron Letters*, 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. See, e.g., Carruthers, et al., 1982, *Cold Spring Harbor Symp. Quant. Biol.,* 47:411-18 and Adams et al., 1983, *J. Am. Chem. Soc.* 105:661, both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2009) ("Ausubel"), all of which are incorporated herein by reference. Reference is made to Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomeli et al. (1989) *J. Clin. Chem* 35, 1826; Landegren et al., (1988) *Science* 241, 1077-1080; Van Brunt (1990) *Biotechnology* 8, 291-294; Wu and Wallace, (1989) Gene 4, 560; Barringer et al. (1990) *Gene* 89, 117, and Sooknanan and Malek (1995) *Biotechnology* 13: 563-564, all of which are incorporated herein by reference. Methods for cloning in vitro amplified nucleic acids are described in Wallace et al., U.S. Pat. No. 5,426,039, which is incorporated herein by reference.

Vectors

The present invention makes use of recombinant constructs comprising a sequence encoding an endoglucanase as described above. In a particular aspect the present invention provides an expression vector comprising an endoglucanase polynucleotide operably linked to a heterologous promoter. Expression vectors of the present invention may be used to transform an appropriate host cell to permit the host to express the endoglucanase protein. Methods for recombinant expression of proteins in fungi and other organisms are well known in the art, and a number expression vectors are available or can be constructed using routine methods. See, e.g., Tkacz and Lange, 2004, *Advances in fungal biotechnology for industry, agriculture, and medicine,* Kluwer academic/Plenum Publishers. New York; Zhu et al., 2009, Construction of two Gateway vectors for gene expression in fungi *Plasmid* 6:128-33; Kavanagh, K. 2005, *Fungi: biology and applications*; Wiley, all of which are incorporated herein by reference.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include, but are not limited to chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

In some embodiments, the construct further comprises regulatory sequences, including, for example, a promoter, operably linked to the protein encoding sequence. Large numbers of suitable vectors and promoters are known to those of skill in the art.

Promoters

In order to obtain high levels of expression in a particular host it is often useful to express *M. thermophila* (e.g., C1) endoglucanase under control of a heterologous promoter. A promoter sequence may be operably linked to the 5' region of the *M. thermophila* (e.g., C1) endoglucanase coding sequence using routine methods.

Examples of useful promoters for expression of endoglucanase polynucleotides include, but are not limited to promoters from fungi. For example, promoter sequences that drive expression of genes other than the endoglucanase gene in *M. thermophila* may be used. For example, a fungal promoter from a gene encoding cellobiohydrolase may be used.

Examples of useful promoters for expression of cellobiohydrolases include promoters from fungi. In some embodiments, a promoter sequence that drives expression of a gene other than an endoglucanase gene in a fungal strain may be used. As a non-limiting example, a fungal promoter from a gene encoding a cellobiohydrolase may be used. In some embodiments, a promoter sequence that drives the expression of an endoglucanase gene in a fungal strain other than the fungal strain from which the endoglucanase variant was derived may be used. As a non-limiting example, if the endoglucanase variant is derived from *M. thermophila* (e.g., C1), a promoter from a *T. reesei* endoglucanase gene may be used or a promoter as described in WO2010107303, such as but not limited to the sequences identified as SEQ ID NO:25, SEQ ID NO:26, SEQ ID NO:27, SEQ ID NO:28, or SEQ ID NO:29 in WO2010107303.

Examples of other suitable promoters useful for directing the transcription of the nucleotide constructs of the present invention in a filamentous fungal host cell include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (Nunberg et al., 1984, *Mol. Cell Biol.,* 4:2306-2315, Boel et al., 1984, *EMBO J.* 3:1581-

85 and EPA 137280, all of which are incorporated herein by reference), and mutant, truncated, and hybrid promoters thereof. In a yeast host, useful promoters include, but are not limited to those from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are described by Romanos et al., 1992, *Yeast* 8:423-488, incorporated herein by reference. Promoters associated with chitinase production in fungi may be used. See, e.g., Blaiseau and Lafay, 1992, *Gene* 120243-248 (filamentous fungus *Aphanocladium album*); Limon et al., 1995, *Curr. Genet,* 28:478-83 (*Trichoderma harzianum*), both of which are incorporated herein by reference.

In a yeast host, useful promoters include, but are not limited to those from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423-88.

Any other promoter sequence that drives expression in a suitable host cell may be used. Suitable promoter sequences can be identified using well known methods. In one approach, a putative promoter sequence is linked 5' to a sequence encoding a reporter protein, the construct is transfected into the host cell (e.g., C1) and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (Henriksen et al, 1999, *Microbiology* 145:729-34, incorporated herein by reference) or a lacZ reporter gene (Punt et al, 1997, *Gene,* 197:189-93, incorporated herein by reference). Functional promoters may be derived from naturally occurring promoter sequences by directed evolution methods. See, e.g. Wright et al., 2005, *Human Gene Therapy,* 16:881-892, incorporated herein by reference.

Other Expression Elements

Cloned endoglucanases may also have a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells include, but are not limited to those obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells include but are not limited to those obtained from the genes for *Saccharomyces cerevisiae* enolase, *Saccharomyces cerevisiae* cytochrome C (CYCI), and *Saccharomyces cerevisiae* glyceraldehyde-3-phosphate dehydrogenase. Other useful terminators for yeast host cells are described by Romanos et al., 1992, *Yeast* 8:423-88.

A suitable leader sequence may be part of a cloned endoglucanase sequence, which is a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells include, but are not limited to those obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

Sequences may also contain a polyadenylation sequence, which is a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells include, but are not limited to those from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, *Mol Cell Bio* 15:5983-5990 (1995).

In some embodiments, the expression vector of the present invention preferably contains one or more selectable markers, which permit easy selection of transformed cells. A selectable marker is a gene, the product of which provides for biocide or viral resistance, resistance to heavy metals, prototrophy to auxotrophs, and the like. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Suitable markers for yeast host cells are ADE2, HIS3, LEU2, LYS2, MET3, TRP1, and URA3.

Expression Hosts

The sequence encoding an endoglucanase is transformed into a host cell in order to allow propagation of the endoglucanase vector and expression of the endoglucanase. In some embodiments, the endoglucanase is post-translationally modified to remove the signal peptide and in some cases may be cleaved after secretion.

The transformed or transfected host cell described above is cultured in a suitable nutrient medium under conditions permitting the expression of the endoglucanase. The medium used to culture the cells may be any conventional medium suitable for growing the host cells, such as minimal or complex media containing appropriate supplements. Cells are optionally grown in HTP media. Suitable media are available from commercial suppliers or may be prepared according to published recipes (e.g. in catalogues of the American Type Culture Collection).

In some embodiments, the host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. In some embodiments, fungal host cells are yeast cells and filamentous fungal cells. The filamentous fungi host cells of the present invention include all filamentous forms of the subdivision Eumycotina and Oomycota. (Hawksworth et al., In Ainsworth and Bisby's Dictionary of The Fungi, 8$^{th}$ edition, 1995, CAB International, University Press, Cambridge, UK). Filamentous fungi are characterized by a vegetative mycelium with a cell wall composed of chitin, cellulose and other complex polysaccharides. The filamentous fungi host cells of the present invention are morphologically distinct from yeast.

In the present invention a filamentous fungal host cell may be a cell of any suitable genus, including but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms or taxonomic equivalents thereof.

In some embodiments of the invention, the filamentous fungal host cell is a *Trichoderma* species, e.g., *T. longibrachiatum, T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof; see Sheir-Neiss et al., Appl. Microbiol. Biotechnology, 20 (1984) pp 46-53), *T. koningii*, and *T. harzianum*. In addition, the term "*Trichoderma*" refers to any fungal strain that was previously classified as *Trichoderma* or is currently classified as *Trichoderma*. In some embodiments of the invention, the filamentous fungal host cell is an *Aspergillus* species, e.g., *A. awamori, A. funigatus, A. japonicus, A. nidulans, A. niger, A. aculeatus, A. foetidus, A. oryzae, A. sojae*, and *A. kawachi*. (Reference is made to Kelly and Hynes (1985) *EMBO J.* 4,475479; NRRL 3112, ATCC 11490, 22342, 44733, and 14331; Yelton M., et al., (1984) *Proc. Natl. Acad. Sci. USA*, 81, 1470-1474; Tilburn et al., (1982) *Gene* 26, 205-221; and Johnston, I. L. et al. (1985) *EMBO J.* 4, 1307-1311). In some embodiments of the invention, the filamentous fungal host cell is a *Chrysosporium* species, e.g., *C. lucknowense, C. keratinophilum, C. tropicum, C. merdarium, C. inops, C. pannicola*, and *C. zonatum*. In some embodiments of the invention, the filamentous fungal host cell is a *Myceliophthora* species, e.g., *M. thermophilia*. In some embodiments of the invention, the filamentous fungal host cell is a *Fusarium* species, e.g., *F. bactridioides, F. cerealis, F. crookwellense, F. culmorum, F. graminearum, F. graminum. F. oxysporum, F. roseum*, and *F. venenatum*. In some embodiments of the invention, the filamentous fungal host cell is a *Neurospora* species, e.g., *N. crassa*. Reference is made to Case, M. E. et al., (1979) *Proc. Natl. Acad. Sci. USA*, 76, 5259-5263; U.S. Pat. No. 4,486,553; and Kinsey, J. A. and J. A. Rambosek (1984) *Molecular and Cellular Biology* 4, 117-122. In some embodiments of the invention, the filamentous fungal host cell is a *Humicola* species, e.g., *H. insolens, H. grisea*, and *H. lanuginosa*. In some embodiments of the invention, the filamentous fungal host cell is a *Mucor* species, e.g., *M. miehei* and *M. circinelloides*. In some embodiments of the invention, the filamentous fungal host cell is a *Rhizopus* species, e.g., *R. oryzae* and *R. niveus*. In some embodiments of the invention, the filamentous fungal host cell is a *Penicillum* species, e.g., *P. purpurogenum, P. chrysogenum*, and *P. verruculosum*. In some embodiments of the invention, the filamentous fungal host cell is a *Thielavia* species, e.g., *T. terrestris*. In some embodiments of the invention, the filamentous fungal host cell is a *Tolypocladium* species, e.g., *T. inflatum* and *T. geodes*. In some embodiments of the invention, the filamentous fungal host cell is a *Trametes* species, e.g., *T. villosa* and *T. versicolor*.

In some embodiments of the present invention, any suitable yeast host cell finds use, including but not limited to cells of the genera *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In some embodiments on the invention, the host cell is an algal cell such as *Chlamydomonas* (e.g., *C. reinhardtii*) and *Phormidium* (P. sp. ATCC29409).

In some other embodiments, the host cell is a prokaryotic cell. Suitable prokaryotic cells include Gram positive, Gram negative and Gram-variable bacterial cells. For example in some embodiments, the host cell is a species of any suitable genus, including but not limited to *Agrobacterium, Alicyclobacillus, Anabaena, Anacystis, Acinetobacter, Acidothermus, Arthrobacter, Azobacter, Bacillus, Bifidobacterium, Brevibacterium, Buchnera, Campestris, Camplyobacter, Clostridium, Corynebacterium, Chromatium, Coprococcus, Escherichia, Enterococcus, Enterobacter, Erwina, Fusobacterium, Faecalibacterium, Francisella, Flavobacterium, Geobacillus Haemophilus, Helicobacter, klebsiella, Lactobacillus, Lactococcus, llyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomoras, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*. In some embodiments, the host cell is a species *of, Agrobacterium, Acinetobacter, Azobacter, Bacillus, Bifidobacterium, Buchnera, Geobacillus; Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, and *Zymomonas*.

In yet other embodiments, the bacterial host strain is non-pathogenic to humans. In some embodiments the bacterial host strain is an industrial strain. Numerous bacterial industrial strains are known and suitable for use in the present invention.

In some embodiments of the invention, the bacterial host cell is an *Agrobacterium* species, e.g., *A. radiobacter, A. rhizogenes*, and *A. rubi*. In some embodiments of the invention the bacterial host cell is an *Arthrobacter* species, e.g., *A. aurescens, A. citreus, A. globformis, A. hydrocarboglutamicus, A. mysorens, A. nicotianae, A. paraffineus, A. protophonniae, A. roseoparqffinus, A. sulfureus*, and *A. ureafaciens*. In some embodiments of the invention the bacterial host cell is a *Bacillus* species, e.g., *B. thuringiensis, B.*

*anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In some particular embodiments, the host cell is an industrial *Bacillus* strain including but not limited to *B. subtilis, B. pumilus, B. licheniformis, B. megaterium, B. clausii, B. stearothermophilus* and *B. amyloliquefaciens*. In some embodiments the bacterial host cell is a *Clostridium* species, e.g., *C. acetobutylicum, C. tetani* E88, *C. lituseburense, C. saccharobutylicum, C. perfringens,* and *C. beijerinckii*. In some embodiments the bacterial host cell is a *Corynebacterium* species e.g., *C. glutamicum* and *C. acetoacidophilum*. In some embodiments the bacterial host cell is an *Escherichia* species, e.g., *E. coli*. In some embodiments the bacterial host cell is an *Erwinia* species, e.g., *E. uredovora, E. carotovora, E. ananas, E. herbicola, E. punctata,* and *E. terreus*. In some embodiments the bacterial host cell is a *Pantoea* species, e.g., *P. citrea,* and *P. agglomerans*. In some embodiments the bacterial host cell is a *Pseudomonas* species, e.g., *P. putida, P. aeruginosa, P. mevalonii,* and P. sp. D-01 10. In some embodiments the bacterial host cell is a *Streptococcus* species, e.g., *S. equisimiles, S. pyogenes,* and *S. uberis*. In some embodiments the bacterial host cell is a *Streptomyces* species, e.g., *S. ambofaciens, S. achromogenes, S. avermitilis, S. coelicolor, S. aureofaciens, S. aureus, S. fungicidicus, S. griseus,* and *S. lividans*. In some embodiments the bacterial host cell is a *Zymomonas* species, e.g., *Z. mobilis,* and *Z. lipolytica*.

Strains which may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Host cells may be genetically modified to have characteristics that improve protein secretion, protein stability or other properties desirable for expression and/or secretion of at least one protein. For example, knockout of Alp1 function results in a cell that is protease deficient. Knockout of pyr5 function results in a cell with a pyrimidine deficient phenotype. In particular embodiments host cells are modified to delete endogenous cellulase protein-encoding sequences or otherwise eliminate expression of one or more endogenous cellulases. In one embodiment expression of one or more endogenous cellulases is inhibited to increase production of cellulases of interest. In some embodiments, the host cell for expression is a fungal cell (e.g., *Myceliophthora thermophila*) genetically modified to reduce the amount of endogenous cellobiose dehydrogenase (EC 1.1.3.4).

Genetic modification can be achieved by genetic engineering techniques or using classical microbiological techniques, such as chemical or UV mutagenesis and subsequent selection. A combination of recombinant modification and classical selection techniques may be used to produce the organism of interest. Using recombinant technology, nucleic acid molecules can be introduced, deleted, inhibited or modified, in a manner that results in increased yields of endoglucanase within the organism or in the culture. For example, knockout of Alp1 function results in a cell that is protease deficient. Knockout of pyr5 function results in a cell with a pyrimidine deficient phenotype. In one genetic engineering approach, homologous recombination can be used to induce targeted gene modifications by specifically targeting a gene in vivo to suppress expression of the encoded protein. In an alternative approach, siRNA, antisense, or ribozyme technology can be used to inhibit gene expression. See, e.g., Chaveroche et al., 2000, *Nucleic Acids Research,* 28:22 e97; Cho et al., 2006, *MPMI* 19: 1, pp. 7-15; Maruyama and Kitamoto, 2008, *Biotechnol Lett* 30:1811-1817; Takahashi et al., 2004, *Mol Gen Genomics* 272: 344-352; Rothstein, 1983, *Methods in Enzymology* 101:202-11 and You et al., 2009, *Arch Micriobiol* 191:615-622, the contents of each of which is incorporated by reference herein in its entirety. Random mutagenesis, followed by screening for desired mutations, can also be used. See e.g., Combier et al., 2003, *FEMS Microbiol Lett* 220:141-8 and Firon et al., 2003, *Eukaryot Cell* 2:247-55, incorporated by reference herein in its entirety.

Cell Transformation and Culture

Introduction of a vector or DNA construct into a host cell can be effected by calcium phosphate transfection, DEAE-Dextran mediated transfection, electroporation, or other common techniques (See Davis et al., 1986, *Basic Methods in Molecular Biology,* which is incorporated herein by reference).

The engineered host cells can be cultured in conventional nutrient media modified as appropriate for activating promoters, selecting transformants, or amplifying the endoglucanase polynucleotide. Culture conditions, such as temperature, pH and the like, are those suitable for use with the host cell selected for expression, and will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique,* third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques,* fourth edition W.H. Freeman and Company; and Ricciardelle et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Jones, ed. (1984) *Plant Gene Transfer and Expression Protocols,* Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) The Handbook of Microbiological Media (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue and supplement* (1997) also from Sigma-Aldrich, Inc (St Louis, Mo.) ("Sigma-PCCS"), all of which are incorporated herein by reference.

In some embodiments, cells expressing the endoglucanase polypeptides of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an system where a defined fermentation medium is added continuously to a bioreactor and an equal amount of conditioned medium is removed simultaneously for processing and harvesting of desired proteins. In some embodiments, continuous fermentation generally maintains the cultures at a constant high density where cells are primarily in log phase growth. In some embodiments, continuous fermentation generally maintains the cultures at a stationary, or late log/stationary, phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

Cell-free transcription/translation systems can also be employed to produce endoglucanase polypeptides using the polynucleotides of the present invention. Several such systems are commercially available. A general guide to in vitro transcription and translation protocols is found in Tymms (1995) *In vitro Transcription and Translation Protocols: Methods in Molecular Biology*, Volume 37, Garland Publishing, NY, which is incorporated herein by reference.

IV. Production and Recovery of Endoglucanase Variant Polypeptides

The present invention is directed to a method of making a polypeptide having endoglucanase activity, the method comprising providing a host cell transformed with at least one of any one of the described endoglucanase polynucleotides of the present invention; culturing the transformed host cell in a culture medium under conditions in which the host cell expresses the encoded endoglucanase polypeptide(s); and optionally recovering or isolating the expressed endoglucanase polypeptide(s), or recovering or isolating the culture medium containing the expressed endoglucanase polypeptide(s). The method further provides optionally lysing the transformed host cells after expressing the encoded endoglucanase polypeptide(s) and optionally recovering or isolating the expressed endoglucanase polypeptide(s) from the cell lysate. The present invention further provides a method of making an endoglucanase polypeptide, said method comprising cultivating a host cell transformed with an endoglucanase polynucleotide under conditions suitable for the production of the endoglucanase polypeptide and recovering the endoglucanase polypeptide.

Typically, recovery or isolation of the endoglucanase polypeptide is from the host cell culture medium, the host cell or both, using protein recovery techniques that are well known in the art, including those described herein. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. Purification of BGL1 is described in Parry et al., 2001, *Biochem. J.* 353:117, and Hong et al., 2007, *Appl. Microbiol. Biotechnol.* 73:1331, both incorporated herein by reference. In addition to the references noted supra, a variety of purification methods are well known in the art, including, for example, those set forth in Sandana (1997) *Bioseparation of Proteins*, Academic Press, Inc.; Bollag et al. (1996) *Protein Methods, 2$^{nd}$ Edition*, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and *Angal Protein Purification Methods: A Practical Approach*, IRL Press at Oxford, Oxford, England; Scopes (1993) *Protein Purification: Principles and Practice 3$^{rd}$ Edition*, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference.

Immunological methods may be used to purify endoglucanase polypeptides. In one approach, antibody raised against the endoglucanase polypeptides (e.g., against a polypeptide comprising SEQ ID NO:1 or an immunogenic fragment thereof) using conventional methods is immobilized on beads, mixed with cell culture media under conditions in which the endoglucanase is bound, and precipitated. In a related approach, immunochromatography is used.

As noted, in some embodiments the endoglucanase is expressed as a fusion protein including a non-enzyme portion. In some embodiments the endoglucanase sequence is fused to a purification facilitating domain. As used herein, the term "purification facilitating domain" refers to a domain that mediates purification of the polypeptide to which it is fused. Suitable purification domains include metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; Wilson et al., 1984, *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the HHDH polypeptide is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al., 1992, *Protein Expression and Purification* 3:263-281) while the enterokinase cleavage site provides a means for separating the HHDH polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

V. Methods of Using Endoglucanase Variant Polypeptides

The endoglucanase variants as described herein have multiple industrial applications, including but not limited to, sugar production (e.g. glucose syrups), biofuels production, textile treatment, pulp or paper treatment, detergents, personal care compositions, food, and/or animal feed. A host cell containing an endoglucanase variant of the present invention may be used without recovery and purification of the recombinant endoglucanase, e.g., for use in a large scale biofermentor. Alternatively, the recombinant endoglucanase may be expressed and purified from the host cell. The endoglucanase variants of the present invention may also be used according to the methods of Section III ("Improved Saccharification Process") of International Patent Application No. PCT/US2010/029509, published as WO 2010/120557, the contents of which are incorporated by reference herein.

The variant endoglucanases that have been described herein are particularly useful for breaking down cellulose to smaller oligosaccharides, disaccharides and monosaccharides. In some embodiments, the variant endoglucanases are useful in saccharification methods. In some embodiments, the variant endoglucanases may be used in combination with other cellulase enzymes including, for example, conventional enzymatic saccharification methods, to produce soluble sugars.

In some embodiments, the endoglucanase variants of the present invention are useful in saccharification processes in which the endoglucanase variant is combined with cellulosic biomass in an initial saccharification process, producing soluble sugars that can subsequently be treated with other cellulase enzymes. Alternatively, the endoglucanase variants may be used in combination with other cellulase enzymes including, for example, conventional enzymatic saccharification methods, to produce soluble sugars.

Any suitable temperature, pH and incubation conditions for utilization of the endoglucanase variants of the present invention find use. In embodiments, the endoglucanase enzyme compositions may be reacted with a biomass substrate in the range of about 25° C. to about 100° C., about 30° C. to about 90° C., about 30° C. to about 80° C., and about 30° C. to about 70° C. Also the biomass may be reacted with the endoglucanase enzyme compositions at about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. Generally, the pH range will be from about pH 3.0 to about 8.5, about pH 3.5 to about 8.5, about pH 4.0 to about 7.5, about pH 4.0 to about 7.0 and about pH 4.0 to about 6.5. The incubation time may vary for example from about 1.0 to about 240 hours, from about 5.0 to about 180 hrs and from about 10.0 to about 150 hrs. For example, in some embodiments, the incubation time will be at least about 1 hr, at least about 5 hrs, at least about 10 hrs, at least about 15 hrs, at least about 25 hrs, at least about 50 hr, at least about 100 hrs, at least about 140 hours, at least about 180, at least about 200 hours, at least about 220 hours, at least about 240 hours, and the like. Incubation of the endoglucanse-containing compositions under these conditions may result in the release of substantial amounts of soluble sugars from the substrate. For example at least about 20%, at least about 30%, at least about 40%, at least about 50%, at least about 60%, at least about 70%, at least about 75%, at least about 80%, at least about 85%, at least about 90% or more soluble sugar may be available when the endoglucanse variants of the present invention are used, as compared to the release of sugar by a parent (e.g., wild-type) polypeptide.

The endoglucanase enzyme can be combined with a biomass substrate in enriched or purified form, such as an acellular composition optionally comprising other cellulases and/or other enzyme mixtures. In an alternative embodiment cells expressing (e.g., secreting) the endoglucanase enzyme can be combined in culture with the biomass substrate. In some embodiments the cell is a cellulase-engineered cell expressing at least one cellulase enzyme in addition to the endoglucanase.

In one aspect the invention provides a method of producing an end-product from a cellulosic substrate by (a) contacting the cellulosic substrate with at least one cellobiohydrolase, at least one β-glucosidase, at least one variant endoglucanase and, optionally, at least one GH61 protein, under conditions in which soluble sugars are produced; and (b) contacting the soluble sugars with a microorganism, such as a yeast, in a fermentation to produce the end-product. Examples of end-products include, but are not limited to alcohols (e.g., ethanol and butanol), fatty alcohols (e.g., C8-C20 fatty alcohols), acids (e.g., lactic acid, 3-hydroxypropionic acid, acrylic acid, acetic acid, succinic acid, citric acid, malic acid, fumaric acid, amino acids, etc.), 1,3-propane diol, ethylene glycol, glycerol, terpenes, and antimicrobials (e.g., β-lactams such as cephalosporin). In some embodiments in which ethanol is produced by fermentation, other products, including but not limited to lactate, acetic acid, hydrogen and carbon dioxide are also produced. As noted above, in some cases a simultaneous saccharification and fermentation process is used.

Any suitable micro-organism may be used to convert sugar in the sugar hydrolysate to ethanol or other fermentation products. These include yeast from the genera Saccharomyces, Hansenula, Pichia, Kluyveromyces and Candida. Commercially available yeasts may be used, such as ETHANOL RED® yeast, SAFDISTIL® yeast, THERMOSACC® yeast, FERMIOL®, yeast, FERMIVIN® yeast, or SUPERSTART™ yeast. The sugar hydrolysate may also be supplemented with additional nutrients required for growth and fermentation performance of the fermentation microorganism. For example, yeast extract, specific amino acids, phosphate, nitrogen sources, salts, trace elements and vitamins (Verduyn et al., 1992, Yeast 8(7):501-170, Jørgensen, 2009, Appl Biochem Biotechnol, 153:44-57 and Zhao et al., 2009, Journal of Biotechnology, 139:55-60) may be included in the nutrient medium. In some embodiments, the fermentation is conducted under anaerobic conditions, although aerobic or microaerobic conditions may also be used.

The yeast may be genetically engineered to ferment both hexose and pentose sugars to at least one end-product, including but not limited to ethanol. Alternatively, the yeast may be a strain that has been made capable of xylose and glucose fermentation by one or more non-recombinant methods, such as adaptive evolution or random mutagenesis and selection. For example, the fermentation may be performed with recombinant Saccharomyces. The recombinant yeast may be a strain that has been made capable of xylose fermentation by recombinant incorporation of genes encoding xylose reductase (XR) and xylitol dehydrogenase (XDH) (U.S. Pat. Nos. 5,789,210, 5,866,382, 6,582,944 and 7,527,927 and EP 450 530) and/or gene(s) encoding one or more xylose isomerase (XI) (U.S. Pat. Nos. 6,475,768 and 7,622,284). In addition, the modified yeast strain may overexpress an endogenous or heterologous gene encoding xylulokinase (XK). Other yeast can ferment hexose and pentose sugars to at least one end-product, including but not limited to ethanol, such as yeast of the genera *Hansenula, Pichia, Kluyveromyces* and *Candida* (WO 2008/130603).

The variant endoglucanases of the present invention may be utilized in any method used to generate alcohols or other end-products from cellulose, and are not limited necessarily to those described herein. Two methods commonly employed are the separate saccharification and fermentation (SHF) method (see, Wilke et al., Biotechnol. Bioengin. 6:155-75 (1976)) or the simultaneous saccharification and fermentation (SSF) method disclosed for example in U.S. Pat. Nos. 3,990,944 and 3,990,945.

The SHF method of saccharification comprises the steps of contacting a cellulase with a cellulose containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol.

In addition to SHF methods, a SSF method may be used. In some cases, SSF methods result in a higher efficiency of alcohol production than is afforded by the SHF method (Drissen et al., Biocatalysis and Biotransformation 27:27-35 (2009). One disadvantage of SSF over SHF is that higher temperatures are required for SSF than for SHF. In one embodiment, the present invention provides EG polypeptides that have higher thermo-stability than a reference EG and one practicing the present invention could expect an increase in ethanol production if using the EGs described here in SSF methods.

In some embodiments, for cellulosic substances to be used effectively as substrates for the saccharification reaction in the presence of a variant endoglucanses of the present invention, it is desirable to pretreat the substrate. Means of pretreating a cellulosic substrate are known in the art and the present invention is not limited by such methods.

Any alcohol producing microorganism such as those known in the art, e.g., *Saccharomyces cerevisiae*, can be employed with the present invention for the fermentation of fermentable sugars to alcohols and other end-products.

The fermentable or soluble sugars produced from the use of one or more endoglucanase variants encompassed by the invention may be used to produce other end-products besides alcohols, such as but not limited to other biofuels compounds, acetone, amino acids, organic acids, glycerol, ascorbic acid, 1,3-propanediol and other chemicals.

Endoglucanases are also useful for reducing the degree of polymerization of a cellulose chain. Thus, in some embodiments, the endoglucanase variants of the present invention are useful for methods of reducing the degree of polymerization of a cellulosic substrate. In some embodiments, the methods comprise contacting the cellulosic substrate with an endoglucanase variant under conditions in which a cellulosic substrate with a lower degree of polymerization is produced.

In some embodiments, the endoglucanase variants of the present invention are useful for methods of producing cellodextrin molecules (e.g., cellobiose, cellotriose, cellotetrose, cellopentose, and cellohexose) from a cellulosic substrate. In some embodiments, the methods comprise contacting the cellulosic substrate with an endoglucanase variant under conditions in which the cellodextrin molecules are produced.

Endoglucanases as described herein are further useful in the pulp and paper industry. In the pulp and paper industry, neutral cellulases can be used, for example, in deinking of different recycled papers and paperboards having neutral or alkaline pH, in improving the fiber quality, or increasing the drainage in paper manufacture. Other exemplary uses include the removal of printing paste thickener and excess dye after textile printing.

Enzyme Mixtures

In another aspect, the invention provides an enzyme mixture that comprises at least one *M. thermophila* (e.g., C1) endoglucanase variant polypeptide as described herein. The enzyme mixture may be cell-free, or in alternative embodiments, may not be separated from host cells that secrete an enzyme mixture component. A cell-free enzyme mixture typically comprises enzymes that have been separated from cells. Cell-free enzyme mixtures can be prepared by any of a variety of methodologies that are known in the art, such as filtration or centrifugation methodologies. In certain embodiments, the enzyme mixture can be, for example, partially cell-free, substantially cell-free, or entirely cell-free.

The *M. thermophila* (e.g., C1) endoglucanase variant(s) and any additional enzymes present in the enzyme mixture may be secreted from a single genetically modified fungal cell or by different microbes in combined or separate fermentations. Similarly, the *M. thermophila* (e.g., C1) endoglucanase variant(s) and any additional enzymes present in the enzyme mixture may be expressed individually or in sub-groups from different strains of different organisms and the enzymes combined in vitro to make the enzyme mixture. It is also contemplated that the *M. thermophila* (e.g., C1) endoglucanase variant(s) and any additional enzymes in the enzyme mixture may be expressed individually or in sub-groups from different strains of a single organism, and the enzymes combined to make the enzyme mixture. In some embodiments, all of the enzymes are expressed from a single host organism, such the genetically modified fungal cell.

In some embodiments, the enzyme mixture comprises at least one additional type of cellulase, selected from CBH, EG, and BGL cellulases. In some embodiments, the cellobiohydrolase is *T. reesei* cellobiohydrolase II. In some embodiments, the endoglucanase comprises a catalytic domain derived from the catalytic domain of a *Streptomyces avermitilis* endoglucanase. See, copending U.S. application Ser. No. 12/751,985 (published as US 2010/0267089), incorporated herein by reference. In some embodiments, the enzyme mixtures comprise at least one cellulase from *Acidothermus cellulolyticus, Thermobifida fusca, Humicola grisea,* or a *Chrysosporium* sp. In some embodiments, cellulase enzymes of the cellulase mixture work together resulting in decrystallization and hydrolysis of the cellulose from a biomass substrate to yield soluble sugars, such as but not limited to glucose (See Brigham et al., 1995, in Handbook on Bioethanol (C. Wyman ed.) pp 119-141, Taylor and Francis, Washington D.C., which is incorporated herein by reference).

Cellulase mixtures for efficient enzymatic hydrolysis of cellulose are known (see, e.g., Viikari et al., 2007, "Thermostable enzymes in lignocellulose hydrolysis" Adv Biochem Eng Biotechnol 108:121-45, and US Pat. publications US 2009/0061484; US 2008/0057541; and US 2009/0209009 to Iogen Energy Corp.), each of which is incorporated herein by reference for all purposes. In some embodiments, mixtures of purified naturally occurring and/or recombinant enzymes are combined with cellulosic feedstock or a product of cellulose hydrolysis. Alternatively or in addition, one or more cell populations, each producing one or more naturally occurring or recombinant cellulases, may be combined with cellulosic feedstock or a product of cellulose hydrolysis.

In some embodiments, at least one endoglucanase variant polypeptide of the invention may be present in mixtures with additional cellulase enzymes.

GH 61 proteins enhance the yield of enhance the breakdown of lignocellulose when used in conjunction with one or more cellulases. In some additional embodiments one or more GH61 proteins are present in combination with the endoglucanase variants provided herein. In some additional embodiments, at least one GH61 enzyme is included in mixtures comprising the endoglucanase variants provided herein and any additional desired cellulases and/or other enzymes (e.g., lipases, proteases, amylases, glucoamylases, etc.). See, e.g., copending application Ser. No. 13/215,193, which is incorporated herein by reference in its entirety.

An endoglucanase variant polypeptide of the invention may also be present in mixtures with non-cellulase enzymes described below that degrade cellulose, hemicellulose, pectin, and/or lignocellulose and/or have other activities.

A "hemicellulase" as used herein, refers to a polypeptide that can catalyze hydrolysis of hemicellulose into small polysaccharides such as oligosaccharides, or monomeric saccharides. Hemicellulloses include xylan, glucuonoxylan, arabinoxylan, glucomannan and xyloglucan. Hemicellulases include, for example, the following: endoxylanases, β-xylosidases, α-L-arabinofuranosidases, a-D-glucuronidases, feruloyl esterases, coumarolyl esterases, α-galactosidases, β-galactosidases, β-mannanases, and β-mannosidases. An enzyme mixture may therefore comprise a β-glucosidase variant of the invention and one or more hemicellulases.

An endoxylanase (EC 3.2.1.8) catalyzes the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

A β-xylosidase (EC 3.2.1.37) catalyzes the hydrolysis of 1,4-β-D-xylans, to remove successive D-xylose residues from the non-reducing termini. This enzyme may also be referred to as xylan 1,4-β-xylosidase, 1,4-β-D-xylan xylohydrolase, exo-1,4-β-xylosidase or xylobiase.

An α-L-arabinofuranosidase (EC 3.2.1.55) catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

An alpha-glucuronidase (EC 3.2.1.139) catalyzes the hydrolysis of an alpha-D-glucuronoside to D-glucuronate and an alcohol.

An acetylxylanesterase (EC 3.1.1.72) catalyzes the hydrolysis of acetyl groups from polymeric xylan, acetylated xylose, acetylated glucose, alpha-napthyl acetate, and p-nitrophenyl acetate.

A feruloyl esterase (EC 3.1.1.73) has 4-hydroxy-3-methoxycinnamoyl-sugar hydrolase activity (EC 3.1.1.73) that catalyzes the hydrolysis of the 4-hydroxy-3-methoxycinnamoyl(feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

A coumaroyl esterase (EC 3.1.1.73) catalyzes a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

An α-galactosidase (EC 3.2.1.22) catalyzes the hydrolysis of terminal, non-reducing α-D-galactose residues in α-D-galactosides, including galactose oligosaccharides, galactomannans, galactans and arabinogalactans. This enzyme may also be referred to as melibiase.

A β-galactosidase (EC 3.2.1.23) catalyzes the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

A β-mannanase (EC 3.2.1.78) catalyzes the random hydrolysis of 1,4-β-D-mannosidic linkages in mannans, galactomannans and glucomannans. This enzyme may also be referred to as mannan endo-1,4-β-mannosidase or endo-1,4-mannanase.

A β-mannosidase (EC 3.2.1.25) catalyzes the hydrolysis of terminal, non-reducing β-D-mannose residues in β-D-mannosides. This enzyme may also be referred to as mannanase or mannase.

One or more enzymes that degrade pectin may also be included in an enzyme mixture that comprises at least one endoglucanase variant of the invention. A pectinase catalyzes the hydrolysis of pectin into smaller units such as oligosaccharide or monomeric saccharides. An enzyme mixture may comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

An endo-polygalacturonase (EC 3.2.1.15) catalyzes the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide)glycanohydrolase.

A pectin methyl esterase (EC 3.1.1.11) catalyzes the reaction: pectin+n H$_2$O=n methanol+pectate. The enzyme may also been known as pectin esterase, pectin demethoxylase, pectin methoxylase, pectin methylesterase, pectase, pectinoesterase or pectin pectylhydrolase.

A endo-galactanase (EC 3.2.1.89) catalyzes the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

A pectin acetyl esterase catalyzes the deacetylation of the acetyl groups at the hydroxyl groups of GalUA residues of pectin.

An endo-pectin lyase (EC 4.2.2.10) catalyzes the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin transeliminase; endo-pectin lyase, polymethylgalacturonic transeliminase, pectin methyltranseliminase, pectolyase, PL, PNL or PMGL or (1→4)-β-O-methyl-α-D-galacturonan lyase.

A pectate lyase (EC 4.2.2.2) catalyzes the eliminative cleavage of (1→4)-α-D-galacturonan to produce oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

An alpha rhamnosidase (EC 3.2.1.40) catalyzes the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

An exo-galacturonase (EC 3.2.1.82) hydrolyzes pectic acid from the non-reducing end, releasing digalacturonate. The enzyme may also be known as exo-poly-α-galacturonosidase, exopolygalacturonosidase or exopolygalacturanosidase.

An exo-galacturonase (EC 3.2.1.67) catalyzes a reaction of the following type: (1,4-α-D-galacturonide)n+H2O=(1,4-α-D-galacturonide)n-i+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

An exopolygalacturonate lyase (EC 4.2.2.9) catalyzes eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-transeliminase, PATE, exo-PATE, exo-PGL or (1→4)-α-D-galacturonan reducing-end-disaccharide-lyase.

A rhamnogalacturonan hydrolyzes the linkage between galactosyluronic acid acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

A rhamnogalacturonan lyase cleaves α-L-Rhap-(1→4)-α-D-GalpA linkages in an endo-fashion in rhamnogalacturonan by beta-elimination.

A rhamnogalacturonan acetyl esterase catalyzes the deacetylation of the backbone of alternating rhamnose and galacturonic acid residues in rhamnogalacturonan.

A rhamnogalacturonan galacturonohydrolase hydrolyzes galacturonic acid from the non-reducing end of strictly alternating rhamnogalacturonan structures in an exo-fashion. This enzyme may also be known as xylogalacturonan hydrolase.

An endo-arabinanase (EC 3.2.1.99) catalyzes endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

One or more enzymes that participate in lignin degradation may also be included in an enzyme mixture that comprises at least one endoglucanase variant of the invention. Enzymatic lignin depolymerization can be accomplished by lignin peroxidases, manganese peroxidases, laccases and/or cellobiose dehydrogenases (CDH), often working in synergy. These extracellular enzymes are often referred to as lignin-modifying enzymes or LMEs. Three of these enzymes comprise two glycosylated heme-containing peroxidases: lignin peroxidase (LIP); Mn-dependent peroxidase (MNP); and, a copper-containing phenoloxidase laccase (LCC).

Laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

Mn-dependent peroxidase. The enzymatic activity of Mn-dependent peroxidase (MnP) in is dependent on Mn2+. Without being bound by theory, it has been suggested that the main role of this enzyme is to oxidize Mn2+ to Mn3+ (Glenn et al. (1986) Arch. Biochem. Biophys. 251:688-696). Subsequently, phenolic substrates are oxidized by the Mn3+ generated.

Lignin peroxidase (LiP). Lignin peroxidase is an extracellular heme that catalyzes the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by a theory, has been proposed to function as a physiological redox mediator in the LiP-catalysed oxidation of lignin in vivo (Harvey, et al. (1986) FEBS Lett. 195, 242-246).

An enzymatic mixture comprising at least one endoglucanase variant of the invention may further comprise at least one of the following; a protease or a lipase that participates in cellulose degradation.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. The term "lipids" includes, but is not limited to waxes derived from fatty acids, as well as cutin and suberin.

An enzyme mixture that comprises at least one endoglucanase variant of the invention may also comprise at least one expansin or expansin-like protein, such as a swollenin (see Salheimo et al., *Eur. J. Biohem.* 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A glucoamylase (EC 3.2.1.3) is an enzyme which catalyzes the release of D-glucose from non-reducing ends of oligo- and poly-saccharide molecules. Glucoamylase is also generally considered a type of amylase known as amyloglucosidase.

An amylase (EC 3.2.1.1) is a starch cleaving enzyme that degrades starch and related compounds by hydrolyzing the α-1,4 and/or α-1,6 glucosidic linkages in an endo- or an exo-acting fashion. Amylases include α-amylases (EC 3.2.1.1); β-amylases (3.2.1.2), amylo-amylases (EC 3.2.1.3), α-glucosidases (EC 3.2.1.20), pullulanases (EC 3.2.1.41), and isoamylases (EC 3.2.1.68). In some embodiments, the amylase is an α-amylase.

An enzyme mixture that comprises an endoglucanase variant of the invention may also comprise at least one of the following: a polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multi-functional integrating subunits which may organize cellulolytic subunits into a multi-enzyme complex. This is accomplished by the interaction of two complementary classes of domain, e.g. a cohesion domain on scaffoldin and a dockerin domain on each enzymatic unit. The scaffoldin subunit also bears a cellulose-binding module that mediates attachment of the cellulosome to its substrate. A scaffoldin or cellulose integrating protein for the purposes of this invention may comprise one or both of such domains.

An enzyme mixture that comprises at least one endoglucanase variant of the invention may also comprise at least one cellulose-induced protein or modulating protein, for example as encoded by cip1 or cip2 gene or similar genes from *Trichoderma reesei* (see Foreman et al., *J. Biol. Chem.* 278(34), 31988-31997, 2003).

An enzyme mixture that comprises at least one endoglucanase variant of the invention may comprise a member of each of the classes of the polypeptides described above, several members of one polypeptide class, or any combination of these polypeptide classes.

Endoglucanase Compositions

The endoglucanase variants of the present invention may be used in combination with other optional ingredients such as buffers, surfactants, and/or scouring agents. A buffer may be used with an endoglucanase of the present invention (optionally combined with other cellulases, including another endoglucanase) to maintain a desired pH within the solution in which the endoglucanase is employed. The exact concentration of buffer employed will depend on several factors which the skilled artisan can determine. Suitable buffers are well known in the art. A surfactant may further be used in combination with the endoglucanases of the present invention. Suitable surfactants include any surfactant compatible with the endoglucanase and, optionally, with any other cellulases being used. Exemplary surfactants include an anionic, a non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, etc. Suitable counter ions for anionic surfactants include, but are not limited to, alkali metal ions such as sodium and potassium; alkaline earth metal ions such as calcium and magnesium; ammonium ion; and alkanolamines having 1 to 3 alkanol groups of carbon number 2 or 3. Ampholytic surfactants include, e.g., quaternary ammonium salt sulfonates, and betaine-type ampholytic surfactants. Nonionic surfactants generally comprise polyoxyalkylene ethers, as well as higher fatty acid alkanolamides or alkylene oxide adduct thereof, and fatty acid glycerine monoesters. Mixtures of surfactants can also be employed as is known in the art.

The present invention may be practiced at any suitable effective amounts, concentrations, and lengths of time. An effective amount of endoglucanase is a concentration of endoglucanase sufficient for its intended purpose. For example, an effective amount of endoglucanase within a solution may vary depending on whether the intended purpose is to use the enzyme composition comprising the endoglucanase in a saccharification process, or for example a textile application such as stone-washing denim jeans. The amount of endoglucanase employed is further dependent on the equipment employed, the process parameters employed, and the cellulase activity, e.g., a particular solution will require a lower concentration of endoglucanase where a more active cellulase composition is used as compared to a less active cellulase composition. A concentration of endoglucanase and length of time that an endoglucanase will be in contact with the desired target further depends on the particular use employed by one of skill in the art, as is described herein.

One skilled in the art may practice the present invention using endoglucanases in either aqueous solutions, or a solid endoglucanase concentrate. When aqueous solutions are employed, the endoglucanase solution can easily be diluted to allow accurate concentrations. A concentrate can be in any form recognized in the art including, but not limited to, liquids, emulsions, gel, pastes, granules, powders, agglomerates, or solids. Other materials can also be used with or placed in the cellulase composition of the present invention as desired, including but not limited to stones, pumice, fillers, solvents, enzyme activators, and anti-redeposition agents, the choice of which depends upon the intended use of the composition.

V. Examples and Exemplary Variants and Substitution Sets of the Invention

The following examples are offered to illustrate, but not to limit the claimed invention.

Example 1

Wild-Type *M. thermophila* Endoglucanase Gene Acquisition and Construction of Expression Vectors

*M. thermophila* strain C1 endoglucanase cDNA genes (complementary DNA) were synthesized and the DNA sequence verified. For the Round 1 screen, wild-type *M. thermophila* C1 endoglucanase expression was codon optimized for expression in *Saccharomyces cerevisiae* strain InvSc1, a commercially available strain (Invitrogen, Carlsbad, Calif.). The codon-optimized cDNA construct is provided as SEQ ID NO:2 and the polypeptide encoded by the codon-optimized cDNA construct of SEQ ID NO:2 is provided as SEQ ID NO:3. For both SEQ ID NO:2 and SEQ ID NO:3, the signal peptide region is underlined. The signal peptide of SEQ ID NO:2 and SEQ ID NO:3 is the *T. reesei* cellobiohydrolase 2 (CBH2) signal peptide (Accession No. P07987). Analysis of the polypeptide sequence of SEQ ID NO:3 revealed that the endoglucanase polypeptide has a aspartic acid-to-glutamic acid (D/E) point mutation at residue 332 as compared to the wild-type polypeptide of SEQ ID NO:1 (residue numbering based on the mature protein sequence lacking a signal peptide).

For the Round 2 screen, wild-type *M. thermophila* C1 endoglucanase cDNA was cloned for expression in *Saccharomyces cerevisiae*. This cDNA construct is provided as SEQ ID NO:4 and the polypeptide encoded by the cDNA construct of SEQ ID NO:4 is provided as SEQ ID NO:5. The first 16 amino acids of SEQ ID NO:5 comprise the signal peptide region, and are encoded by the first 48 nucleotides of SEQ ID NO:4. The signal peptide of SEQ ID NO:4 and SEQ ID NO:5 is the native signal peptide of *M. thermophila* C1 endoglucanase. The portion of SEQ ID NO:5 following the signal peptide is identical to the wild-type *M. thermophila* C1 endoglucanase of SEQ ID NO:1.

Example 2

Shake Flask Procedure

A single colony of *S. cerevisiae* containing a plasmid with the *M. thermophila* C1 endoglucanase cDNA gene is inoculated into 1 mL Synthetic Defined-uracil (SD-ura) Broth (2 g/L synthetic Drop-out minus uracil w/o yeast nitrogen base (from United States Biological, Swampscott, Mass.), 5 g/L Ammonium Sulphate, 0.1 g/L Calcium Chloride, 2 mg/L Inositol, 0.5 g/L Magnesium Sulphate, 1 g/L Potassium Phosphate monobasic ($KH_2PO_4$), 0.1 g/L Sodium Chloride) containing 6% glucose, pH 6.0. Cells are grown overnight (at least 12 hours) in an incubator at 37° C. with shaking at 250 rpm. The culture is then diluted into 50 mL broth SD-ura media containing 2% glucose in a 250 mL baffled sterile shake flask and incubated at 37° C. for 48 hours. Cells are pelleted by centrifugation (4000 rpm, 15 min, 4° C.). The clear media supernatant containing the secreted *M. thermophila* C1 endoglucanase is collected and stored at −20° C. until use.

Example 3

Assays to Determine Endoglucanase Activity

Endoglucanase activity may be determined either by a cellulose assay, or a dyed cellulose-based assay.

Endoglucanase activity was determined using a cellulose assay, which used microcrystalline cellulose (AVICEL® cellulose, available from Sigma) as a substrate. In a total volume of 150 μL, 75 μL clear media supernatant containing endoglucanase enzyme was added to 200 g/L AVICEL® cellulose in 300 mM sodium acetate buffer (pH 4-5). The reaction was incubated at 50-70° C. for 18-24 hours. Biotransformations were diluted with 150 μL of water. Beta-glucosidase, which converts cellobiose to glucose, was subsequently added and conversion of AVICEL® cellulose to soluble sugar oligomers was measured using a GOPOD Assay. Soluble sugar oligomer production was measured by mixing 10 μl of the above reaction with 190 μl of GOPOD assay mix. The reactions were allowed to shake for 30 min at room temp. Absorbance of the solution was measured at 510 nm to determine the amount of glucose produced in the original AVICEL® cellulose biotransformation reaction.

Endoglucanase activity was also determined using a dyed cellulose-based assay, which used AZCL-HE-cellulose (Megazyme, Wicklow, Ireland) as a substrate. In a total volume of 220 μL, 40 μL of diluted clear media supernatant containing endoglucanase enzyme was added to 180 μl of slurry containing 2 g/L AZCL-HE-Cellulose in 300 mM sodium acetate buffer (pH 4-5). The reaction was incubated at 50-70° C. for an appropriate time (up to 24 hours, depending on the enzyme concentration). Reactions were then filtered to remove insoluble oligomers. The absorbance of the clarified solution was measured at 490 nm. Degradation of AZCL-HE-Cellulose and extent of soluble dye release was used as a measure of AZCL-HE-Cellulose degrading activity of endoglucanase.

Example 4

Evaluation of Optimal *M. thermophila* C1 Endoglucanase Activity and Stability

The wild-type C1 endoglucanase activity profile was investigated at different temperatures (50° C., 60° C., 65° C., 70° C., and 80° C.) and pH (3.5, 4, 4.5, 5, 6, and 7) using Biomass (52 g/L glucan) as a substrate. The experimental and analytical procedures are described in Example 3. Wild-type *M. thermophila* C1 endoglucanase exhibited optimum activity at pH 6.0 and 60° C., and detectable endoglucanase activity was observed under high-throughput screening conditions (pH 4.5, 65° C.).

Example 5

High Throughput Assays to Identify Improved *M. thermophila* C1 Endoglucanase Variants Variations (silent nucleotide changes and/or substitutions at amino acid residues) were introduced into endoglucanase cDNA sequences resulting in the generation of plasmid libraries. The plasmid libraries containing variant endoglucanase genes were transformed into *S. cerevisiae* and plated on SD-ura agar plate containing 2% glucose. After incubation for at least 48 hours at 30° C., colonies were picked using a Q-Bot® robotic colony picker (Genetix USA, Inc., Beaverton, Oreg.) into shallow, 96-well well microtiter plates containing pH adjusted 200 μL SD-ura media and 6% glucose. Cells were grown for 24 hours at 30° C. with shaking at 250 rpm and 85% humidity. 20 μL of this overnight culture was then transferred into 96-well microtiter plates (deep well) containing 380 μL SD-ura medium and 2% glucose as described in Example 2. The plates were incubated at 37° C. with shaking at 250 rpm and 85% humidity for 48 hours. The deep plates were centrifuged at 4000 rpm for 15 minutes and the clear media supernatant containing the secreted endoglucanase was used for the high throughput AVICEL® cellulose assay.

The *M. thermophila* C1 endoglucanase libraries were screened in high throughput using both thermoactivity and thermostability assays. In the thermoactivity assay, *M. thermophila* C1 endoglucanase variants were screened with a cellulose-based high throughput assay (Substrate: AVICEL® cellulose; pH: 4.2-4.5; temperature: 65-70° C.; time:

18-21 hours). Active *M. thermophila* C1 endoglucanase variants identified from the thermoactivity assay were subsequently subjected to the thermostability assay. In the thermostability assay, the HTP media supernatant samples containing *M. thermophila* C1 endoglucanase variant enzymes were pre-incubated at pH 3.5-4.5, 70-75° C. for 1 or 16 hours. The residual enzyme activity after the thermal challenge was measured using a cellulose-based assay (substrate: AVICEL® cellulose; pH 5.0; temperature 50° C.; time: 24 hrs) or a dyed cellulose-based assay (substrate: azurine-crosslinked AZCL-HE-Cellulose; pH: 5.0; temperature: 55° C.; time: 40 minutes) as described in Example 3.

Thermoactivity Assay

Thermoactivity was screened using a cellulose-based High Throughput Assay. In deep, 96-well microtiter plates 75 µL of media supernatant containing *M. thermophila* C1 endoglucanase variant enzymes was added to 75 µL of 200 g/L microcrystalline cellulose (AVICEL® cellulose, from Sigma) in 300 mM sodium acetate buffer pH 4.2-5.0. After sealing with aluminum/polypropylene laminate heat seal tape (Velocity 11 (Menlo Park, Calif.), Cat#06643-001), the plates were shaken at 60-70° C. for up to 21 hrs. After 21 hrs, the reactions were diluted by adding 150 µL of water into the deep well plates. The plates were centrifuged at 4000 rpm for 5 minutes. 150 µL of supernatant from reaction mixture was filtered with 0.45 µm low-binding hydrophilic PTFE filter plate (Millipore, Billerica, Mass.). The HPLC sample plates were sealed with heat seal tape to prevent evaporation. Beta-glucosidase, which converts cellobiose to glucose, was subsequently added and conversion of AVICEL® cellulose to soluble sugar oligomers was measured by GOPOD Assay. Soluble sugar production was measured using GOPOD Assay mix as described in Example 3.

Thermostability Assay

Thermostability was screened using dyed cellulose-based High Throughput Assay (used in Rounds 1 and 2) or AVICEL® Cellulose High Throughput Assay (used in Rounds 3 and 4).

For determining residual activity by dyed cellulose-based assay, *M. thermophila* C1 endoglucanase variant samples were pre-incubated at high temperature (Round 1 screening: pH 4.5, 70° C. for 1 or 2 hours; Round 2 screening: pH 4.5, 70° C. for 1 hour). Following pre-incubation of the *M. thermophila* C1 endoglucanase variant enzyme samples, the residual activity of the enzyme was determined by dyed cellulose-based assay using the substrate Azcl-HE-Cellulose (Megazyme, Wicklow, Ireland); pH 5; 55° C.; 40 minutes). In a total volume of 220 µL, 40 µL of preincubated enzyme samples were added to 180 µl slurry containing 2 g/L AZCL-HE-Cellulose in 300 mM sodium acetate buffer (pH 5). The reaction was incubated at 50° C. for 40 min. After the required time period, reactions were filtered to remove insoluble oligomers. The absorbance of the clarified solution was measured at 490 nm. Degradation of AZCL-HE-Cellulose and extent of soluble dye release was used as a measure of EG activity.

For determining residual activity using a microcrystalline cellulose (AVICEL®) assay, *M. thermophila* C1 endoglucanase variant samples were pre-incubated at high temperature (Round 3 screening: pH 4, 75° C. for 2.5 hours; Round 4 screening: pH 3.5, 75° C. for 3 hours or pH 4, 75° C. for 16 hours). Following pre-incubation of the *M. thermophila* C1 endoglucanase variant enzyme samples, the residual activity of the enzyme was determined by AVICEL® cellulose assay (substrate: 200 g/L AVICEL® cellulose; pH 5; 50° C.; 24 hours) as described above for the Thermoactivity Assay.

The residual activity was calculated using the formula:

% residual activity=100×(Activity of challenged samples/Activity of unchallenged samples)

Residual activities of the *M. thermophila* C1 endoglucanase variants were compared to that of the wild-type *M. thermophila* C1 endoglucanase to identify the thermostability improved variants.

Example 6

Improved Endoglucanase Activities and Stabilities of Engineered *M. thermophila* C1 Endoglucanase Variants Improved *M. thermophila* C1 endoglucanase variants were identified from the high throughput screening of various *M. thermophila* C1 endoglucanase variant libraries as described in Example 5. For the Round 1 screen (Table 2), the *M. thermophila* C1 endoglucanase of SEQ ID NO:3 (which differs from wild-type in that SEQ ID NO:3 has a D332E point mutation) was the reference protein. For the Round 2 screen, the *M. thermophila* C1 endoglucanase of SEQ ID NO:5 was the reference protein. *M. thermophila* C1 endoglucanase variants were generated and evaluated as indicated in the legends to Tables 2 and 3 to identify variants that had improved thermoactivity and thermostability relative to the reference sequence. From the Round 2 screen, one of the improved variants from the round (Variant 213, as shown in Tables 3 and 4) was then selected as a reference protein for the Round 3 screen, and additional *M. thermophila* C1 endoglucanase variants were generated and evaluated as described in the legend to Table 4 to identify variants that had improved stability and activity relative to Variant 213. One variant (Variant 309, as shown in Tables 4 and 5) was selected from this round as a reference protein for the Round 4 screen, and additional *M. thermophila* C1 endoglucanase variants were generated and evaluated as described in the legend to table 5 to identify variants that had improved stability and activity relative to Variant 309. Two variants (Variant 372 and Variant 443) from Round 4 were then selected for further characterization of thermoactivity and thermostability properties, as described in Example 10 below.

Tables 2-5 summarize the improvement in thermoactivities and thermostabilities of certain *M. thermophila* C1 endoglucanase variants encompassed by the present invention.

Table 2 summarizes the results of the Round 1 screen, which identified improved *M. thermophila* C1 endoglucanase variants derived from a wild-type *M. thermophila* C1 endoglucanase codon-optimized construct (SEQ ID NO:2). The thermoactivity and thermostability of the endoglucanase variants were compared to the thermoactivity and thermostability of the *M. thermophila* C1 endoglucanase of SEQ ID NO:3. The thermoactivity conditions for the Round 1 screening were pH 4.5 and 65° C. for 21 hours on AVICEL® cellulose. Thermostability was assessed by determining residual enzyme activity after incubation at pH 4.5 and 70° C. for 1 or 2 hours (substrate: Azcl-HE-Cellulose). Thermoactivity and thermostability are presented as fold increase over wild-type *M. thermophila* C1 endoglucanase (SEQ ID NO:3). Silent nucleotide changes are indicated with respect to the codon-optimized wild-type *M. thermophila* C1 endoglucanase cDNA sequence (SEQ ID NO:2). Amino acid positions (e.g., "H95") and changes (e.g., "H95D") are relative to the mature (e.g., post-signal peptide) portion of the sequence of SEQ ID NO:3; the mature portion of the SEQ ID NO:3 sequence differs from the wild-type *M. thermophila* C1 endoglucanase sequence of SEQ ID NO:1 in that SEQ ID NO:3 has a D332E point mutation.

TABLE 2

Improved *M. thermophila* C1 endoglucanase variants identified in Round 1 screening

| Variant | Amino acid changes over SEQ ID NO: 3 | SNC | Activity: Fold increase over SEQ ID NO: 3 | Stability: Fold increase over SEQ ID NO: 3 (1 hr) | Stability: Fold increase over SEQ ID NO: 3 (2 hr) |
|---|---|---|---|---|---|
| SEQ ID NO: 3 | — |  | — | — | — |
| 2 | H95D + S131A + V169I + N202H + E332D + G360A |  | +++ |  | ++++ |
| 3 | H95D + S131G + N202H + S242T + E332D |  | +++ |  | ++++ |
| 4 | H95D + S131G + Q287E + E332D + G360A |  | +++ |  | ++++ |
| 5 | H95D + S131G + N202H + S242T + H276S |  | +++ |  | ++++ |
| 6 | H95D + Q287E + G360A |  | +++ |  | ++++ |
| 7 | H95D + Q287E + L323M + G360A |  | +++ |  | ++++ |
| 8 | E332D + G360A |  | +++ |  | ++++ |
| 9 | H95D + N202H |  | +++ |  | ++++ |
| 10 | H95D + N202H + Q287E + L323M + G360A |  | +++ |  | ++++ |
| 11 | H95D + Q287E |  | +++ |  | ++++ |
| 12 | H95D + S242T + Q287E + G360A |  | +++ |  | ++++ |
| 13 | H95D + Q287E |  | ++ |  | ++++ |
| 14 | H95D |  | ++ |  | ++++ |
| 15 | H95D + G360A |  | ++ |  | ++++ |
| 16 | D118P |  | ++ | +++ |  |
| 17 | H95D |  | ++ |  | ++++ |
| 18 | H95D + N202H |  | ++ |  | ++++ |
| 19 | Q287E + G360A |  | ++ |  | ++++ |
| 20 | D118P + F133P + T173P + A312P + S366P |  | ++ | +++ |  |
| 21 | A151Q |  | ++ |  | + |
| 22 | H95D + S131G + H276S |  | ++ |  | ++++ |
| 23 | H95D + S131G + L323M |  | ++ |  | ++++ |
| 24 | N146E |  | ++ |  | − |
| 25 | N202H + Q287E + E332D |  | ++ |  | ++++ |
| 26 | H95D + S131G + V169I + L323M |  | ++ |  | +++ |
| 27 | H95D + N202H + H276S |  | + |  | ++++ |
| 28 | N146Q |  | + |  | − |
| 29 | N146R |  | + |  | − |
| 30 | D118P |  | + | +++ |  |
| 31 | V169I + N202H + S242T + Q287E + L323M + E332D |  | + |  | ++++ |
| 32 | D118P + T173P | g534a | + | +++ |  |
| 33 | S76V |  | + | +++ |  |
| 34 | T101P + D118P | a447g | + | ++++ |  |
| 35 | E143T |  | + |  | − |
| 36 | V169I + N202H + S242T + H276S |  | + |  | ++++ |
| 37 | D118G |  | + | +++ |  |
| 38 | N150D |  | + |  | + |
| 39 | E143T |  | + |  | − |
| 40 | E332D |  | + |  | ++ |
| 41 | F147Y |  | + |  | + |
| 42 | D118G |  | + | +++ |  |
| 43 | A151R |  | + |  | − |
| 44 | D118A |  | + | +++ |  |
| 45 | D118P |  | + | +++ |  |
| 46 | A151R |  | + |  | − |
| 47 | T203N |  | + | +++ |  |
| 48 | Y351F |  | + | ++ |  |
| 49 | N150D |  | + |  | + |
| 50 | D118P |  | + | +++ |  |
| 51 | S131G + V169I + N202H + H276S |  | + |  | − |
| 52 | S76V |  | + | ++ |  |
| 53 | N146R |  | + |  | + |
| 54 | S76V + K94E |  | + | ++ |  |
| 55 | D118C |  | + | +++ |  |
| 56 | Y351F |  | + | ++ |  |
| 57 | S76V + K94E |  | + | ++ |  |
| 58 | E135Q |  | + | +++ |  |
| 59 | G86P + D118P + A277P |  | + | +++ |  |
| 60 | D118G |  | + | +++ |  |
| 61 | D118T |  | + | +++ |  |
| 62 | Q257M |  | + | + |  |
| 63 | D118A |  | + | +++ |  |
| 64 | T203R |  | + | +++ |  |
| 65 | D118Y |  | + | +++ |  |
| 66 | T203R |  | + | +++ |  |
| 67 | D118C |  | + | +++ |  |
| 68 | K72H |  | + | + |  |
| 69 | A286E |  | + | + |  |
| 70 | N146R |  | + |  | − |

TABLE 2-continued

Improved *M. thermophila* C1 endoglucanase variants identified in Round 1 screening

| Variant | Amino acid changes over SEQ ID NO: 3 | SNC | Activity: Fold increase over SEQ ID NO: 3 | Stability: Fold increase over SEQ ID NO: 3 (1 hr) | Stability: Fold increase over SEQ ID NO: 3 (2 hr) |
|---|---|---|---|---|---|
| 71 | D118G | | + | +++ | |
| 72 | D118A | | + | +++ | |
| 73 | Q287E + G360A | | + | | +++ |
| 74 | N202H | | + | + | |
| 75 | N202H | | + | ++ | |
| 76 | S76M | | + | + | |
| 77 | S242T + H276S | | + | | − |
| 78 | Y351F | | + | ++ | |
| 79 | N363H | | + | ++ | |
| 80 | D118S | | + | +++ | |
| 81 | A286Q | | + | + | |
| 82 | N202H | | + | + | |
| 83 | N87C | | + | ++ | |
| 84 | S76M | | + | + | |
| 85 | L302K | c738t | + | + | |
| 86 | K72H | | + | + | |
| 87 | K70R | | + | − | |
| 88 | K70R | | + | + | |
| 89 | S131C | | + | − | |
| 90 | N150R | | + | | − |
| 91 | A151Y | | + | | − |
| 92 | E143H | | + | | + |
| 93 | S282A | | + | − | |
| 94 | V290E | | + | − | |
| 95 | A312P | | + | + | |
| 96 | S242T | | + | + | |
| 97 | Q287E | | + | | ++ |
| 98 | A286K | | + | + | |
| 99 | E85A | | + | − | |
| 100 | S242C | | + | + | |
| 101 | N174L | | + | − | |
| 102 | A312P | | + | + | |
| 103 | E85A | | + | + | |
| 104 | N127H | | + | − | |
| 105 | T245Q | | + | − | |
| 106 | N202H | | + | ++ | |
| 107 | D118G | | + | +++ | |
| 108 | G300H | | + | − | |
| 109 | L302K | | + | − | |
| 110 | T203H | | + | + | |
| 111 | V290W | | + | + | |
| 112 | K153Q | | + | | − |
| 113 | T203R | | + | ++ | |
| 114 | Q128T | | + | + | |
| 115 | K94I | | + | + | |
| 116 | S366A | | + | − | |
| 117 | A277P | | + | − | |
| 118 | L91M | | + | ++ | |
| 119 | T203H | | + | ++ | |
| 120 | T203K | | + | + | |
| 121 | N202H | | + | + | |
| 122 | V290R | | + | + | |
| 123 | M250L | | + | + | |
| 124 | I367L | | + | − | |
| 125 | S76A | | + | ++ | |
| 126 | D205P | | + | + | |
| 127 | D118S | | + | +++ | |
| 128 | S131C | | + | + | |
| 129 | Q257E | | + | + | |
| 130 | N363H | | + | + | |
| 131 | T203S | | + | + | |
| 132 | A286E | | + | + | |
| 133 | T203R | | + | +++ | |
| 134 | S366C | | + | − | |
| 135 | T248N | | + | + | |
| 136 | N174S | | + | + | |
| 137 | N202H | | + | + | |
| 138 | R177M | | + | + | |
| 139 | S357C | | + | − | |
| 140 | T321Q | | + | + | |
| 141 | Y351F | | + | + | |
| 142 | Q186E | | + | + | |
| 143 | S270E | | + | + | |

TABLE 2-continued

Improved *M. thermophila* C1 endoglucanase variants identified in Round 1 screening

| Variant | Amino acid changes over SEQ ID NO: 3 | SNC | Activity: Fold increase over SEQ ID NO: 3 | Stability: Fold increase over SEQ ID NO: 3 (1 hr) | Stability: Fold increase over SEQ ID NO: 3 (2 hr) |
|---|---|---|---|---|---|
| 144 | T359K | | + | − | |
| 145 | A314T | | + | − | |
| 146 | E135P | | + | − | |
| 147 | T248Q | | + | + | |
| 148 | S366N | | + | − | |
| 149 | A298E | | + | + | |
| 150 | T254V | | + | + | |
| 151 | G86P + D118P + T173P | | + | +++ | |
| 152 | T203H | | + | + | |
| 153 | L71F + M250L + H326Y | | + | − | |
| 154 | S191P | | + | − | |
| 155 | V290W | | + | + | |
| 156 | A286V | | + | + | |
| 157 | A277P | | + | + | |
| 158 | S191P | | + | + | |
| 159 | A298D | | + | + | |
| 160 | E135P | | + | + | |
| 161 | L71F + F96Y + M250L | | + | − | |
| 162 | T207D | | + | ++ | |
| 163 | N211A | | + | + | |
| 164 | A236G | | + | + | |
| 165 | M250L | | + | + | |
| 166 | S282A | | + | + | |
| 167 | T203R | | + | + | |
| 168 | V290S | | + | + | |
| 169 | V290S | | + | + | |
| 170 | S270E | | + | + | |
| 171 | V289L | | + | + | |
| 172 | V290Y | | + | + | |
| 173 | T248Q | | + | + | |
| 174 | T248Q | | + | + | |
| 175 | H276S + E332D | | + | | + |
| 176 | A277P | | + | + | |
| 177 | L71F + F96Y + M250L | | + | − | |
| 178 | Q257S | | + | + | |
| 179 | S282E | | + | + | |
| 180 | V290W | | + | + | |
| 181 | H276S + G360A | | + | | +++ |
| 182 | Q287E | | + | + | |
| 183 | T101P + E135P + A312P | | − | ++ | |
| 184 | T101P + A312P | | − | − | |
| 185 | G86P + D118P + T173P | | − | +++ | |
| 186 | T245V | | − | + | |
| 187 | T203D + M250L | c960t | − | + | |
| 188 | T203D + M250L | | − | + | |
| 189 | V169I | | − | | + |
| 190 | L71F + I117V + T203D + M250L + N283T | | − | − | |
| 191 | V169I | | − | | +++ |
| 192 | Y112M + N202H + H276S + Q287E + G360A | | − | | + |
| 193 | Y112M + S131G + S242T + L323M + G360A | | − | | +++ |
| 194 | H276S + D325N | | − | | ++++ |
| 195 | Y112M + Q287E + E332D | | − | | ++++ |
| 196 | Y112M | | − | | ++++ |
| 197 | L210P + V304F + H326Y | | − | ++ | |

Fold increase for activity and stability is represented as follows:
− = less than 1.0 fold increase over C1 endoglucanase SEQ ID NO: 3
+ = 1.0 to 1.9 fold increase over C1 endoglucanase SEQ ID NO: 3
++ = 2.0 to 2.9 fold increase over C1 endoglucanase SEQ ID NO: 3
+++ = 3.0 to 10.0 fold increase over C1 endoglucanase SEQ ID NO: 3
++++ = greater than 10.0 fold increase over C1 endoglucanase SEQ ID NO: 3
SNC = Silent nucleotide changes Example 7

Improved Endoglucanase Activities and Stabilities of Engineered *M. thermophila* C1 Endoglucanase Variants—Round 2 Screen Table 3 summarizes the results of the Round 2 screen, which identified improved *M. thermophila* C1 endoglucanase variants derived from a wild-type *M. thermophila* C1 endoglucanase cDNA construct of SEQ ID NO:4. The thermoactivity and thermostability of the Round 2 endoglucanase variants were compared to the thermoactivity and thermostability of wild-type *M. thermophila* C1 endoglucanase (SEQ ID NO:5). The thermoactivity conditions for the Round 2 screening were pH 4.5 and 65° C. for 21 hours on AVICEL® cellulose. Thermostability was assessed by determining residual enzyme activity after incubation at pH 4.5 and 70° C. for 1 hour (substrate: Azcl-HE-Cellulose). Thermoactivity and thermostability are presented as fold increase over the wild-type *M. thermophila* C1 endoglucanase of SEQ ID NO:5. Silent nucleotide changes are indicated with respect to the wild-type C1 endoglucanase cDNA sequence (SEQ ID NO:4). Amino acid positions (e.g., "D118") and changes (e.g., "D118P") are relative to mature wild-type *M. thermophila* C1 endoglucanase protein sequence lacking a signal peptide (SEQ ID NO:1).

TABLE 3

Improved *M. thermophila* C1 endoglucanase variants identified in Round 2 screening

| Variant Number | Amino acid changes over WT (SEQ ID NO: 1) | SNC | Activity: Fold increase over SEQ ID NO: 5 | Stability: Fold increase over SEQ ID NO: 5 |
|---|---|---|---|---|
| Rd 2 WT backbone | — | — | — | — |
| 199 | D118P + A151Q + N202H + S366P | g423t | + | ++++ |
| 200 | D118P + N202H + A312P | | + | ++++ |
| 201 | H95D + S191P + N202H + A312P | | + | ++++ |
| 202 | D118P + A151Q + S191P + S366P | g768t | + | ++++ |
| 203 | D118P + M250L | | + | +++ |
| 204 | L71F + D118P + E135Q + A151Q + S191P + N202H + S242T + M250L + G360A | | + | ++++ |
| 205 | L71F + D118P + N202H + S242T + M250L + G360A | | + | +++ |
| 206 | L71F + D118P + E135Q + A151Q + N202H | | + | ++++ |
| 207 | D118P + E135P + A312P | g684a | + | +++ |
| 208 | G12E + D118P + E135P + S366P | | + | ++++ |
| 209 | H95D + D118P + A151Q + S242T + A312P + G360A + S366P | g318a | + | ++++ |
| 210 | L71F + S191P + N202H + S242T + M250L + A312P + G360A + S366P | | + | +++ |
| 211 | H95D + D118P + E135Q + N146D + A151Q + N202H | | + | ++++ |
| 212 | D118P + A151Q + S242T + M250L | g318a | + | +++ |
| 213 | L71F + D118P + N202H + S242T + M250L | | + | ++++ |
| 214 | L71F + D118P + N202H + S242T + G360A + S366P | | + | +++ |
| 215 | D118P + E135P + M250L + G360A + S366P | | + | ++++ |
| 216 | L71F + D118P + A151Q + N202H | | + | ++++ |
| 217 | H95D + D118P + E135P + G360A + S366P | | + | ++++ |
| 218 | D118P + A151Q + S191P + S366P | | + | +++ |
| 219 | D118P + S191P + S242T | | + | ++ |
| 220 | D118P + A151Q + S242T + M250L + G360A | | + | +++ |
| 221 | D118P + M250L + S366P | | + | ++++ |
| 222 | H95D + E135Q + N202H + M250L | | + | ++++ |
| 223 | D118P + S191P + S242T + M250L + I367M | | + | +++ |
| 224 | S191P + N202H + M250L + T254M + G360A | | + | ++++ |
| 225 | E135P + A151Q + S242T + M250L + A312P + S366P | | + | +++ |
| 226 | H95D + S242T + M250L + E332D | | + | +++ |
| 227 | A151Q + N202H + G360A | | + | ++ |
| 228 | A151Q + S191P + N202H + S242T + G360A + S366P | | + | +++ |
| 229 | E135P + A151Q + S191P + A312P + S366P | | + | ++ |
| 230 | H95D + A151Q + N202H + S242T + G358S + S366P | | + | + |

Fold increase for activity and stability is represented as follows:
+ = 1.0 to 1.9 fold increase over WT C1 endoglucanase SEQ ID NO: 5
++ = 2.0 to 2.9 fold increase over WT C1 endoglucanase SEQ ID NO: 5
+++ = 3.0 to 3.9 fold increase over WT C1 endoglucanase SEQ ID NO: 5
++++ = greater than 3.9 fold increase over WT C1 endoglucanase SEQ ID NO: 5
SNC = Silent nucleotide changes Example 8

Improved Endoglucanase Activities and Stabilities of Engineered *M. thermophila* C1 Endoglucanase Variants—Round 3 Screen Table 4 summarizes the results of the Round 3 screen, which identified improved *M. thermophila* C1 endoglucanase variants derived from Variant 213 (cDNA: SEQ ID NO:6; polypeptide sequence with signal peptide: SEQ ID NO:7; mature polypeptide lacking signal peptide: SEQ ID NO:8). The thermoactivity and thermostability of the endoglucanase variants were compared to the thermoactivity and thermostability of Variant 213. The thermoactivity conditions for the Round 3 screening were pH 4.5 and 70° C. for 21 hours on AVICEL® cellulose. Thermostability was assessed by determining residual enzyme activity on AVICEL® cellulose after incubation at pH 4.0 and 75° C. for 2.5 hours. Thermoactivity and thermostability are presented as fold increase over Variant 213. Silent nucleotide changes are indicated with respect to the wild-type *M. thermophila* C1 endoglucanase cDNA sequence (SEQ ID NO:4). Amino acid positions (e.g., "D118") and changes (e.g., "D118P") are relative to mature wild-type *M. thermophila* C1 endoglucanase protein sequence lacking a signal peptide (SEQ ID NO:1).

TABLE 4

Improved *M. thermophila* C1 endoglucanase variants identified in Round 3 screening

| Variant Number | Amino acid changes over WT (SEQ ID NO: 1) | SNC | Activity: Fold increase over Variant 213 | Stability: Fold increase over Variant 213 |
|---|---|---|---|---|
| 213 | L71F + D118P + N202H + S42T + M250L | | — | — |
| 231 | L71F + D118P + N202H + S242T + T248Q + M250L + Q287E | | ++++ | ++ |
| 232 | K72H + H95D + D118P + S131C + S242T + M250L + Q287E + G360A + S366P | | ++++ | ++++ |
| 233 | L71F + S76A + N87C + H95D + D118P + N202H + S242T + M250L + Q257E + S282A + A298E | | +++ | ++++ |
| 234 | L71F + H95D + D118P + N174S + N202H + A236G + S242T + M250L + Q257S | | +++ | +++ |
| 235 | L71F + H95D + D118A + N174S + N202H + S242T + M250L + Q257S + A298D | | +++ | ++++ |
| 236 | L71F + H95D + D118G + N202H + T203D + A236G + S242T + M250L + A298D | | +++ | +++ |
| 237 | L71F + H95D + D118G + N202H + T203D + S242T + M250L | | +++ | ++++ |
| 238 | L71F + E85A + H95D + D118P + N202H + N211A + S242T + M250L + A277P + A286K + Q287E + S366P | | +++ | ++++ |
| 239 | L71F + H95D + D118P + N202H + S242T + M250L + A277P | | +++ | ++++ |
| 240 | L71F + K72H + H95D + D118P + N202H + N211A + S242T + M250L + A286V + Q287E | | +++ | ++++ |
| 241 | L71F + H95D + D118T + N174S + N202H + S242T + M250L + S282A | g153a | +++ | ++++ |
| 242 | L71F + N87C + D118P + N202H + T203D + S242T + M250L + A298E | | ++ | ++ |
| 243 | K72H + H95D + D118P + S131C + N211A + S242T + T248N + M250L | | ++ | ++++ |
| 244 | L71F + H95D + D118T + N202H + S242T + T248Q + M250L + A286E | | ++ | ++++ |
| 245 | L71F + N87C + H95D + D118P + N174S + N202H + A236G + S242T + M250L + Q257S + S282G | | ++ | ++++ |
| 246 | L71F + H95D + D118P + N174S + N202H + S242T + M250L + S282A | | ++ | ++++ |
| 247 | L71F + H95D + D118P + N174S + N202H + S242T + M250L + Q257E + A298E | | ++ | ++++ |
| 248 | L71F + D118P + S131C + N202H + S242T + M250L + A286V | | ++ | + |
| 249 | L71F + S76M + H95D + D118P + N202H + S242T + M250L | | ++ | ++++ |
| 250 | L71F + E85A + H95D + D118P + N202H + S242T + M250L + A277P + A286E | | ++ | ++++ |
| 251 | L71F + E85A + H95D + D118P + S131C + N202H + S242T + T248Q + M250L + A277P + Q287E | c933t | ++ | ++++ |
| 252 | L71F + E85A + H95D + D118P + N202H + S242T + T248Q + M250L + Q287E | | ++ | ++++ |
| 253 | E85A + H95D + D118P + S131C + N202H + S242T + M250L + Q287E | | ++ | ++++ |
| 254 | L71F + H95D + D118P + N202H + N211A + S242T + T248N + M250L + A286L | | ++ | ++++ |
| 255 | L71F + S76M + H95D + D118P + N174S + N202H + A236G + S242T + M250L + Q257S + S282A | | ++ | ++++ |
| 256 | L71F + S76M + D118P + N202H + T203D + S242T + M250L + A298E | | ++ | ++++ |
| 257 | L71F + S76M + H95D + D118T + N174S + N202H + T203K + S242T + M250L | | ++ | ++++ |
| 258 | L71F + H95D + D118P + N202H + A236G + S282A | | ++ | +++ |
| 259 | H95D + D118P + S131C + S242T + T248N + M250L + A277P + Q287E | | + | ++++ |
| 260 | L71F + S76M + N87C + D118A + E135P + N202H + A236G + S242T + M250L + A298E | | + | ++++ |
| 261 | K72H + D118P + N202H + S242T + M250L + A286E | | + | + |

TABLE 4-continued

Improved *M. thermophila* C1 endoglucanase variants identified in Round 3 screening

| Variant Number | Amino acid changes over WT (SEQ ID NO: 1) | SNC | Activity: Fold increase over Variant 213 | Stability: Fold increase over Variant 213 |
|---|---|---|---|---|
| 262 | L71F + N87C + D118T + N202H + S242T + M250L + A298E + G360A + S366P | | + | ++++ |
| 263 | L71F + S76A + D118A + N174S + N202H + T203D + A236G + S242T + M250L + S282A + A298D | | + | ++++ |
| 264 | L71F + N87C + D118A + N174S + N202H + T203D + S242T + M250L + A298D | | + | ++++ |
| 265 | K70R + L71F + K94I + D118P + R177M + N202H + S242T + M250L + S282G + V290E + G360A + S366P | | + | ++++ |
| 266 | L71F + K72H + E85A + H95D + D118G + N202H + S242T + T248N + M250L | c522t | + | ++++ |
| 267 | L71F + N87C + D118P + N202H + A236G + S242T + M250L + G360A + S366P | | + | ++++ |
| 268 | L71F + S76M + N87C + D118A + N174S + N202H + T203D + S242T + M250L + A298D | | + | ++++ |
| 269 | L71F + S76M + N87C + D118P + N202H + S242T + M250L + S282A + A298E | | + | ++++ |
| 270 | L71F + D118P + N202H + A236G + S242T + M250L + Q257E + S282A + A298E + G360A + S366P | | + | +++ |
| 271 | E85A + D118P + N202H + S242T + T248N + M250L + A286K + Q287E | | + | +++ |
| 272 | L71F + N87C + D118P + N174S + N202H + T203D + A236G + S242T + M250L + A298D | | + | +++ |
| 273 | L71F + N87C + D118P + N202H + T203D + S242T + M250L + Q257S + S282A | | + | ++++ |
| 274 | L71F + S76M + N87C + D118P + N174S + N202H + T203S + A236G + S242T + M250L + Q257E + S282A + A298E | | + | ++++ |
| 275 | L71F + H95D + D118A + N202H + T203K + S242T + M250L | g204a | + | ++++ |
| 276 | K72H + E85A + D118P + N202H + S242T + T248Q + M250L + A286V + Q287E | | + | ++ |
| 277 | L71F + D118P + N202H + A236G + M250L + G360A + S366P | | + | +++ |
| 278 | L71F + S76M + N87C + D118P + N202H + T203S + S242T + M250L + S282A + A298E + G360A | | + | ++++ |
| 279 | L71F + S76M + D118P + N174S + N202H + T203S + S242T + M250L + Q257S + G360A + S366P | | + | ++++ |
| 280 | L71F + H95D + D118A + S131C + N202H + N211A + S242T + M250L + A277P + A286K | | + | ++++ |
| 281 | L71F + H95D + D118G + N202H + S242T + M250L | | + | + |
| 282 | L71F + S76M + E82K + D118P + N174S + N202H + A236G + S242T + M250L + S282A + A298E | g84a, g123a, g135a, g315a | + | ++++ |
| 283 | L71F + K72H + E85A + D118P + N202H + S242T + T248Q + M250L + A286V + G360A + S366P | | + | ++++ |
| 284 | K72H + E85A + H95D + D118A + S242T + M250L | | + | ++++ |
| 285 | L71F + N87C + D118A + E135P + N174S + N202H + T203D + S242T + M250L + S282A | | + | ++++ |
| 286 | L71F + E85A + D118P + N202H + N211A + S242T + T248Q + M250L + A286Q | | + | ++ |
| 287 | L71F + K72H + D118P + S131C + N202H + S242T + M250L + G360A + S366P | | + | +++ |

TABLE 4-continued

Improved *M. thermophila* C1 endoglucanase variants identified in Round 3 screening

| Variant Number | Amino acid changes over WT (SEQ ID NO: 1) | SNC | Activity: Fold increase over Variant 213 | Stability: Fold increase over Variant 213 |
|---|---|---|---|---|
| 288 | L71F + S76M + N87C + D118P + N174S + N202H + T203K + S242T + M250L + S282A + G360A + S366P | | + | ++++ |
| 289 | L71F + K94I + D118C + E135P + N202H + S242T + T245V + M250L + S282E + V290Y | | + | ++++ |
| 290 | K70R + L71F + D118P + N202H + S242T + M250L + S282E + V290E + L302K + G360A + S366P | | + | ++++ |
| 291 | K72H + E85D + H95D + D118P + N202H + S242T + M250L + A277P + A286V + L338F | g393c | + | ++++ |
| 292 | L71F + K72H + E85A + D118T + N202H + S242T + T248N + M250L + Q287E + G360A + S366P | | + | +++ |
| 293 | L71F + D118A + Q128T + Q186E + N202H + T203N + S242T + M250L + Q257M + V290W + Y351F + N363H | | + | ++++ |
| 294 | K70R + L71F + K72E + K94I + D118P + N202H + D205P + S242T + T245V + M250L + S270E | | + | ++++ |
| 295 | L71F + L91M + D118P + Q128T + N202H + T203N + S242T + M250L + V290W + A312P + Y351F + N363H | | + | ++++ |
| 296 | K70R + L71F + D118P + Q128T + N202H + T203N + S242C + M250L + Y351F | | + | ++++ |
| 297 | L71F + D118P + Q186E + N202H + T203N + M250L + Q257M + V290W + A312P + Y351F + N363H | | + | ++++ |
| 298 | L71F + D118P + N202H + T203N + S242T + M250L + V290W + N363H | | + | ++++ |
| 299 | H95D + D118P + D134Y + N202H + S242T + M250L | | + | ++++ |
| 300 | L71F + N87C + D118P + N174S + N202H + A236G + S242T + M250L + Q257S + S282A + G360A + S366P | | + | ++++ |
| 301 | L71F + L91M + D118P + N202H + T203N + S242T + M250L + V290W + A312P + Y351F + N363H | | + | ++++ |
| 302 | L71F + S76V + D118P + Q128T + N202H + T203N + M250L + V290W | | + | ++++ |
| 303 | L71F + S76A + D118P + Q128T + N202H + T203N + S242T + M250L + V290W + A312P + Y351F | | + | ++++ |
| 304 | L71F + S76V + L91M + D118P + N202H + T203N + M250L | | + | ++++ |
| 305 | L71F + L91M + D118P + Q128T + N202H + T203N + S242T + M250L + Q257M + Y351F | g393a | + | ++++ |
| 306 | L71F + D118P + E135P + N202H + T203N + S242T + M250L + Q257M + V289L + A312P + N363H | | + | ++++ |
| 307 | L71F + D118P + E135P + N202H + S242T + M250L + G360A + S366P | c225t | + | ++++ |
| 308 | L71F + L91M + D118P + N202H + S242T + M250L + Y351F + N363H | | + | ++++ |
| 309 | L71F + S76V + D118P + N202H + T203N + S242T + M250L + A312P | | + | ++++ |
| 310 | L71F + D118P + N202H + T203N + M250L + Q257M + V290W + Y351F + N363H | | + | ++++ |
| 311 | L71F + D118P + N202H + T203N + S242T + M250L + Q257M + V289L + A312P + N363H | | + | ++++ |
| 312 | L71F + D118P + Q186E + N202H + T203N + S242T + M250L + V290W + A312P + Y351F + N363H | | + | ++++ |
| 313 | L71F + D118P + N202H + T203N + M250L + Q257M + A312P + N363H | | + | ++++ |
| 314 | L71F + E85A + D118A + S131C + N202H + N211A + S242T + T248N + M250L + A286K + Q287E | | + | +++ |

TABLE 4-continued

Improved *M. thermophila* C1 endoglucanase variants identified in Round 3 screening

| Variant Number | Amino acid changes over WT (SEQ ID NO: 1) | SNC | Activity: Fold increase over Variant 213 | Stability: Fold increase over Variant 213 |
|---|---|---|---|---|
| 315 | L71F + L91M + D118P + Q128T + Q186E + N202H + T203N + M250L + Y351F + N363H | | + | ++++ |
| 316 | L71F + S76V + D118P + Q128T + Q186E + N202H + T203N + M250L + Q257M + V290W + A312P + Y351F | | + | ++++ |
| 317 | L71F + L91M + D118P + Q128T + N202H + T203N + S242T + M250L + V290W + Y351F + N363H | | + | ++++ |
| 318 | L71F + L91M + D118P + N202H + T203N + S242T + M250L + Q257M + V290W + A312P | | + | ++++ |
| 319 | L71F + D118C + R177M + N202H + S242T + T245V + M250L + T254V + V290Y | c837t | + | ++++ |
| 320 | L71F + D118A + Q128T + N202H + T203N + S242T + V290W | | + | +++ |
| 321 | L71F + K94I + D118C + N202H + S242T + M250L + T254V + S270E + S282E + V290S + L302K | | + | ++++ |
| 322 | L91M + D118P + E135P + Q186E + N202H + T203N + M250L + V289L + Y351F | | + | ++++ |
| 323 | L71F + D118P + N190S + N202H + S242T + M250L + G360A + S366P | | + | ++++ |
| 324 | L71F + L91M + D118P + Q186E + N202H + T203N + S242T + Y351F | | + | ++++ |
| 325 | L71F + S76V + L91M + D118P + Q128T + N202H + T203N + M250L + N363H | | + | ++++ |
| 326 | L71F + D118P + Q186E + N202H + T203N + S242T + M250L + A312P + N363H | | + | ++++ |
| 327 | L71F + D118P + Q186E + N202H + T203R + M250L + A312P + Y351F + N363H | | + | ++++ |
| 328 | L71F + S76V + D118P + Q128T + N202H + T203N + S242T + M250L + V289L + V290W + Y351F | | + | ++++ |
| 329 | L71F + K94I + D118C + N202H + D205P + S242T + M250L + V290S + G360A | | + | ++++ |
| 330 | L71F + D118P + Q186E + N202H + T203N + S242T + M250L + A312P + Y351F | | + | ++++ |
| 331 | L71F + D118P + N202H + S242T + M250L + N299K + S366P | | + | +++ |
| 332 | L71F + D118P + N202H + S242T + M250L + Q257M + V290W + Y351F + N363H | | + | ++++ |
| 333 | L71F + L91M + D118P + N202H + T203H + S242T + M250L + Y351F | c661a | + | ++++ |
| 334 | L71F + D118C + N202H + S242T + M250L + S270E + V290S | | + | ++++ |
| 335 | L71F + D118P + E135P + Q186E + N202H + T203N + S242T + M250L + Q257M + V289L + A312P + N363H | | + | ++++ |
| 336 | L71F + D118T + N202H + T203N + Q257M + Y351F | | + | +++ |
| 337 | L71F + D118P + D134G + N202H + S242T + M250L | | + | ++ |
| 338 | L71F + S76V + L91M + D118P + N202H + T203N + M250L + Y351F + N363H | | + | ++++ |
| 339 | L71F + D118P + N202H + T203N + S242T + M250L + Y351F | | + | ++++ |
| 340 | L71F + S76V + D118P + N202H + T203N + S242T + M250L + V290W + N363H | | + | ++++ |
| 341 | K70R + L71F + L91M + D118P + Q128T + N202H + T203H + S242T + M250L + A312P + Y351F + N363H | | + | ++++ |
| 342 | L71F + D118P + N202H + T203N + S242T + M250L + Q257M + V289L + A312P | | + | ++++ |

TABLE 4-continued

Improved *M. thermophila* C1 endoglucanase variants identified in Round 3 screening

| Variant Number | Amino acid changes over WT (SEQ ID NO: 1) | SNC | Activity: Fold increase over Variant 213 | Stability: Fold increase over Variant 213 |
|---|---|---|---|---|
| 343 | L71F + D118T + N202H + T203N + S242T + M250L + A312P + Y351F + N363H | | + | ++++ |
| 344 | L71F + D118P + Q128T + Q186E + N202H + T203N + S242T + M250L + Q257M + N363H | | + | ++++ |
| 345 | L71F + L91M + D118P + N202H + S242T + V290W + A312P + Y351F | | + | ++++ |
| 346 | L71F + E85A + D118P + S131C + N202H + S242T + M250L + A286V + Q287E | | + | ++ |
| 347 | L71F + D118C + R177M + N202H + S242T + M250L + T254V | | + | ++++ |
| 348 | L71F + D118P + D134W + N202H + S242T + M250L | | + | ++++ |
| 349 | L71F + H95D + D118P + N202H + S242T + M250L | c802t | + | ++++ |
| 350 | L71F + K94I + D118C + N202H + D205P + S242T + M250L + V290R + L302K | | + | ++++ |
| 351 | L71F + H95D + D118P + E135P + G167D + N202H + S242T + M250L | | + | ++++ |
| 352 | H95D + D118P + D134R + N202H + S242T + M250L | | + | ++++ |
| 353 | L71F + D118P + N202H + S242T + M250L + G360A + S366P | | + | ++++ |
| 354 | K70R + L71F + D118P + R177M + N202H + D205P + S242T + M250L + S270E + L302K + G360A + S366P | | + | ++++ |
| 355 | H95D + D118P + D134S + N202H + S242T + M250L + G360A + S366P | | + | ++++ |
| 356 | L71F + H95D + D118P + E135P + N202H + V232I + S242T + M250L | t111c | + | ++++ |
| 357 | H95D + D118P + N202H + T226G + S242T + M250L | | + | ++++ |
| 358 | L71F + D118P + N202H + G224D + S242T + M250L + G360A + S366P | | + | ++++ |
| 359 | L71F + D118P + D134E + N202H + S242T + M250L + G360A + S366P | | + | ++++ |
| 360 | L71F + D118P + N190V + N202H + S242T + M250L + G360A + S366P | | + | ++++ |
| 361 | L71F + D118P + N202H + G360A + S366P | g642a | + | +++ |
| 362 | L71F + D118P + N190Q + N202H + S242T + M250L + G360A + S366P | | + | ++++ |
| 363 | K70R + L71F + K94I + D118P + N202H + S242T + T245V + M250L + S282E + L302K + G360A + S366P | g360a | + | ++++ |
| 364 | K70R + L71F + D118P + N202H + S242T + M250L + S282E + L302M + G360A + S366P | g762c | + | ++++ |
| 365 | L71F + K94I + D118P + R177M + N202H + S242T + M250L + T254V + V290E | | + | ++ |
| 366 | K70R + L71F + D118C + N202H + S242T + T245V + M250L + S282E + V290R + L302K | | + | ++ |
| 367 | L71F + D118P + R177M + N202H + D205P + S242T + M250L + S282E + V290Y + L302K + G360A + S366P | | + | ++++ |
| 368 | K70R + L71F + D118P + R177M + N202H + D205P + S242T + M250L + T254V | | + | +++ |

Fold increase for activity and stability is represented as follows:
+ = 1.0 to 1.9 fold increase over Variant 213
++ = 2.0 to 2.9 fold increase over Variant 213
+++ = 3.0 to 5.0 fold increase over Variant 213
++++ = greater than 5.0 fold increase over Variant 213
SNC = Silent nucleotide changes

Example 9

Improved Endoglucanase Activities and Stabilities of Engineered *M. thermophila* C1 Endoglucanase Variants—Round 4 Screen Table 5 summarizes the results of the Round 4 screen, which identified improved *M. thermophila* C1 endoglucanase variants derived from Variant 309 (cDNA sequence: SEQ ID NO:9; polypeptide sequence with signal peptide: SEQ ID NO:10; mature polypeptide lacking signal peptide: SEQ ID NO:11). The thermoactivity and thermostability of the endoglucanase variants were compared to the thermoactivity and thermostability of Variant 309. The thermoactivity conditions for the Round 3 screening were pH 4.2 and 70° C. for 18 hours on AVICEL® cellulose. Thermostability was assessed by determining residual enzyme activity on AVICEL® cellulose after incubation at pH 3.5 and 75° C. for 3 hours, or at pH 4.0 and 75° C. for 16 hours. Thermoactivity and thermostability are presented as fold increase over Variant 309. Silent nucleotide changes are indicated with respect to the wild-type *M. thermophila* C1 endoglucanase cDNA sequence (SEQ ID NO:4). Amino acid positions (e.g., "D118") and changes (e.g., "D118P") are relative to mature wild-type *M. thermophila* C1 endoglucanase protein sequence lacking a signal peptide (SEQ ID NO:1).

TABLE 5

Improved *M. thermophila* C1 endoglucanase variants identified in Round 4 screening

| Variant Number | Amino acid changes over WT (SEQ ID NO: 1) | SNC | Activity: Fold increase over Variant 309 | Stability: Fold increase over Variant 309 (3 hrs) | Stability: Fold increase over Variant 309 (16 hrs) |
|---|---|---|---|---|---|
| 309 | L71F + S76V + D118P + N202H + T203N + S242T + M250L + A312P | | — | — | — |
| 369 | R51L + L71F + S76V + D118P + N202H + T203N + S242T + M250L + A312P | | + | | + |
| 370 | L71F + S76V + D118P + D134W + N202H + T203N + S242T + M250L + A312P + S366P | | + | +++ | |
| 371 | T48V + L71F + S76V + D118P + N202H + T203N + S242T + M250L + A312P | | + | | + |
| 372 | L71F + S76V + H95D + D118P + D134W + N202H + T203N + S242T + M250L + A312P + Y351F + G360A + S366P | | + | ++++ | |
| 373 | L71F + S76V + D118P + N202H + T203N + S242T + M250L + S272G + A312P | | + | | ++ |
| 374 | L71F + S76V + D118P + D134G + N174S + N202H + T203N + S242T + M250L + A312P | | + | | ++ |
| 375 | L71F + S76V + D118P + D134H + N174S + N202H + T203N + S242T + T245V + M250L + A286E + A312P + Y351F | | + | | +++ |
| 376 | L71F + S76V + D118P + E135P + N202H + T203N + S242T + M250L + A312P + N330H + G360A | | + | +++ | |
| 377 | W5M + L71F + S76V + D118P + N202H + T203N + S242T + M250L + A312P | | + | | +++ |
| 378 | Q1S + L71F + S76V + D118P + N202H + T203N + S242T + M250L + A312P | | + | | + |
| 379 | L71F + S76V + D118P + N202H + T203N + S242T + M250L + A312P + Y351F + S366P | | + | +++ | |
| 380 | D18Q + L71F + S76V + D118P + N202H + T203N + S242T + M250L + A312P | | + | | ++ |
| 381 | L71F + S76V + D118P + E135P + N202H + T203N + S242T + M250 L + P256R + A312P + G360A | | + | +++ | |
| 382 | L71F + S76V + N87C + D118P + N202H + T203N + S242T + M250L + A312P + N330H | | + | | ++ |
| 383 | T49R + L71F + S76V + D118P + N202H + T203N + S242T + M250L + A312P | | + | | ++ |
| 384 | L71F + S76V + D118P + N202H + T203N + S242T + M250L + A286E + A298D + A312P | | + | | + |
| 385 | Y27R + L71F + S76V + D118P + N202H + T203N + S242T + M250L + A312P | | + | | ++ |

TABLE 5-continued

Improved M. thermophila C1 endoglucanase variants identified in Round 4 screening

| Variant Number | Amino acid changes over WT (SEQ ID NO: 1) | SNC | Activity: Fold increase over Variant 309 | Stability: Fold increase over Variant 309 (3 hrs) | Stability: Fold increase over Variant 309 (16 hrs) |
|---|---|---|---|---|---|
| 386 | L71F + S76V + D118P + E135P + R177M + N202H + T203N + S242T + M250L + A312P + N330H + G360A | | + | +++ | |
| 387 | A54C + L71F + S76V + D118P + N202H + T203N + S242T + M250L + A312P | | + | | + |
| 388 | L71F + S76V + D118P + N202H + T203N + S242T + M250L + A312P + Y351F | | + | +++ | |
| 389 | L71F + S76V + D118P + E135P + R177M + N202H + T203N + S242T + M250L + P256R + V290W + A312P + S366P | | + | ++ | |
| 390 | L71F + H95D + D118P + D134W + N202H + T203N + S242T + M250L + A312P + G360A + S366P | | + | ++++ | |
| 391 | L71F + S76V + D118P + D134H + N202H + T203N + S242T + T245V + M250L + A312P | | + | | + |
| 392 | L71F + S76V + T101C + D118P + F147C + N202H + T203N + S242T + M250L + A312P | | + | +++ | |
| 393 | L71F + S76V + K94I + D118P + N202H + T203N + S242T + M250L + Q287E + A298E + A312P + N363H | | + | +++ | |
| 394 | S56L + L71F + S76V + D118P + N202H + T203N + S242T + M250L + A312P | | + | | + |
| 395 | L71F + S76V + H95D + D118P + N202H + T203N + S242T + M250L + A286E + A312P | | + | ++++ | |
| 396 | L71F + S76V + K94I + H95D + D118P + N202H + T203N + S242T + M250L + A298D + A312P | | + | ++++ | |
| 397 | Q45R + L71F + S76V + D118P + E135P + N202H + T203N + S242T + M250L + Q257S + S282A + A312P + N330H + G360A | | + | ++ | |
| 398 | L71F + S76V + D118P + R177M + N202H + T203N + S242T + M250L + P256R + S282A + V290W + A312P | | + | + | |
| 399 | S61E + L71F + S76V + D118P + N202H + T203N + S242T + M250L + A312P | | + | | + |
| 400 | L71F + S76V + D118P + N202H + T203N + S242T + T245V + M250L + A286E + Q287E + A312P | | + | | + |
| 401 | L71F + S76V + N87C + D118P + N202H + T203N + D205P + S242T + M250L + P256R + S282A + A312P | | + | ++ | |
| 402 | L71F + S76V + D118P + V145C + A155C + N202H + T203N + S242T + M250L + A312P | | + | | ++ |
| 403 | L71F + S76V + N87C + D118P + E135P + N202H + T203N + S242T + M250L + A312P + S366P | | + | +++ | |
| 404 | L71F + S76V + K94I + D118P + D134H + N202H + T203N + S242T + M250L + A312P + N363H | | + | +++ | |
| 405 | L71F + S76V + D118P + E135P + N202H + T203N + S242T + M250L + P256R + Q257S + | | + | +++ | |

TABLE 5-continued

Improved M. thermophila C1 endoglucanase variants identified in Round 4 screening

| Variant Number | Amino acid changes over WT (SEQ ID NO: 1) | SNC | Activity: Fold increase over Variant 309 | Stability: Fold increase over Variant 309 (3 hrs) | Stability: Fold increase over Variant 309 (16 hrs) |
|---|---|---|---|---|---|
| | V290S + A312P + G360A + S366P | | | | |
| 406 | L71F + S76V + D118P + E135P + N202H + T203N + S242T + M250L + S282A + A312P | | + | + | |
| 407 | L71F + S76V + H95D + D118P + N202H + T203N + S242T + M250L + A298E + A312P + N363H | | + | | ++++ |
| 408 | L71F + S76V + D118P + N174S + N202H + T203N + S242T + M250L + A286L + Q287E + A312P + Y351F | | + | | +++ |
| 409 | L71F + S76V + D118P + N202H + T203N + S242T + M250L + S282A + A312P + G360A | | + | +++ | |
| 410 | L71F + S76V + D118P + N202H + T203N + S242T + M250L + A286E + A312P + N363H | | + | | +++ |
| 411 | L71F + S76V + K94I + D118P + N202H + T203N + S242T + T245V + M250L + A312P + N363H | | + | | ++++ |
| 412 | L71F + S76V + D118P + N202H + T203N + S242T + M250L + A312P + G360A + S366P | | + | +++ | |
| 413 | L71F + S76V + D118P + N174S + N202H + T203N + S242T + M250L + A286L + A312P + Y351F | g735c | + | | +++ |
| 414 | L71F + S76V + N87C + D118P + N202H + T203N + S242T + M250L + P256R + V290W + A312P + G360A + S366P | | + | +++ | |
| 415 | L71F + S76V + D118P + N202H + T203N + D205P + S242T + M250L + V290S + A312P + N330H + G360A + S366P | | + | +++ | |
| 416 | L71F + S76V + D118P + N202H + T203N + S242T + M250L + Q287E + A312P + Y351F | | + | | +++ |
| 417 | L71F + S76V + D118P + N202H + T203N + S242T + M250L + A312P + G360A | | + | ++ | |
| 418 | L71F + S76V + D118P + N202H + T203N + S242T + M250L + A286E + A298D + A312P + Y351F | | + | | ++++ |
| 419 | L71F + S76V + K94I + D118P + D134G + N202H + T203N + S242T + M250L + A286L + Q287E + A298E + A312P | | + | | ++ |
| 420 | L71F + S76V + D118P + N202H + T203N + S242T + M250L + P256R + Q257S + A312P + N330H + G360A | | + | ++ | |
| 421 | L71F + S76V + D118P + N202H + T203N + S242T + M250L + A312P + S366P | | + | + | |
| 422 | L71F + S76V + D118P + N174S + N202H + T203N + S242T + M250L + A298D + A312P + Y351F + N363H | | + | | ++++ |
| 423 | L71F + S76V + D118P + D134W + N174S + N202H + T203N + S242T + M250L + A312P + Y351F | | + | | ++++ |
| 424 | L71F + S76V + K94I + H95D + D118P + N202H + T203N + S242T + M250L + A312P + N363H | | + | | ++++ |
| 425 | L71F + S76V + N87C + D118P + E135P + N202H + T203N + S242T + M250L + P256R + | | + | +++ | |

TABLE 5-continued

Improved M. thermophila C1 endoglucanase variants identified in Round 4 screening

| Variant Number | Amino acid changes over WT (SEQ ID NO: 1) | SNC | Activity: Fold increase over Variant 309 | Stability: Fold increase over Variant 309 (3 hrs) | Stability: Fold increase over Variant 309 (16 hrs) |
|---|---|---|---|---|---|
|  | V290S + A312P + N330H + G360A |  |  |  |  |
| 426 | L71F + S76V + D118P + N174D + N202H + T203N + S242T + M250L + A312P + Y351F | g471a | + | +++ |  |
| 427 | S50P + L71F + S76V + H95D + D118P + N202H + T203N + S242T + M250L + Q287E + A312P + Y351F + N363H |  | + |  | ++++ |
| 428 | L71F + S76V + H95D + D118P + D134W + N202H + T203N + S242T + M250L + A312P + Y351F + G360A |  | + | ++++ |  |
| 429 | L71F + S76V + D118P + N202H + T203N + S242T + M250L + A312P + S366P |  | + | ++ |  |
| 430 | L71F + S76V + D118P + D134W + N202H + T203N + S242T + M250L + A312P + Y351F + G360A + S366P |  | + | ++++ |  |
| 431 | L71F + S76V + D118P + N202H + T203N + S242T + M250L + A312P + Y351F + G360A + S366P |  | + | +++ |  |
| 432 | L71F + S76V + D118P + N202H + T203N + S242T + M250L + A312P + Y351F + G360A |  | + | +++ |  |
| 433 | L71F + S76V + N87C + D118P + N202H + T203N + S242T + M250L + P256R + Q257S + S282A + A312P + N330H + S366P |  | + | ++ |  |
| 434 | L71F + S76V + D118P + N174S + N202H + T203N + S242T + M250L + A286E + A298D + A312P + N363H |  | + |  | +++ |
| 435 | L71F + S76V + H95D + D118P + D134T + N174S + N202H + T203N + S242T + T245V + M250L + A298D + A312P + N363H |  | + |  | ++++ |
| 436 | L71F + S76V + H95D + D118P + D134W + N202H + T203N + S242T + M250L + A312P + Y351F + S366P |  | + | ++++ |  |
| 437 | L71F + S76V + H95D + D118P + N202H + T203N + S242T + M250L + A312P + S366P |  | + | +++ |  |
| 438 | K70C + L71F + S76V + D118P + N202H + T203N + S242T + M250L + A312P + Q328C |  | + | + |  |
| 439 | L71F + S76V + H95D + D118P + N202H + T203N + S242T + M250L + A312P + G360A + S366P |  | + | +++ |  |
| 440 | L71F + S76V + D118P + D134T + N202H + T203N + S242T + M250L + Q287E + A298E + A312P + N363H |  | + |  | ++ |
| 441 | L71F + S76V + H95D + D118P + N202H + T203N + S242T + M250L + A312P + Y351F + S366P |  | + | ++++ |  |
| 442 | L71F + S76V + H95D + D118P + D134W + N202H + T203N + S242T + M250L + A312P + S366P |  | + | +++ |  |
| 443 | L71F + S76V + H95D + D118P + D134W + N202H + T203N + S242T + M250L + A312P + Y351F + S366P |  | + | +++ |  |
| 444 | L71F + S76V + H95D + D118P + D134W + N202H + T203N + S242T + M250L + A312P |  | + | +++ |  |

TABLE 5-continued

Improved M. thermophila C1 endoglucanase variants identified in Round 4 screening

| Variant Number | Amino acid changes over WT (SEQ ID NO: 1) | SNC | Activity: Fold increase over Variant 309 | Stability: Fold increase over Variant 309 (3 hrs) | Stability: Fold increase over Variant 309 (16 hrs) |
|---|---|---|---|---|---|
| 445 | L71F + S76V + H95D + D118P + D134W + N202H + T203N + S242T + M250L + A312P + G360A + S366P | | + | ++++ | |
| 446 | L71F + S76V + H95D + D118P + N202H + T203N + S242T + M250L + A312P + G360A | | + | ++++ | |
| 447 | L71F + S76V + H95D + D118P + D134Q + N174S + N202H + T203N + S242T + M250L + A312P | | + | | ++++ |
| 448 | L71F + S76V + H95D + D118P + D134W + N202H + T203N + S242T + M250L + A312P + G360A | | + | ++++ | |
| 449 | L71F + S76V + H95D + D118P + N202H + T203N + S242T + M250L + A298E + A312P + Y351F + N363H | | + | | ++++ |
| 450 | L71F + S76V + D118P + D134W + N202H + T203N + S242T + M250L + S282A + A312P + G360A + S366P | | + | ++++ | |
| 451 | L71F + S76V + D118P + N202H + T203N + A236C + S242C + M250L + A312P | | + | | +++ |
| 452 | L71F + S76V + D118P + D134Y + N202H + T203N + S242T + M250L + A312P + G360A + S366P | | + | | +++ |
| 453 | L71F + S76V + D118P + D134W + N202H + T203N + S242T + M250L + A312P + Y351F + G360A | | + | | ++++ |
| 454 | L71F + S76V + H95D + D118P + D134W + N202H + T203N + S242T + M250L + A312P + Q328C | | + | | ++++ |
| 455 | L71F + S76V + H95D + D118P + N202H + T203N + S242T + M250L + A312P | | + | | ++++ |
| 456 | L71F + S76V + T106A + D118P + D134W + N202H + T203N + S242T + M250L + A312P + Y351F + G360A | | + | | +++ |
| 457 | L71F + S76V + D118P + D134W + N202H + T203N + S242T + M250L + A312P + G360A | c159t | + | | +++ |
| 458 | L71F + S76V + D118P + N202H + T203N + A240C + S242T + M250L + M264C + A312P | | + | | +++ |
| 459 | L71F + S76V + H95D + D118P + N202H + T203N + S242T + M250L + Q287E + A312P | | + | | +++ |
| 460 | L71F + S76V + D118P + D134W + N202H + T203N + D205P + S242T + M250L + Q257S + A312P | | + | +++ | |

Fold increase for activity and stability is represented as follows:
+ = 0.8 to 1.9 fold increase over Variant 309
++ = 2.0 to 2.9 fold increase over Variant 309
+++ = 3.0 to 5.0 fold increase over Variant 309
++++ = greater than 5.0 fold increase over Variant 309
SNC = Silent nucleotide changes

Example 10

Characterization of Thermoactivity and Thermostability of Selected M. thermophila C1 Endoglucanase Variants Four endoglucanase variants (Variant 213, Variant 309, Variant 372, and Variant 443) and wild-type *M. thermophila* C1 endoglucanase, grown in shake flask, were characterized to determine their stability at low pH and high temperature, operating range, and specific activity in yeast. The samples containing various endoglucanase variants or wild-type endoglucanase were pre-incubated at pH 4 or 4.5, at 65° C., 70° C., or 75° C., for 72 hours. The residual enzyme activity after the thermal challenge was measured using AVICEL® cellulose (200 g/L) as a substrate. Table 6 illustrates the residual activity of improved endoglucanase variants at pH 4.5 and 65° C.; pH 4.0 and 65° C.; pH 4.5 and 70° C.; and pH 4.0 and 75. Variant 372 and Variant 443 were stable for up to 72 hours at pH 4 or 4.5, at 65° C., 70° C., or 75° C. In contrast, the wild-type endoglucanase had no residual activity at these conditions.

TABLE 6

Percentage residual activity of improved *M. thermophila* C1 endoglucanase variants versus wild-type

| | pH 4.5, 65° C., 72 hrs | pH 4.0, 65° C., 72 hrs | pH 4.5, 70° C., 72 hrs | pH 4.0, 75° C., 72 hrs |
|---|---|---|---|---|
| WT | 0.1 ± 0.3 | 1.5 ± 0.2 | 2.6 ± 0.2 | 0.7 ± 0.2 |
| Variant 213 | 89.8 ± 2.1 | 9.8 ± 0.4 | 10.6 ± 0.4 | 0.7 ± 0.5 |
| Variant 309 | 100 | 100 | 100 | 0.8 ± 0.2 |
| Variant 372 | 100 | 100 | 95.9 ± 7.2 | 88.8 ± 3.0 |
| Variant 443 | 100 | 100 | 100 | 78.1 ± 4.3 |

Example 11

Production of Improved Endoglucanase Variants in a M. thermophila C1-Derived Host A two-step fermentation process (inoculation and main fermentations starting from spores) was used to express *M. thermophila* C1 endoglucanase variant genes in the *M. thermophila* C1-derived lab strain C1 ΔBgl1, a strain lacking the β-glucosidase 1 gene. Plasmids containing C1 endoglucanase variant genes encoding Variant 213 (SEQ ID NO:6) or Variant 309 (SEQ ID NO:9) as well as the control wild-type endoglucanase were transformed into the *M. thermophila* C1 strain and plated on agar plates containing M3-01 medium with 22.93% sucrose (ingredients of M3-01 Medium: 6.0 g/L Sodium Nitrate, 0.52 g/L Potassium Chloride, 1.52 g/L Potassium Phosphate monobasic ($KH_2PO_4$), 0.24 g/L Magnesium Sulfate, 1.6 mg/L Copper(II) Sulfate pentahydrate ($CuSO_4 5H_2O$), 5 mg/L Ferrous Sulfate heptahydrate ($FeSO_4 7H_2O$), 22 mg/L Zinc Sulfate heptahydrate ($ZnSO_4 7H_2O$), 5 mg/L Manganese(II) Chloride tetrahydrate ($MnCl_2 4H_2O$), 1.8 mg/L Cobalt(II) Sulfate heptahydrate ($CoSO_4 7H_2O$), 1.5 mg/L Sodium Molybdate dihydrate ($Na_2MoO_4 2H_2O$), 11 mg/L Boric Acid, 50 mg/L EDTA, 10.0 g/L Glucose, 1.0 g/L CAS aminoacids (Tritium Microbiologie B. V., The Netherlands), 16 g/L agar, 1 ml/L 1000× Pen/Strep after sterilization (1000× Pen/Step: 2 g Penicillin G and 5 g Streptomycin dissolved in 100 ml $H_2O$, sterilized by filtration). The pH of the medium was adjusted to 6.5 with 10 M KOH and autoclaved for 25 minutes at 121° C. The plates were incubated at 35° C. for 5 days. Spores harvested from the agar plates were used to inoculate a 100 mL F1-01 inoculum medium sterilized in a 500 mL Erlenmeyer flask to reach $5*10^4$-$10^5$ spores/mL initial spore number. (Ingredients of F1-01 Inoculum Medium: 0.50 g/L Potassium Phosphate dibasic ($K_2HPO_4$), 0.05 g/L Potassium Chloride, 0.007 g/L Ferrous Sulfate heptahydrate ($FeSO_4 7H_2O$), 1.00 g/L Yeast Extract (only KAT), 10 g/L Pharmamedia (Traders Protein, Lubbock, Tex., USA), 10 g/L D(+)Lactose monohydrate, 10 g/L Glucose after sterilization, 1 ml/L 1000× Pen/Strep after sterilization (1000× Pen/Step: 2 g Penicillin G and 5 g Streptomycin dissolved in 100 ml $H_2O$, sterilized by filtration). The pH of the medium was adjusted to 7.0 with 10 M NaOH and autoclaved for 25 minutes at 121° C. (the pH of the medium after sterilization was 6.5). To prepare the inoculum culture, the flask was incubated at 35° C., 85% humidity for 3 days with shaking at 250 rpm and 25 mm displacement. 15 mL F1-01 Main Fermentation Medium sterilized in a 100 mL Erlenmeyer flask was inoculated with 750 μL of the obtained inoculum culture (Ingredients of F1-01 Main Fermentation Medium: 0.66 g/L Potassium Phosphate dibasic ($K_2HPO_4$), 0.24 g/L Potassium Phosphate monobasic ($KH_2PO_4$), 8.00 g/L Ammonium Sulphate, 12.00 g/L Sodium Citrate tribasic dehydrate, 0.15 g/L Yeast Extract (only KAT), 0.09 g/L Magnesium Sulfate heptahydrate, 0.80 g/L Calcium Chloride dihydrate, 24.80 g/L Pharmamedia (Traders Protein, Lubbock, Tex., USA), 26.40 g/L D(+)Lactose monohydrate, 64.80 g/L Cellulose (AlphaCel BH200A)). The medium was autoclaved for 25 minutes at 121° C. The main fermentation was carried out by incubation at 35° C., 85% humidity for 6 days with shaking at 300 rpm and 25 mm displacement. After finishing the main fermentation the cells were pelleted by centrifugation (4500 rpm, 15 min, 4° C.). The clear medium supernatant containing the secreted *M. thermophila* C1 endoglucanase was collected and stored at −20° C. until used.

Example 12

Improved Thermostabilities of Endoglucanase Variants Produced in a M. thermophila C1-Derived Host Two *M. thermophila* C1 endoglucanase variants (Variant 213 and Variant 309) and wild-type endoglucanase, produced in the C1-derived host ΔBgl1, were characterized to determine their stabilities at low pH (4.0) and high temperature (75° C.). The samples containing various *M. thermophila* C1 endoglucanase variant enzymes were pre-incubated at pH 4, 75° C. for 1 hr. The residual enzyme activity after the thermal challenge was measured using AVICEL® cellulose as substrate at pH 5, 50° C. for 24 hours. The best variant, Variant 309, retained ~80% activity over the wild-type enzyme (FIG. 1). Comparison of stability profiles of the native enzyme and the two *M. thermophila* C1 endoglucanase variants, produced from yeast and from *M. thermophila* C1, showed good correlation between the two hosts (FIG. 1).

Example 13

Viscosity

The reduction in viscosity of a cellulosic biomass treated with Variant 443 was compared to the reduction achieved using the wild-type enzyme (SEQ ID NO:1). The variant or wild-type enzyme (both 0.09% with respect to the glucan)

was combined with substrate (75 g acid-treated wheat straw per total reaction mass) and incubated at pH 5. Wild-type reactions were carried out at 55° C. and the Variant 443 were carried out at 70° C. The net reduction in viscosity was measured 30 minutes and 72 hours after addition of enzyme was measured with a Perten RVA4 viscometer.

Figure 2:
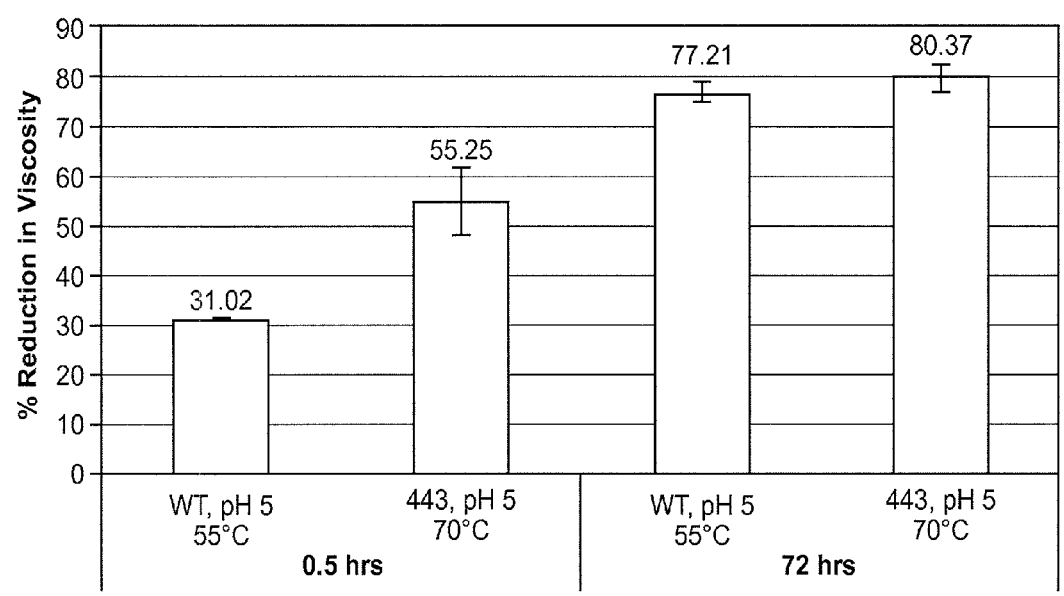
FIG. 2 shows the reduction in viscosity of a cellulosic biomass by wild-type EG2 and a variant EG2.

The results are shown in FIG. 2. The reduction in viscosity for the wild-type enzyme after 30 min at 55° C. was 31%, while the reduction in viscosity for the variant enzyme after 30 min at 70° C. was 55%, indicating the variant had higher activity at elevated temperature. At 72 hours the viscosity observed was similar for variant and wild-type, suggesting that both enzymes proceed as far as possible with the available substrate.

Summary of Selected Sequences

Provided below is a summary of sequences provided in the Sequence Listing:

SEQ ID NO:1: Wild-type *M. thermophila* C1 endoglucanase 2 mature polypeptide sequence (lacking signal peptide).

SEQ ID NO:2: Codon-optimized cDNA sequence of wild-type *M. thermophila* C1 endoglucanase 2 with D332E point mutation used as Round 1 backbone. The sequence encodes a 27-amino acid signal peptide. The protein encoded by SEQ ID NO:2 is SEQ ID NO:3.

SEQ ID NO:3: Wild-type *M. thermophila* C1 endoglucanase 2 polypeptide with D332E point mutation, encoded by codon-optimized cDNA sequence used as Round 1 backbone; including a 27 residue signal peptide (first 27 amino acids of SEQ ID NO3).

SEQ ID NO:4: cDNA sequence encoding wild-type *M. thermophila* C1 endoglucanase 2, used as Round 2 backbone; including a 16-residue signal peptide. The protein encoded by SEQ ID NO:4 is SEQ ID NO:5.

SEQ ID NO:5: Wild-type *M. thermophila* C1 endoglucanase 2 polypeptide encoded by cDNA sequence used as Round 2 backbone; including a 16 amino acid signal peptide (first 16 amino acids of SEQ ID NO:5).

SEQ ID NO:6: *M. thermophila* C1 endoglucanase 2 variant 213 cDNA sequence; including sequence encoding a 16 amino acid signal peptide.

SEQ ID NO:7: *M. thermophila* C1 endoglucanase 2 variant 213 polypeptide sequence; including a 16 amino acid signal peptide (first 16 amino acids of SEQ ID NO7).

SEQ ID NO:8: *M. thermophila* C1 endoglucanase 2 variant 213 mature polypeptide sequence (lacking signal peptide).

SEQ ID NO:9: *M. thermophila* C1 endoglucanase 2 variant 309 cDNA sequence; including sequence encoding a 16 amino acid signal peptide (first 48 nucleotides of SEQ ID NO9).

SEQ ID NO:10: *M. thermophila* C1 endoglucanase 2 variant 309 polypeptide sequence; including a 16 amino acid signal peptide (first 16 amino acids of SEQ ID NO:10).

SEQ ID NO:11: *M. thermophila* C1 endoglucanase 2 variant 309 mature polypeptide sequence (lacking signal peptide).

SEQ ID NO:12: *M. thermophila* C1 endoglucanase 2 variant 372 mature polypeptide sequence (lacking signal peptide).

SEQ ID NO:13: *M. thermophila* C1 endoglucanase 2 variant 443 mature polypeptide sequence (lacking signal peptide).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polynucleotide encoding a variant endoglucanase polypeptide having endoglucanase activity, wherein the polypeptide comprises:
    (a) an amino acid sequence having at least 80% sequence identity to a wild-type endoglucanase 2 (SEQ ID NO:1); and
    (b) an amino acid substitution of at least one of the amino acid residues L71, D118, N202, S242, or M250, wherein the positions are numbered with reference to SEQ ID NO:1.

2. The polynucleotide of claim 1, wherein the variant comprises an amino acid substitution of each of the amino acid residues L71, D118, N202, S242, and M250; and has an amino acid substitution of one or more of the amino acid residues selected from K70, K72, S76, E82, E85, N87, L91, K94, H95, Q128, S131, D134, E135, G167, N174, R177, Q186, N190, T203, D205, N211, G224, T226, V232, A236, T245, T248, T254, Q257, S270, A277, S282, A286, Q287, V289, V290, A298, N299, L302, A312, L338, Y351, G360, N363, and S366, wherein the residues are numbered with reference to SEQ ID NO:1.

3. The polynucleotide of claim 1, wherein the variant comprises the amino acid substitutions L71F, D118P, N202H, S242T, and M250L; and has one or more amino acid substitutions selected from K70R, K72E/H, S76A/M/V, E82K, E85A/D, N87C, L91M, K94I, H95D, Q128T, S131C, D134E/G/R/S/W/Y, E135P, G167D, N174S, R177M, Q186E, N190Q/S/V, T203D/H/K/N/R, D205P, N211A, G224D, T226G, V232I, A236G, T245V, T248N/Q, T254V, Q257E/M/S, S270E, A277P, S282A/E/G, A286E/K/L/V/Q, Q287E, V289L, V290E/R/S/W/Y, A298D/E, N299K, L302K/M, A312P, L338F, Y351F, G360A, N363H, and S366P, wherein the residues are numbered with reference to SEQ ID NO:1.

4. The polynucleotide of claim 1, wherein the variant comprises an amino acid substitution of each of the amino acid residues L71, S76, D118, N202, T203, S242, M250, and A312; and has an amino acid substitution of one or more of the amino acid residues selected from Q1, W5, D18, Y27, Q45, T48, T49, R51, S50, A54, S56, S61, K70, N87, K94, H95, T101, T106, D134, E135, V145, F147, A155, N174, R177, D205, A240, T245, P256, Q257, M264, S272, S282, A286, Q287, V290, A298, Q328, N330, Y351, G360, N363, and S366, wherein the positions are numbered with reference to SEQ ID NO:1.

5. The polynucleotide of claim 1, wherein the variant comprises the amino acid substitutions L71F, S76V, D118P, N202H, T203N, S242T, M250L, and A312P; and has one or more amino acid substitutions selected from Q1S, W5M, D18Q, Y27R, Q45R, T48V, T49R, R51L, S50P, A54C, S56L, S61E, K70C, N87C, K94I, H95D, T101C, T106A, D134G/H/Q/T/W/Y, E135P, V145C, F147C, A155C, N174D/S, R177M, D205P, A240C, T245V, P256R, Q257S, M264C, S272G, S282A, A286E/L, Q287E, V290S/W, A298D/E, Q328C, N330H, Y351F, G360A, N363H, and S366P, wherein the residues are numbered with reference to SEQ ID NO:1.

6. The polynucleotide of claim 1, wherein the variant comprises one or more of the amino acid substitutions selected from L71F, S76V, H95D, D118P, D134W, N202H, T203N, S242T, M250L, A312P, Y351F, G360A, and S366P, wherein the residues are numbered with reference to SEQ ID NO:1.

7. The polynucleotide of claim 6, wherein the variant comprises the amino acid substitutions:
L71F, S76V, H95D, D118P, D134W, N202H, T203N, S242T, M250L, A312P, Y351F, G360A, and S366P; or
L71F, S76V, H95D, D118P, D134W, N202H, T203N, S242T, M250L, A312P, Y351F, and S366P;
L71F, S76V, D118P, N202H, T203N, S242T, M250L, and A312P; or
L71F, D118P, N202H, S242T, and M250L,
wherein the residues are numbered with reference to SEQ ID NO:1.

8. The polynucleotide of claim 1, wherein the variant comprises a residue other than aspartic acid at position 118, numbered with reference to SEQ ID NO:1.

9. The polynucleotide of claim 8, wherein the variant comprises alanine, cysteine, glycine, serine, proline, threonine, or tyrosine at position 118, numbered with reference to SEQ ID NO:1.

10. The polynucleotide of claim 8, wherein the variant comprises proline at position 118, numbered with reference to SEQ ID NO:1.

11. The polynucleotide of claim 8, wherein the variant comprises a residue other than leucine at position 71, other than aspartic acid at position 118, other than asparagine at position 202, other than serine at position 242 and other than methionine at position 250, numbered with reference to SEQ ID NO:1.

12. The polynucleotide of claim 11, wherein the variant comprises proline at position 118, and
a) phenylalanine at position 71; or
b) histidine at position 202; or
c) threonine at position 242; or
d) leucine at position 250;
wherein the variant sequence is numbered with reference to SEQ ID NO:1.

13. The polynucleotide of claim 11, wherein the variant comprises phenylalanine at position 71, proline at position 118, histidine at position 202, threonine at position 242 and leucine at position 250.

14. The polynucleotide of claim 1, wherein the variant has:
(a) increased thermoactivity at pH 4 to pH 5 at 60° C. to 70° C. for 18 hours,
(b) increased thermostability at pH 4 to pH5 at 65° C. to 75° C. for 16 hours, or
(c) both (a) and (b)
relative to wild-type *M. thermophila* endoglucanase (SEQ ID NO:1).

15. A recombinant host cell comprising a polynucleotide of claim 1.

16. A method of producing a variant endoglucanase polypeptide, comprising culturing the host cell of claim 15 under conditions such that the variant endoglucanase polypeptide is produced by the cell.

17. The method of claim 16, wherein the variant endoglucanase polypeptide is secreted from the cell.

* * * * *

UNITED STATES PATENT AND TRADEMARK OFFICE
CERTIFICATE OF CORRECTION

PATENT NO. : 9,512,416 B2  
APPLICATION NO. : 14/542467  
DATED : December 6, 2016  
INVENTOR(S) : Zhang et al.

Page 1 of 1

It is certified that error appears in the above-identified patent and that said Letters Patent is hereby corrected as shown below:

In the Claims

In Column 119, Line 6, Claim 4, please delete "5272, 5282" and insert --S272, S282--.
In Column 119, Line 36, Claim 7, please delete "D1 18P" and insert --D118P--.

Signed and Sealed this
Ninth Day of May, 2017

Michelle K. Lee
*Director of the United States Patent and Trademark Office*